United States Patent
Kawamura et al.

(10) Patent No.: US 6,653,313 B2
(45) Date of Patent: Nov. 25, 2003

(54) 1,4-DIHYDROPYRIDINE COMPOUNDS AS BRADYKININ ANTAGONISTS

(75) Inventors: Mitsuhiro Kawamura, Aichi-ken (JP); Makoto Kawai, Aichi-ken (JP); Yuji Shishido, Aichi-ken (JP); Tomoki Kato, Aichi-ken (JP); Yasuhiro Katsu, Aichi-ken (JP); Takafumi Ikeda, Aichi-ken (JP); Noriaki Murase, Aichi-ken (JP)

(73) Assignee: Warner-Lambert Company LLC, Morris Plains, NJ (US)

( * ) Notice: Subject to any disclaimer, the term of this patent is extended or adjusted under 35 U.S.C. 154(b) by 0 days.

(21) Appl. No.: 09/903,157

(22) Filed: Jul. 11, 2001

(65) Prior Publication Data

US 2002/0161006 A1 Oct. 31, 2002

Related U.S. Application Data

(60) Provisional application No. 60/224,558, filed on Aug. 10, 2000.

(51) Int. Cl.[7] .................. A61K 31/496; A61K 31/5377; C07D 401/14; C07D 413/14
(52) U.S. Cl. .............................. 514/253.04; 514/235.8; 514/253.13; 544/121; 544/362; 544/364; 544/365
(58) Field of Search .................... 544/121, 364, 544/362, 365; 514/235.8, 253.13, 253.04

(56) References Cited

U.S. PATENT DOCUMENTS

| 5,859,011 A | * | 1/1999 | Ito et al. ................ 514/252 |
| 5,861,402 A | * | 1/1999 | Ikeda ..................... 514/252 |
| 6,131,226 A | * | 10/2000 | Ikeda ................... 514/252.13 |
| 6,156,752 A | * | 12/2000 | Ikeda et al. .............. 514/252 |

FOREIGN PATENT DOCUMENTS

| EP | 0790239 | 8/1997 |
| EP | 0899261 | 3/1999 |
| EP | 1106614 | 6/2001 |
| EP | 1106615 | 6/2001 |
| WO | 9606082 | 2/1996 |
| WO | 9606083 | 2/1996 |
| WO | 9730042 | 2/1997 |

OTHER PUBLICATIONS

PCT International Search Report, PCT/IB01/01346.

* cited by examiner

*Primary Examiner*—Emily Bernhardt
(74) *Attorney, Agent, or Firm*—David R. Kurlandsky; Charles W. Ashbrook

(57) ABSTRACT

The present invention relates to compounds of the formula

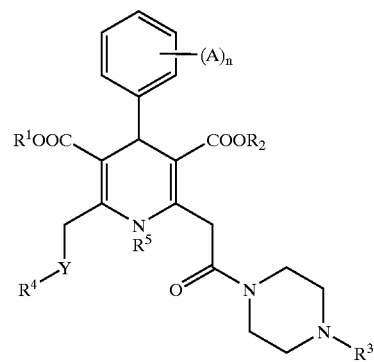

wherein each A is independently halo; Y is —$(CH_2)_m$—, —C(O)— or —S(O)—; $R^1$ and $R^2$ are independently $C_{1-4}$ alkyl; $R^3$ is substituted azacycloalkyl etc.; $R^4$ is phenyl substituted at the 2-position with a substituent selected from substituted $C_{1-7}$ alkyl, substituted $C_{1-7}$ alkoxy, amine, etc; $R^5$ is hydrogen or $C_{1-4}$ alkyl; m is 0, 1 or 2; and n is 0, 1, 2, 3, 4 or 5. The present invention also relates to pharmaceutical compositions containing such compounds and to the use of such compounds in the treatment and prevention of inflammation, asthma, allergic rhinitis, pain and other disorders.

18 Claims, No Drawings

1,4-DIHYDROPYRIDINE COMPOUNDS AS BRADYKININ ANTAGONISTS

This application claims priority under 35 U.S.C. §119(e) from U.S. Provisional Application Serial No. 60/224,558, filed Aug. 10, 2000, which application is hereby incorporated by reference.

This invention relates to 1,4-dihydropyridine compounds. These compounds are useful as antagonists of bradykinin, and are thus useful in the treatment of inflammation, asthma, allergic rhinitis, pain or the like in mammals, including humans. The present invention also relates to pharmaceutical compositions containing such compounds and to the use of such compounds in the treatment and prevention of inflammation, asthma, allergic rhinitis, pain and other disorders.

Bradykinin ("BK") is generated under conditions in mammals by the action of various plasma enzymes such as kalikrein on high molecular weight kininogens. It is widely distributed in mammals, as are its two receptor subtypes, $B_1$ and $B_2$. The actions of BK at the $B_2$ receptor include mainly contraction of arterial and venous preparations, although it can cause relaxation of peripheral resistance vessels as well.

Many of the more important functions of BK, such as increases in vascular permeability, pain, and vasodilatation, however, are mediated by the $B_2$ receptor. These effects at the $B_2$ receptor are believed to be responsible for BK's role in numerous diseases, such as inflammation, cardiovascular disease, pain, and common cold. Hence antagonists at the $B_2$ receptor should find considerable therapeutic applications. Most of the efforts in this area thus far have been studied as analgesics and antiflammatory agents.

Numerous 1,4-dihydropyridine compounds which are $B_2$ antagonists have been synthesized and disclosed in an number of patent publications such as U.S. Pat. No. 5,861,402, EP 899261A1 and WO 97/30048.

International Publication Number WO 96/06082 discloses a variety of 1,4-dihydropyridine compounds having a piperazinylcarbonylmethy group at the 2-position, which compounds are antagonists of bradykinin.

It would be desirable if there were provided a nonpeptide antagonist against the $B_2$ receptor, having potent $B_2$ antagonistic activity without metabolic liability or drug—drug interactions, especially inhibition of P-450 isozymes such as CYP3A4.

SUMMARY OF THE INVENTION the present invention relates to compounds of the formula

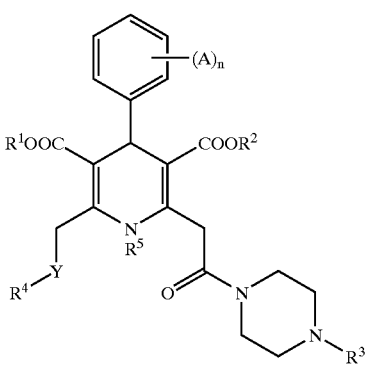

(I)

wherein A is independently halo;
Y is —(CH$_2$)$_m$—, —C(O)— or —S(O)-;
$R^1$ and $R^2$ are independently C$_{1-4}$ alkyl;
$R^3$ is selected from
(a) C$_{7-14}$ azacyclo-, azabicylo- or azatricyclo-alkyl, in which the nitrogen atom optionally has a substituent selected from C$_{1-4}$ alkyl, benzyl optionally substituted with one or two substituents independently selected from halo and halosubstituted—C$_{1-4}$ alkyl, C$_{1-4}$ alkoxycarbonyl optionally substituted with one or two halogen atoms and C$_{1-6}$ acyl;
(b) hydrogen, C$_{1-7}$ alkyl optionally substituted with one or two substituents independently selected from hydroxy, amino, C$_{1-4}$ alkylamino, di-C$_{1-4}$ alkylamino, pyridyl, carbamoyl, pyrrolidinylcarbonyl, C$_{1-4}$ alkylaminocarbonyl, piperidinylcarbonyl, morpholinocarbonyl, 2-oxopyrrolidinyl, C$_{1-4}$ alkysulfonylamino, cyano, C$_{1-6}$ acylamino, 1,1-dioxoisothiazolinyl, 2-oxo-1,3-oxazolidinyl, morpholino, C$_{1-4}$ alkyl-2-oxopyrrolidinyl, piperidinyl and oxo-piperidinyl;
(c) piperidinyl optionally substituted on the nitrogen atom with C$_{1-4}$ alkyl or C$_{1-4}$ alkoxycarbonyl;
(d) C$_{5-14}$ cycloalkyl, bicycloalkyl or tricycloalkyl, the C$_{5-14}$ cycloalkyl, bicycloalkyl or tricycloalkyl being optionally substituted with one or two substituents independently selected from oxo, hydroxy, amino, C$_{1-4}$ alkylamino, di-C$_{1-4}$ alkoxybenzamido, morpholino and oxopyrrolidinyl;
(e) C$_{7-10}$ bicycloalkenyl, benzo-C$_{5-7}$ cycloalkyl or heterocyclic optionally substituted with one or two subtituents independently selected from C$_{1-4}$ alkyl and halo; and
(f) C$_{1-6}$ alkyl-C$_{3-7}$ cycloalkyl, the cycloalkyl moiety being optionally substituted with one, two or three substituents independently selected from cyano, amino-C$_{1-4}$ alkyl-, C$_{1-4}$ alkylamino-C$_{1-4}$ alkyl-, C$_{1-6}$ acylamino-C$_{1-4}$ alkyl-, C$_{1-4}$ alkyl-sulfonylamino-C$_{1-4}$ alkyl, amino, oxopyrrolidinyl, C$_{4-7}$ cycloalkylamino-C$_{1-4}$ alkyl, di-C$_{1-4}$ alkylamino-C$_{1-4}$ alkyl-, hydroxyl, carbamoyl, C$_{1-6}$ acyl (C$_{1-4}$ alkyl) amino, C$_{1-6}$ acyl (C$_{1-4}$ alkyl)amino-C$_{1-4}$ alkyl, di-C$_{1-4}$ alkylamino, pyrrolidinyl-C$_{1-4}$ alkyl, oxopyrrolidinyl-C$_{1-4}$ alkyl and di-C$_{1-4}$ alkylamino-C$_{1-4}$ alkyl;
$R^4$ is phenyl substituted at the 2-position with substituent selected from
(a) C$_{1-4}$ alkyl substituted with one, two or three substituents independently selected from amino, amino-C$_{2-4}$ alkoxy, phenylthio, C$_{1-4}$ alkyl-phenylthio, di-C$_{1-4}$ alkylamino-C$_{2-4}$ alkoxy, C$_{1-4}$ alkylamino-C$_{2-4}$ alkoxy, C$_{1-4}$ alkylamino, di-C$_{1-4}$ alkylamino, hydroxy, C$_{1-4}$ alkoxy, piperazinyl, oxopyrrolidinyl, pyrrolidinyl, C$_{2-4}$ alkylenedioxy, C$_{1-6}$ acyloxy, oxo, morpholino, C$_{1-4}$ alkylaminocarbonyl-C$_{1-4}$ acylamino, C$_{1-4}$ alkoxycarbonyl-C$_{1-6}$ acylamino, C$_{1-4}$ alkoxycarbonylpiperazinyl, C$_{1-6}$ acylpiperazinyl, C$_{1-4}$ alkylthio, heterocyclic-C$_{1-4}$ alkoxy, (di-C$_{1-4}$ alkylamino)(C$_{3-7}$ cycloalkyl)C$_{2-4}$ alkoxy, (C$_{1-4}$ alkylamino)(C$_{3-7}$ cycloalkyl)C$_{2-4}$ alkoxy and (amino)(C$_{3-7}$ cycloalkyl)C$_{2-4}$ alkoxy;
(b) C$_{5-7}$ alkyl optionally substituted with one, two or three substituents independently selected from amino, amino-$C_{2-4}$ alkoxy, phenylthio, $C_{1-4}$ alkyl-phenylthio, di-$C_{1-4}$ alkylamino-$C_{2-4}$ alkoxy, $C_{1-4}$ alkylamino-$C_{2-4}$ alkoxy, $C_{1-4}$ alkylamino, di-$C_{1-4}$ alkylamino, hydroxy, $C_{1-4}$ alkoxy, piperazinyl, oxopyrrolidinyl, pyrrolidinyl, $C_{2-4}$ alkylenedioxy, $C_{1-6}$ acyloxy, oxo, morpholino, $C_{1-4}$ alkylaminocarbonyl-$C_{1-6}$ acylamino, $C_{1-4}$ alkoxycarbonyl-$C_{1-6}$ acylamino, $C_{1-4}$ alkoxycarbonylpiperazinyl, $C_{1-6}$ acylpiperazinyl, $C_{1-4}$ alkylthio, heterocyclic-$C_{1-4}$ alkoxy, (di-$C_{1-4}$ alkylamino)($C_{3-7}$ cycloalkyl)$C_{2-4}$ alkoxy, ($C_{1-4}$ alkylamino)($C_{3-7}$ cycloalkyl)$C_{2-4}$ alkoxy and (amino)($C_{3-7}$ cycloalkyl)$C_{2-4}$ alkoxy;

(c) $C_{1-4}$ alkoxy or $C_{1-4}$ alkylthio, the $C_{1-4}$ alkoxy or $C_{1-4}$ alkylthio being substituted with one, two or three substituents independently selected from amino, amino-$C_{2-4}$ alkoxy, phenylthio, $C_{1-4}$ alkyl-phenylthio, di-$C_{1-4}$ alkylamino-$C_{2-4}$ alkoxy, $C_{1-4}$ alkylamino-$C_{2-4}$ alkoxy, $C_{1-4}$ alkylamino, di-$C_{1-4}$ alkylamino, hydroxy, $C_{1-4}$ alkoxy, piperazinyl, oxopyrrolidinyl, pyrrolidinyl, $C_{2-4}$ alkylenedioxy, $C_{1-6}$ acyloxy, oxo, morpholino, $C_{1-4}$ alkylaminocarbonyl-$C_{1-6}$-acylamino, $C_{1-4}$ alkoxycarbonyl-$C_{1-6}$ acylamino, $C_{1-4}$ alkoxycarbonylpiperazinyl, $C_{1-6}$ acylpiperazinyl, $C_{1-4}$ alkylthio, heterocyclic-$C_{1-4}$ alkoxy, (di-$C_{1-4}$ alkylamino)($C_{3-7}$ cycloalkyl)$C_{2-4}$ alkoxy, ($C_{1-4}$ alkylamino)($C_{3-7}$ cycloalkyl)$C_{2-4}$ alkoxy and (amino)($C_{3-7}$ cycloalkyl)$C_{2-4}$ alkoxy;

(d) $C_{5-7}$ alkoxy or $C_{5-7}$ alkylthio, the $C_{5-7}$ alkoxy or $C_{5-7}$ alkylthio being optionally substituted with one, two or three substitiuents independently selected from amino, amino-$C_{2-4}$ alkoxy, phenylthio, $C_{1-4}$ alkyl-phenylthio, di-$C_{1-4}$ alkylamino-$C_{2-4}$ alkoxy, $C_{1-4}$ alkylamino-$C_{2-4}$ alkoxy, $C_{1-4}$ alkylamino, di-$C_{1-4}$ alkylamino, hydroxy, $C_{1-4}$ alkoxy, piperazinyl, oxopyrrolidinyl, pyrrolidinyl, $C_{2-4}$ alkylenedioxy, $C_{1-6}$ acyloxy, oxo, morpholino, $C_{1-4}$ alkylaminocarbonyl-$C_1$acylamino, $C_{1-4}$ alkoxycarbonyl-$C_{1-6}$ acylamino, $C_{1-4}$ alkoxycarbonylpiperazinyl, $C_{1-6}$ acylpiperazinyl, $C_{1-4}$ alkylthio, heterocyclic-$C_{1-4}$ alkoxy, (di-$C_{1-4}$ alkylamino)($C_{3-7}$ cycloalkyl)$C_{2-4}$ alkoxy, ($C_{1-4}$ alkylamino)($C_{3-7}$ cycloalkyl)$C_{2-4}$ alkoxy and (amino)($C_{3-7}$ cycloalkyl)$C_{2-4}$ alkoxy;

(e) amino, $C_{1-4}$ alkylamino, $C_{1-6}$ acylamino, aminoacetylamino, $C_{1-4}$ alkylsulfonylamino, halosubstituted-$C_{1-4}$ alkylsulfonylamino, halosubstituted-$C_{1-4}$ alkylamino or $C_{1-4}$ alkoxycarbonylaminoacetylamino;

(f) piperazinylcarbonyl, morpholinocarbonyl, nitro, cyano, hydroxy, $C_{1-4}$ alkylsulfonyl, $C_{1-4}$ alkylsulfonyl or di-$C_{1-4}$ alkylaminosulphenyl;

(g) $C_{1-4}$ alkylthio, $C_{1-6}$ alkylthio, amino-$C_{1-6}$ acylthio, $C_{1-4}$ alkylsulfonylthio, halosubstituted-$C_{1-4}$ alkylthio or $C_{1-4}$ alkoxyaminoacetylthio;

(h) $C_{2-7}$ alkenyl or $C_{2-7}$ alkynyl, the $C_{2-7}$ alkenyl or $C_{2-7}$ alkynyl being optionally substituted with one, two or three substituents independently selected from amino, $C_{1-3}$ alkylamino, di-$C_{1-4}$ alkylamino, hydroxy, $C_{1-4}$ alkoxy, piperazinyl, oxopyrrolidinyl, pyrrolidinyl, $C_{2-4}$ alkylenedioxy, halo, $C_{1-6}$ acyloxy, oxo, morpholino, $C_{1-4}$ alkylaminocarbonyl-$C_{1-6}$ acylamino, $C_{1-4}$ alkoxycarbonyl-$C_{1-6}$ acylamino, $C_{1-4}$ alkoxycarbonylpiperazinyl, $C_{1-4}$ acylpiperazinyl and $C_{1-4}$ alkylthio; and (i) $C_{7-14}$ azacycloalkyl optionally substituted with one or two substituents independently selected from oxo and $C_{1-4}$ alkyl;

$R^5$ is hydrogen or $C_{1-4}$ alkyl;

m is 0, 1 or 2; and n is 0, 1, 2, 3, 4 or 5;

and the pharmaceutically acceptable salts and prodrugs thereof.

The present invention also relates to the pharmaceutically acceptable acid addition salts of compounds of the formula (I). The acids which are used to prepare the pharmaceutically acceptable acid addition salts of the aforementioned base compounds of this invention are those which form nontoxic acid addition salts, i.e., salts containing pharmacologically acceptable anions, such as the chloride, bromide, iodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts. The acid addition salts can be prepared by conventional procedures.

The invention also relates to the pharmaceutically acceptable base addition salts of compounds of the formula (I). The chemical bases that may be used as reagents to prepare pharmaceutically acceptable base salts of those compounds of formula (I) that are acidic in nature are those that form non-toxic base salts with such compounds. Such non-toxic base salts include, but are not limited to, those derived from such pharmacologically acceptable cations such as alkali metal cations (e.g. potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines. The base addition salts can be prepared by conventional procedures.

Compounds of formula (I) may contain chiral centers and therefore may exist in different enantiomeric and diastereomeric forms. The present invention relates to all optical isomers and all stereoisomers of compounds of the formula (I), both as racemic mixtures and as individual enantiomers and diastereoisomers of such compounds, and mixtures thereof, and to all pharmaceutical compositions and methods of treatment defined below that contain or employ them, respectively.

As the compounds of formula (I) of this invention possess at least two asymmetric centers, they are capable of occurring in various stereoisomeric forms or configurations. Hence, the compounds may exist in separated (+)- and (−)-optically active forms, as well as mixtures thereof. The present invention includes all such forms within its scope. Individual isomers can be obtained by known methods, such as optical resolution, optically selective reaction or chromatographic separation in the preparation of the final product or its intermediate.

One embodiment of the present invention is directed to compounds with the following stereochemistry

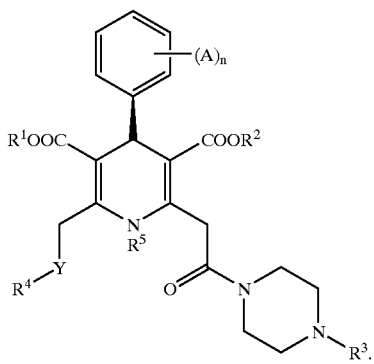

I(a)

Another embodiment of the present invention is directed to compounds with the following stereochemistry

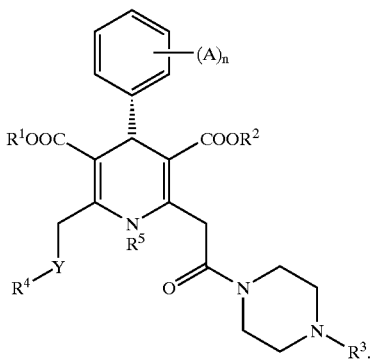

I(b)

$R^3$ and $R^4$ each refer to azabicyclo-, azatricyclo-alkyl, bicycloalkyl, tricycloalkyl, and $C_{7-10}$ bicycloalkenyl groups. Those skilled in the art will appreciate that such groups can exist as multiple stereoisomers including endo and exo orientations. The present invention includes all such stereoisomers. Specific embodiments include the exo isomers of the azabicyclo-, azatricyclo-alkyl, bicycloalkyl, tricycloalkyl, and $C_{7-10}$ bicycloalkenyl groups (such as exo-8-azabicyclo[3.2.1]oct-3-yls). Another specific embodiment includes the endo isomers of the azabicyclo-, azatricyclo-alkyl, bicycloalkyl, tricycloalkyl, and $C_{7-10}$ bicycloalkenyl groups (such as endo-8-azabicyclo[3.2.1]oct-3-yls).

The compounds, salts and prod rugs of the present invention can exist in several tautomeric forms, including the enol and imine form, and the keto and enamine form and geometric isomers and mixtures thereof. All such tautomeric forms are included within the scope of the present invention. Tautomiers exist as mixtures of a tautomeric set in solution. In solid form, usually one tautomer predominates. Even though one tautomer may be described, the present invention includes all tautomers of the present compounds.

The present invention also includes atropisomers of the present invention. Atropisomers refer to compounds of formula (I) that can be separated into rotationally restricted isomers.

The compounds of this invention may contain olefin-like double bonds. When such bonds are present, the compounds of the invention exist as cis and trans configurations and as mixtures thereof.

As used herein, the term "halo" is fluoro, chloro, bromo or iodo (preferably fluoro or chloro).

As used herein, the term "alkyl" means saturated monovalent hydrocarbon radicals having straight or branched moieties, or combinations thereof, including, but not limited to, methyl, ethyl, n-propyl, isopropyl, n-butyl, iso-butyl, secondary-butyl, tertiary-butyl.

As used herein, the term "alkoxy" means alkyl-O—, including, but not limited to methoxy, ethoxy, n-propoxy, isopropoxy, n-butoxy, iso-butoxy, secondary-butoxy, tertiary-butoxy.

As used herein, the term "halosubstituted alkyl" refers to an alkyl radical as described above substituted with one or more halogens, including, but not limited to, chloromethyl, fluoromethyl, difluoromethyl, trifluoromethyl, 2,2,2-trichloroethyl, and the like.

As used herein, the term "acyl" means a group having carbonyl such as R'—C(O)— wherein R' is hydrogen, $C_{1-5}$ alkyl, phenyl or $C_{3-7}$ cycloalkyl, including, but not limited to, formyl, acetyl, ethyl-C(O)—, n-propyl-C(O)—, isopropyl-C(O)—, n-butyl-C(O)—, iso-butyl-C(O)—, secondary-butyl-C(O)—, tertiary-butyl-C(O)—, cyclopropyl-C(O)—, cyclobutyl-C(O)—, cyclopentyl-C(O)—, cyclohexyl-C(O)—, cycloheptyl-C(O)—, and the like.

As used herein, the term "$C_{5-14}$ cycloalkyl, bicycloalkyl or tricycloalkyl" means monocyclic, bicyclic or tricyclic alkyl having 5 to 14 carbon atoms, such as cyclopentyl, cycloheptyl, cyclooctyl, bicyclo[3.2.1]octyl, bicyclo[3.3.0]octyl tricyclo[4.3.3.0]dodecyl, octahydropentalenyl and bicyclo[2.2.1]heptyl.

As used herein, the term "$C_{7-14}$ azacyclo-, azabicyclo- or azatricyclo-alkyl" means monocyclic, bicyclic or tricyclic alkyl having 7 to 14 carbon atoms and one nitrogen atom in the ring, such as quinuclidinyl, azabicyclo[3.2.1]octyl, azabicyclo[3.3.1]nonyl, and azatricyclo[3.3.3.0]undecyl.

As used herein, the term "heterocyclic" means a monocyclic or bicyclic hydrocarbon group which has one or more hetero atoms in the ring, preferably 4 to 10 carbon atoms and 1 to 3 heteroatoms, including such groups as piperidinyl, morpholinyl, thiamorpholinyl, pyrrolidinyl, pyrazolinyl, pyrazolidinyl, pyrzoryl, piperazinyl, furyl, thienyl, oxazolyl, tetrazolyl, thiazolyl, imidazolyl, pyrazolyl, pyrimidinyl, pyrrolyl, pyrrolidinyl, quinolyl and quinuclidinyl.

In the formula (I), A is preferably fluoro or chloro, and more preferably chloro.

In the formula (I), Y is preferably —(CH$_2$)$_m$— wherein m is 1 or 2, and more preferably m is 1.

In the formula (I), $R^1$ and $R^2$ are preferably, independently, methyl or ethyl, and more preferably methyl.

In the formula (I), $R^3$ is preferably (a) $C_{7-14}$ azacyclo-, azabicyclo- or azatricyclo-alkyl, in which the nitrogen atom optionally has a substituent selected from $C_{1-4}$ alkyl, benzyl optionally substituted with one or two substituents independently selected from halo and halosubstituted-$C_{1-4}$ alkyl, $C_{1-4}$ alkoxycarbonyl optionally substituted with one or two halogen atoms and $C_{1-6}$ acyl.

More preferably $R^3$ is $C_{6-9}$ azabicycloalkyl optionally substituted with $C_{1-4}$ alkyl, benzyl or $C_{1-4}$ acyl.

Most preferably $R^3$ is methlylazabicyclo[3.2.1]octyl, ethylazabicyclo[3.2.1]octyl or formylazabicyclo[3.2.1]octyl.

In the formula (1), $R^4$ is preferably phenyl substituted at the 2-position with substituent selected from (a) $C_{1-4}$ alkyl substituted with one, two or three substituents independently selected from amino, amino-$C_{2-4}$ alkoxy, phenylthio, $C_{1-4}$ alkyl-phenylthio, di-$C_{1-4}$ alkylamino-$C_{2-4}$ alkoxy, $C_{1-4}$ alkylamino-$C_{2-4}$ alkoxy, $C_{1-4}$ alkylamino, di-$C_{1-4}$ alkylamino, hydroxy, $C_{1-4}$ alkoxy, piperazinyl, oxopyrrolidinyl, pyrrolidinyl, $C_{2-4}$ alkylenedioxy, $C_{1-6}$ acyloxy, oxo, morpholino, $C_{1-4}$ alkylaminocarbonyl-$C_{1-6}$ acylamino, $C_{1-4}$ alkoxycarbonyl-$C_{1-6}$ acylamino, $C_{1-4}$ alkoxycarbonylpiperazinyl, $C_{1-6}$ acylpiperazinyl, $C_{1-4}$ alkylthio, heterocyclic-$C_{1-4}$ alkoxy, (di-$C_{1-4}$ alkylamino)($C_{3-7}$ cycloalkyl)$C_{2-4}$ alkoxy, ($C_{1-4}$ alkylamino)($C_{3-7}$ cycloalkyl)$C_{2-4}$ alkoxy and (amino)($C_{3-7}$ cycloalkyl)$C_{2-4}$ alkoxy;

(b) $C_{5-7}$ alkyl optionally substituted with one, two or three substituents independently selected from amino, amino-$C_{2-4}$ alkoxy, phenylthio, $C_{1-4}$ alkyl-phenylthio, di-$C_{1-4}$ alkylamino-$C_{2-4}$ alkoxy, $C_{1-4}$ alkylamino-$C_{2-4}$ alkoxy, $C_{1-4}$ alkylamino, di-$C_{1-4}$ alkylamino, hydroxy, $C_{1-4}$ alkoxy, piperazinyl, oxopyrrolidinyl, pyrrolidinyl, $C_{2-4}$ alkylenedioxy, $C_{1-6}$ acyloxy, oxo, morpholino, $C_{1-4}$ alkylaminocarbonyl-$C_{1-6}$ acylamino, $C_{1-4}$ alkoxycarbonyl-$C_{1-6}$ acylamino, $C_{1-4}$ alkoxycarbonylpiperazinyl, $C_{1-6}$ acylpiperazinyl, $C_{1-4}$ alkylthio, heterocyclic-$C_{1-4}$ alkoxy, (di-$C_{1-4}$ alkylamino)($C_{3-7}$ cycloalkyl)$C_{2-4}$ alkoxy, ($C_{1-4}$ alkylamino)($C_{3-7}$ cycloalkyl)$C_{2-4}$ alkoxy and (amino)($C_{3-7}$ cycloalkyl)$C_{2-4}$ alkoxy;

(c) $C_{1-4}$ alkoxy or $C_{1-4}$ alkylthio, the $C_{1-4}$ alkoxy or $C_{1-4}$ alkylthio being substituted with one, two or three substituents independently selected from amino, amino-$C_{2-4}$ alkoxy, phenylthio, $C_{1-4}$ alkyl-phenylthio, di-$C_{1-4}$ alkylamino-$C_{2-4}$ alkoxy, $C_{1-4}$ alkylamino-$C_{2-4}$ alkoxy, $C_{1-4}$ alkylamino, di-$C_{1-4}$ alkylamino, hydroxy, $C_{1-4}$ alkoxy, piperazinyl, oxopyrrolidinyl, pyrrolidinyl, $C_{2-4}$ alkylenedioxy, $C_{1-6}$ acyloxy, oxo, morpholino, $C_{1-4}$ alkylaminocarbonyl-$C_{1-6}$ acylamino, $C_{1-4}$ alkoxycarbonyl-$C_{1-6}$ acylamino, $C_{1-4}$ alkoxycarbonylpiperazinyl, $C_{1-6}$ acylpiperazinyl, $C_{1-4}$ alkylthio, heterocyclic-$C_{1-4}$ alkoxy, (di-$C_{1-4}$ alkylamino)($C_{3-7}$ cycloalkyl)$C_{2-4}$ alkoxy, ($C_{1-4}$ alkylamino)($C_{3-7}$ cycloalkyl)($C_{2-4}$ alkoxy and (amino)($C_{3-7}$ cycloalkyl)$C_{2-4}$ alkoxy;

(d) $C_{5-7}$ alkoxy or $C_{5-7}$ alkylthio, the $C_{5-7}$ alkoxy or $C_{5-7}$ alkylthio being optionally substituted with one, two or three substituents independently selected from amino, amino-$C_{2-4}$ alkoxy, phenylthio, $C_{1-4}$ alkyl-phenylthio, di-$C_{1-4}$ alkylamino-$C_{2-4}$ alkoxy, $C_{1-4}$ alkylamino-$C_{2-4}$ alkoxy, $C_{1-4}$ alkylamino, di-$C_{1-4}$ alkylamino, hydroxy, $C_{1-4}$ alkoxy, piperazinyl, oxopyrrolidinyl, pyrrolidinyl, $C_{2-4}$ alkylenedioxy, $C_{1-6}$ acyloxy, oxo, morpholino, $C_{1-4}$ alkylaminocarbonyl-$C_{1-4}$ acylamino, $C_{1-4}$ alkoxycarbonyl-$C_{1-6}$ acylamino, $C_{1-4}$ alkoxycarbonylpiperazinyl, $C_1$ acylpiperazinyl, $C_{1-4}$ alkylthio, heterocyclic-$C_{1-4}$ alkoxy, (di-$C_{1-4}$ alkylamino)($C_{3-7}$ cycloalkyl)$C_{2-4}$ alkoxy, ($C_{1-4}$ alkylamino)($C_{3-7}$ cycloalkyl)$C_{2-4}$ alkoxy and (amino)($C_{3-7}$ cycloalkyl)$C_{2-4}$ alkoxy;

(e) amino, $C_{1-4}$ alkylamino, $C_{1-6}$ acylamino, aminoacetylamino, $C_{1-4}$ alkylsulfonylamino, halosubstituted-$C_{1-4}$ alkylsulfonylamino, halosubstituted-$C_{1-4}$ alkylamino or $C_{1-4}$ alkoxycarbonylaminoacetylamino;

(f) piperazinylcarbonyl, morpholinocarbonyl, nitro, cyano, hydroxy, $C_{1-4}$ alkylsulfonyl, $C_{1-4}$ alkylsulfinyl or di-$C_{1-4}$ alkylaminosulphenyl; and (i) ($C_{7-14}$ azacycloalkyl optionally substituted with one or two substituents independently selected from oxo and $C_{1-4}$ alkyl.

More preferably $R^4$ is phenyl substituted at the 2-position with substituent selected from (a) $C_{1-4}$ alkyl substituted with one, two or three substituents independently selected from amino, amino-$C_{2-4}$ alkoxy, phenylthio, $C_{1-4}$ alkyl-phenylthio, di-$C_{1-4}$ alkylamino-$C_{2-4}$ alkoxy, $C_{1-4}$ alkylamino-$C_{2-4}$ alkoxy, $C_{1-4}$ alkylamino, di-$C_{1-4}$ alkylamino, hydroxy, $C_{1-4}$ alkoxy, piperazinyl, oxopyrrolidinyl, pyrrolidinyl, $C_{2-4}$ alkylenedioxy, $C_{1-6}$ acyloxy, oxo, morpholino, $C_{1-4}$ alkylaminocarbonyl-$C_{1-6}$ acylamino, $C_{1-4}$ alkoxycarbonyl-$C_{1-6}$ acylamino, $C_{1-4}$ alkoxycarbonylpiperazinyl, $C_{1-4}$ acylpiperazinyl, $C_{1-4}$ alkylthio, heterocyclic-$C_{1-4}$ alkoxy, (di-$C_{1-4}$ alkylamino)($C_{3-7}$ cycloalkyl)$C_{2-4}$ alkoxy, ($C_{1-4}$ alkylamino)($C_{3-7}$ cycloalkyl)$C_{2-4}$ alkoxy and (amino)($C_{3-7}$ cycloalkyl)$C_{2-4}$ alkoxy;

(c) $C_{1-4}$ alkoxy or $C_{1-4}$ alkylthio, the $C_{1-4}$ alkoxy or $C_{1-4}$ alkylthio being substituted with one, two or three substituents independently selected from amino, amino-$C_{2-4}$ alkoxy, phenylthio, $C_{1-4}$ alkyl-phenylthio, di-$C_{1-4}$ alkylamino-$C_{2-4}$ alkoxy, $C_{1-4}$ alkylamino-$C_{2-4}$ alkoxy, $C_{1-4}$ alkylamino, di-$C_{1-4}$ alkylamino, hydroxy, $C_{1-4}$ alkoxy, piperazinyl, oxopyrrolidinyl, pyrrolidinyl, $C_{2-4}$ alkylenedioxy, $C_{1-6}$ acyloxy, oxo, morpholino, $C_{1-4}$ alkylaminocarbonyl-$C_1$-acylamino, $C_{1-4}$ alkoxycarbonyl-$C_{1-6}$ acylamino, $C_{1-4}$ alkoxycarbonylpiperazinyl, $C_{1-6}$ acylpiperazinyl, $C_{1-4}$ alkylthio, heterocyclic-$C_{1-4}$ alkoxy, (di-$C_{1-4}$ alkylamino)($C_{3-7}$ cycloalkyl)$C_{2-4}$ alkoxy, ($C_{1-4}$ alkylamino)($C_{3-7}$ cycloalkyl)$C_{2-4}$ alkoxy and (amino)($C_{3-7}$ cycloalkyl)$C_{2-4}$ alkoxy;

(e) amino, $C_{1-4}$ alkylamino, C, c acylamino, aminoacetylamino, $C_{1-4}$ alkylsulfonylamino, halosubstituted-$C_{1-4}$ alkylsulfonylamino, halosubstituted-$C_{1-4}$ alkylamino or $C_{1-4}$alkoxycarbonylaminoacetylamino; and (f) piperazinylcarbonyl, morpholinocarbonyl, nitro, cyano, hydroxy, $C_{1-4}$ alkylsulfonyl, $C_{1-4}$ alkylsulfinyl or di-$C_{1-4}$ alkylaminosulphenyl, More preferably $R^4$ is phenyl substituted at the 2-position with substituent selected from (a) $C_{1-4}$ alkyl substituted with one or two substituents independently selected from amino, amino-$C_{2-4}$ alkoxy, phenylthio, $C_{1-4}$ alkyl-phenylthio, di-$C_{1-4}$ alkylamino-$C_{2-4}$ alkoxy, $C_{1-4}$ alkylamino-$C_{2-4}$ alkoxy, $C_{1-4}$ alkylamino, di-$C_{1-4}$ alkylamino, hydroxy, piperazinyl, oxopyrrolidinyl, pyrrolidinyl, morpholino, $C_{1-4}$ alkylaminocarbonyl-$C_{1-6}$ acylamino, $C_{1-4}$ alkoxycarbonyl-$C_{1-6}$ acylamino, $C_{1-4}$ alkoxycarbonylpiperazinyl, $C_{3-7}$ heterocyclic-$C_{1-4}$ alkoxy and $C_{1-6}$ acylpiperazinyl;

(c) $C_{1-4}$ alkoxy substituted with one or two substituents independently selected from amino, $C_{1-4}$ alkylamino, di-$C_{1-4}$ alkylamino, hydroxy, piperazinyl, oxopyrrolidinyl, pyrrolidinyl, morpholino, $C_{1-4}$ alkylaminocarbonyl-$C_{1-6}$ acylamino, $C_{1-4}$ alkoxycarbonyl-$C_{1-6}$ acylamino, $C_{1-4}$ alkoxycarbonylpiperazinyl and $C_{1-4}$ acylpiperazinyl;

(e) amino, $C_{1-4}$ alkylamino, $C_{1-6}$ acylamino, aminoacetylamino, $C_{1-4}$ alkylsulfonylamino, halosubstituted-$C_{1-4}$ alkylsulfonylamino, halosubstituted-$C_{1-4}$ alkylamino or $C_{1-4}$ alkoxycarbonylaminoacetylamino; and (f) piperazinylcarbonyl, hydroxy or di-$C_{1-4}$ alkylaminosulphenyl.

Most preferably $R^4$ is phenyl substituted at the 2-position with substituent selected from ethylenedioxyethyl, aminoethoxymethyl, aminoethoxy, aminopropoxy, aminopropoxymethyl, phenylthiomethyl, dimethylaminopropyl, diethylaminomethyl, hydroxy, morpholinomethyl, methanesulphonylamino, oxopyrrolidinoethoxy, t-butoxycarbonylpiperazinomethyl, trifluoroethylamino, methylcarbamoylpropanoyl-aminomethyl, diethylaminoethoxymethyl, trifuloromethanesulfonylamino, piperazinocarbonyl, ethylaminoethoxymethyl, pyrrolidinoethoxy, morpholinoethoxy, piperidinoethoxy and dimethylaminoethoxy.

In the formula (I), $R^5$ is preferably hydrogen, methyl or ethyl, and more preferably hydrogen.

In the formula (I), n is preferably 1, 2, or 3, and most preferably 2.

Preferred compounds of this invention are those of the formula (I) wherein

A is independently fluoro or chloro;

Y is —$(CH_2)_m$;

$R^1$ and $R^2$ are independently methyl or ethyl;

$R^3$ is $C_{7-14}$ azacyclo-, azabicyclo- or azatricyclo-alkyl, in which the nitrogen atom optionally has a substituent selected from $C_{1-4}$ alkyl, benzyl optionally substituted with one or two substituents independently selected from halo and halosubstituted-$C_{1-4}$ alkyl, $C_{1-4}$ alkoxycarbonyl optionally substituted with one or two halogen atoms and $C_{1-6}$ acyl;

$R^4$ is phenyl substituted at the 2-position with substituent selected from (a) $C_{1-4}$ alkyl substituted with one, two or three substituents independently selected from amino, amino-$C_{2-4}$ alkoxy, phenylthio, $C_{1-4}$ alkyl-phenylthio, di-$C_{1-4}$ alkylamino-$C_{2-4}$ alkoxy, $C_{1-4}$ alkylamino-$C_{2-4}$ alkoxy, $C_{1-4}$ alkylamino, di-$C_{1-4}$ alkylamino, hydroxy, $C_{1-4}$ alkoxy, piperazinyl, oxopyrrolidinyl, pyrrolidinyl, $C_{2-4}$ alkylenedioxy, $C_{1-6}$ acyloxy, oxo, morpholino, $C_{1-4}$ alkylaminocarbonyl-$C_{1-6}$ acylamino, $C_{1-4}$ alkoxycarbonyl-$C_{1-6}$ acylamino, $C_{1-4}$ alkoxycarbonylpiperazinyl, $C_{1-6}$ acylpiperazinyl, $C_{1-4}$ alkylthio, heterocyclic-$C_{1-4}$ alkoxy, (di-$C_{1-4}$ alkylamino)($C_{3-7}$ cycloalkyl)$C_{2-4}$ alkoxy, ($C_{1-4}$ alkylamino)($C_{3-7}$ cycloalkyl)$C_{2-4}$ alkoxy and (amino)($C_{3-7}$ cycloalkyl)$C_{2-4}$ alkoxy;

(b) $C_{5-7}$ alkyl optionally substituted with one, two or three substituents independently selected from amino, amino-$C_{2-4}$ alkoxy, phenylthio, $C_{1-4}$ alkyl-phenylthio, di-$C_{1-4}$ alkylamino-$C_{2-4}$ alkoxy, $C_{1-4}$ alkylamino-$C_{2-4}$ alkoxy, $C_{1-4}$ alkylamino, di-$C_{1-4}$ alkylamino, hydroxy, $C_{1-4}$ alkoxy, piperazinyl, oxopyrrolidinyl, pyrrolidinyl, $C_{2-4}$ alkylenedioxy, $C_{1-6}$ acyloxy, oxo, morpholino, $C_{1-4}$ alkylaminocarbonyl-$C_{1-6}$ acylamino, $C_{1-4}$ alkoxycarbonyl-$C_{1-6}$ acylamino, $C_{1-4}$ alkoxycarbonylpiperazinyl, $C_{1-6}$ acylpiperazinyl, $C_{1-4}$ alkylthio, heterocyclic-$C_{1-4}$ alkoxy, (di-$C_{1-4}$ alkylamino)($C_{3-7}$ cycloalkyl)$C_{2-4}$ alkoxy, ($C_{1-4}$ alkylamino)($C_{3-7}$ cycloalkyl)$C_{2-4}$ alkoxy and (amino)($C_{3-7}$ cycloalkyl)$C_{2-4}$ alkoxy;

(c) $C_{1-4}$ alkoxy or $C_{1-4}$ alkylthio, the $C_{1-4}$ alkoxy or $C_{1-4}$ alkylthio being substituted with one, two or three substituents independently selected from amino, amino-$C_{2-4}$ alkoxy, phenylthio, $C_{1-4}$ alkyl-phenylthio, di-$C_{1-4}$ alkylamino-$C_{2-4}$ alkoxy, $C_{1-4}$ alkylamino-$C_{2-4}$ alkoxy, $C_{1-4}$ alkylamino, di-$C_{1-4}$ alkylamino, hydroxy, $C_{1-4}$ alkoxy, piperazinyl, oxopyrrolidinyl, pyrrolidinyl, $C_{2-4}$ alkylenedioxy, $C_{1-6}$ acyloxy, oxo, morpholino, $C_{1-4}$ alkylaminocarbonyl-$C_1$-acylamino, $C_{1-4}$ alkoxycarbonyl-$C_{1-6}$ acylamino, $C_{1-4}$ alkoxycarbonylpiperazinyl, $C_1$-acylpiperazinyl, $C_{1-4}$ alkylthio, heterocyclic-$C_{1-4}$ alkoxy, (di-$C_{1-4}$ alkylamino)($C_{3-7}$ cycloalkyl)$C_{2-4}$ alkoxy, ($C_{1-4}$ alkylamino)($C_{3-7}$ cycloalkyl)$C_{2-4}$ alkoxy and (amino)($C_{3-7}$ cycloalkyl)$C_{2-4}$ alkoxy;

(d) $C_{5-7}$ alkoxy or $C_{5-7}$ alkylthio, the $C_{5-7}$ alkoxy or $C_{5-7}$ alkylthio being optionally substituted with one, two or three substituents independently selected from amino, amino-$C_{2-4}$ alkoxy, phenylthio, $C_{1-4}$ alkyl-phenylthio, di-$C_{1-4}$ alkylamino-$C_{2-4}$ alkoxy, $C_{1-4}$ alkylamino-$C_{2-4}$ alkoxy, $C_{1-4}$ alkylamino, di-$C_{1-4}$ alkylamino, hydroxy, $C_{1-4}$ alkoxy, piperazinyl, oxopyrrolidinyl, pyrrolidinyl, $C_{2-4}$ alkylenedioxy, $C_{1-6}$ acyloxy, oxo, morpholino, $C_{1-4}$ alkylaminocarbonyl-$C_1$-acylamino, $C_{1-4}$ alkoxycarbonyl-$C_{1-6}$ acylamino, $C_{1-4}$ alkoxycarbonylpiperazinyl, $C_{1-6}$ acylpiperazinyl, $C_{1-4}$ alkylthio, heterocyclic-$C_{1-4}$ alkoxy, (di-$C_{1-4}$ alkylamino)($C_{3-7}$ cycloalkyl)$C_{2-4}$ alkoxy, ($C_{1-4}$ alkylamino)($C_{3-7}$ cycloalkyl)$C_{2-4}$ alkoxy and (amino)($C_{3-7}$ cycloalkyl)$C_{2-4}$ alkoxy;

(e) amino, $C_{1-4}$ alkylamino, $C_{1-6}$ acylamino, aminoacetylamino, $C_{1-4}$ alkylsulfonylamino, halosubstituted-$C_{1-4}$ alkylsulfonylamino, halosubstituted-$C_{1-4}$ alkylamino or $C_{1-4}$ alkoxycarbonylaminoacetylamino;

(f) piperazinylcarbonyl, morpholinocarbonyl, nitro, cyano, hydroxy, $C_{1-4}$ alkylsulfonyl, $C_{1-4}$ alkylsulfinyl or di-$C_{1-4}$ alkylaminosulphenyl; and (i) $C_{7-14}$ azacycloalkyl optionally substituted with one or two substituents independently selected from oxo and $C_{1-4}$ alkyl;

$R^5$ is hydrogen;

m is 1 or 2; and n is 1, 2 or 3.

One embodiment of the present invention is directed to the above preferred compounds of the formula (I) wherein the azabicyclo- or azatricylo-alkyl group of $R^3$ is in the exo orientation.

One embodiment of the present invention is directed to the above preferred compounds of the formula (I) wherein the azabicyclo- or azatricylo-alkyl group of $R^3$ is in the endo orientation.

More preferred compounds of this, invention are those of the formula (I) wherein $(A)_n$ is 2,6-dichloro; Y is —$(CH_2)$—; $R^1$ and $R^2$ are methyl;

$R^3$ is $C_{7-14}$ azacyclo- or azabicyclo-alkyl, in which the nitrogen atom optionally has a substituent selected from $C_{1-4}$ alkyl, benzyl optionally substituted with one or two substituents independently selected from halo and halosubstituted-$C_{1-4}$ alkyl, $C_{1-4}$ alkoxycarbonyl optionally substituted with one or two halogen atoms and $C_{1-4}$ acyl;

$R^4$ is phenyl substituted at the 2-position with substituent selected from (a) $C_{1-4}$ alkyl substituted with one, two or three substituents independently selected from amino, amino-$C_{2-4}$ alkoxy, phenylthio, $C_{1-4}$ alkyl-phenylthio, di-$C_{1-4}$ alkylamino-$C_{2-4}$ alkoxy, $C_{1-4}$ alkylamino-$C_{2-4}$ alkoxy, $C_{1-4}$ alkylamino, di-$C_{1-4}$ alkylamino, hydroxy, $C_{1-4}$ alkoxy, piperazinyl, oxopyrrolidinyl, pyrrolidinyl, $C_{2-4}$ alkylenedioxy, $C_{1-6}$ acyloxy, oxo, morpholino, $C_{1-4}$ alkylaminocarbonyl-$C_{1-6}$ acylamino, $C_{1-4}$ alkoxycarbonyl-$C_{1-6}$ acylamino, $C_{1-4}$ alkoxycarbonylpiperazinyl, $C_{1-6}$ acylpiperazinyl, $C_{1-4}$ alkylthio, heterocyclic-$C_{1-4}$ alkoxy, (di-$C_{1-4}$ alkylamino)($C_{3-7}$ cycloalkyl)$C_{2-4}$ alkoxy, ($C_{1-4}$ alkylamino)($C_{3-7}$ cycloalkyl)$C_{2-4}$ alkoxy and (amino)($C_{3-7}$ cycloalkyl)$C_{2-4}$ alkoxy;

(c) $C_{1-4}$ alkoxy or $C_{1-4}$ alkylthio, the $C_{1-4}$ alkoxy or $C_{1-4}$ alkylthio being substituted with one, two or three substituents independently selected from amino, amino-$C_{2-4}$ alkoxy, phenylthio, $C_{1-4}$ alkyl-phenylthio, di-$C_{1-4}$ alkylamino-$C_{2-4}$ alkoxy, $C_{1-4}$ alkylamino-$C_{2-4}$ alkoxy, $C_{1-4}$ alkylamino, di-$C_{1-4}$ alkylamino, hydroxy, $C_{1-4}$ alkoxy, piperazinyl, oxopyrrolidinyl, pyrrolidinyl, $C_{2-4}$ alkylenedioxy, $C_{1-4}$ acyloxy, oxo, morpholino, $C_{1-4}$ alkylaminocarbonyl-$C_{1-6}$ acylamino, $C_{1-4}$ alkoxycarbonyl-$C_{1-6}$ acylamino, $C_{1-4}$ alkoxycarbonylpiperazinyl, $C_{1-6}$ acylpiperazinyl, $C_{1-4}$ alkylthio, heterocyclic-$C_{1-4}$ alkoxy, (di-$C_{1-4}$ alkylamino)($C_{3-7}$ cycloalkyl)$C_{2-4}$ alkoxy, ($C_{1-4}$ alkylamino)($C_{3-7}$ cycloalkyl)$C_{2-4}$ alkoxy and (amino)($C_{3-7}$ cycloalkyl)$C_{2-4}$ alkoxy;

(e) amino, $C_{1-4}$ alkylamino, $C_{1-6}$ acylamino, aminoacetylamino, $C_{1-4}$ alkylsulfonylamino, halosubstituted-$C_{1-4}$ alkylsulfonylamino, halosubstituted-$C_{1-4}$ alkylamino or $C_{1-4}$ alkoxycarbonylaminoacetylamino; and (f) piperazinylcarbonyl, morpholinocarbonyl, nitro, cyano, hydroxy, $C_{1-4}$ alkylsulfonyl, $C_{1-4}$ alkylsulfinyl or di-$C_{1-4}$ alkylaminosulphenyl;

and $R^5$ is hydrogen.

Other preferred compounds of this invention are those of the formula (I) wherein $R^3$ is $C_{6-9}$ azabicycloalkyl optionally substituted with $C_{1-4}$ alkyl, benzyl or $C_{1-4}$ acyl; or $R^4$ is phenyl substituted at the 2-position with substituent selected from (a) $C_{1-4}$ alkyl substituted with one or two substituents independently selected from amino, amino-$C_{2-4}$ alkoxy, phenylthio, $C_{1-4}$ alkyl-phenylthio, di-$C_{1-4}$ alkylamino-$C_{2-4}$ alkoxy, $C_{1-4}$ alkylamino-$C_{2-4}$ alkoxy, $C_{1-4}$ alkylamino, di-$C_{1-4}$ alkylamino, hydroxy, piperazinyl, oxopyrrolidinyl, pyrrolidinyl, morpholino, $C_{1-4}$ alkylaminocarbonyl-$C_{1-6}$ acylamino, $C_{1-4}$ alkoxycarbonyl-$C_{1-6}$ acylamino, $C_{1-4}$ alkoxycarbonylpiperazinyl, $C_{3-7}$ heterocyclic-$C_{1-4}$ alkoxy and $C_{1-6}$ acylpiperazinyl;

(c) $C_{1-4}$ alkoxy substituted with one or two substituents independently selected from amino, $C_{1-4}$ alkylamino, di-$C_{1-4}$ alkylamino, hydroxy, piperazinyl, oxopyrrolidinyl, pyrrolidinyl, morpholino, $C_{1-4}$ alkylaminocarbonyl-$C_{1-6}$ acylamino, $C_{1-4}$ alkoxycarbonyl-$C_{1-6}$ acylamino, $C_{1-4}$ alkoxycarbonylpiperazinyl, and $C_{1-6}$ acylpiperazinyl;

(e) amino, $C_{1-4}$ alkylamino, $C_{1-6}$ acylamino, aminoacetylamino, $C_{1-4}$ alkylsulfonylamino, halosubstituted-$C_{1-4}$ alkylsulfonylamino, halosubstituted-$C_{1-4}$ alkylamino or $C_{1-4}$alkoxycarbonylaminoacetylamino; and (f) piperazinylcarbonyl, hydroxy or di-$C_{1-4}$ alkylaminosulphenyl.

Other preferred compounds of this invention are those of the formula (I) wherein $R^3$ is methlylazabicyclo[3.2.1]octyl, ethylazabicyclo[3.2.1]octyl or formylazabicyclo[3.2.1]octyl; and $R^4$ is phenyl substituted at the 2-position with substituent selected from ethylenedioxyethyl, aminoethoxymethyl, aminoethoxy, aminopropoxy, aminopropoxymethyl, phenylthiomethyl, (dimethylamino)propyl, diethylaminomethyl, hydroxy, morpholinomethyl, methanesulphonylamino, oxopyrrolidinoethoxy, t-butoxycarbonylpiperazinomethyl, trifluoroethylamino, methylcarbamoylpropanoylaminomethyl, diethylaminoethoxymethyl, trifuloromethanesulfonylamino, piperazinocarbonyl, ethylaminoethoxymethyl, pyrrolidinoethoxymethyl, morpholinoethoxymethyl, piperidinoethoxy and dimethylaminoethoxy.

Other preferred compounds of this invention are those of the formula (I) wherein $R^3$ is 8-methyl-8-azabicyclo[3.2.1]oct-3-yl, 8-ethyl-8-azabicyclo[3.2.1]oct-3-yl or 8-formyl-8-azabicyclo[3.2.1]oct-3-yl; and $R^4$ is phenyl substituted al the 2-position with substituent selected from ethylenedioxyethyl, aminoethoxymethyl, aminoethoxy, aminopropoxy, aminopropoxymethyl, phenylthiomethyl, (dimethylamino)propyl, diethylaminomethyl, hydroxy, morpholinomethyl, methanesulphonylamino, oxopyrrolidinoethoxy, t-butoxycarbonylpiperazinomethyl, trifluoroethylamino, methylcarbamoylpropanoylaminomethyl, diethylaminoethoxymethyl, trifuloromethanesulfonylamino, piperazinocarbonyl, ethylaminoethoxymethyl, pyrrolidinoethoxymethyl, morpholinoethoxymethyl, piperidinoethoxy and dimethylaminoethoxy.

One embodiment of the present invention is directed to the above preferred compounds of the formula (I) wherein the 8-methyl-8-azabicyclo[3.2.1]oct-3-yl, 8-ethyl-8-azabicyclo[3.2.1]oct-3-yl or 8-formyl-8-azabicyclo[3.2.1]oct-3-yl group of $R^3$ is in the exo orientation.

One embodiment of the present invention is directed to the above preferred compounds of the formula (I) wherein the 8-methyl-8-azabicyclo[3.2.1]oct-3-yl, 8-ethyl-8-azabicyclo[3.2.1]oct-3-yl or 8-formyl-8-azabicyclo[3.2.1]oct-3-yl group of $R^3$ is in the endo orientation.

Examples of preferred compounds of the formula (I) of this invention are:

Dimethyl-2-(2-{2-[(2-aminoethoxy)methyl]phenyl}ethyl)-4-(2,6-dichlorophenyl)-6-{2-[4-(8-methyl-8-azabicyclo[3.2.1]oct-3-yl)-1-piperazinyl]-2-oxoethyl}-1,4-dihydro-3,5-pyridinedicarboxylate;

Dimethyl-2-{2-[2-(2-aminoethoxy)phenyl]ethyl}-4-(2,6-dichlorophenyl)-6-{2-[4-(8-methyl-8-azabicyclo[3.2.1]oct-3-yl)-1-piperazinyl]-2-oxoethyl}-1,4-dihydro-3,5-pyridinedicarboxylate;

Dimethyl-2-{2-[2-(3-aminopropoxy)phenyl]ethyl}-4-(2,6-dichlorophenyl)-6-{2-[4-(8-methyl-8-azabicyclo[3.2.1]oct-3-yl)-1-piperazinyl]-2-oxoethyl}-1,4-dihydro-3,5-pyridinedicarboxylate;

Dimethyl-2-(2-{2-[(3-aminopropoxy)methyl]phenyl}ethyl)-4-(2,6-dichlorophenyl)-6-{2-[4-(8-methyl-8-azabicyclo[3.2.1]oct-3-yl)-, 1-piperazinyl]-2-oxoethyl}-1,4-dihydro-3,5-pyridinedicarboxylate;

Dimethyl-4-(2,6-dichlorophenyl)-2-{2-[4-(8-methyl-8-azabicyclo[3.2.1]oct-3-yl)-1-piperazinyl]-2-oxoethyl}-6-{2-[(phenylsulfanyl)methyl]phenethyl}-1,4-dihydro-3,5-pyridinedicarboxylate;

Dimethyl-4-(2,6-dichlorophenyl)-2-(2-{2-[3-(dimethylamino)propyl]phenylethyl)-6-(2-[4-(8-methyl-8-azabicyclo[3,2,1]oct-3-yl)-1-piperazinyl]-2-oxoethyl}-1,4-dihydro-3,5-pyridinecarboxylate;

Dimethyl-4-(2,6-dichlorophenyl)-2-(2-{2-[(diethylamino)methyl]phenyl}ethyl)-6-{2-[4-(8-methyl-8-azabicyclo

[3.2.1]oct-3-yl]-1-piperazinyl]-2-oxoethyl}-1,4-dihydro-3,5-pyridinedicarboxylate;

Dimethyl-4-(2,6-dichlorophenyl)-2-[2-(2-hydroxyphenyl)ethyl]-6-{2-[4-(8-methyl-8-azabicyclo[3.2.1]oct-3-yl)-1-piperazinyl]-2-oxoethyl}-1,4-dihydro-3,5-pyridinedicarboxylate;

Dimethyl-4-(2,6-dichlorophenyl)-2-2-[4-(8-methyl-8-azabicyclo[3.2.1]oct-3-yl)-1-piperazinyl]-2-oxoethyl]-6-[2-[2-(4-morpholinylmethyl)phenyl]ethyl]-1,4-dihydro-3,5-pyridinedicarboxylate;

Dimethyl-4-(2,6-dichlorophenyl)-2-{2-[4-(8-methyl-8-azabicyclo[3.2.1]oct-3-yl)-1-piperazinyl]-2-oxoethyl}-6-(2-{2-[(methylsulfonyl)aminophenyl}ethyl)-1,4-dihydro-3,5-pyridinedicarboxylate;

Dimethyl-4-(2,6-dichlorophenyl)-2-(2-[4-(8-methyl-8-azabicyclo[3.2.1]oct-3-yl)-1-piperazinyl]-2-oxoethyl}-6-(2-{2-[2-(2-oxo-1-pyrrolidinyl)ethoxy]phenyl}ethyl)-1,4-dihydro-3,5-pyridinedicarboxylate;

Dimethyl-2-[2-(2-{[4-(tert-butoxycarbonyl)-1-piperazinyl]methyl}phenyl)ethyl]-4-(2,6-dichlorophenyl)-6-{2-[4-(8-methyl-8-azabicyclo[3.2.1]oct-3-yl)-1-piperazinyl]-2-oxoethyl}-1,4-dihydro-3,5-pyridinedicarboxylate;

Dimethyl-4-(2,6-dichlorophenyl)-2-{2-[4-(8-methyl-8-azabicyclo[3.2.1]oct-3-yl)-1-piperazinyl]-2-oxoethyl}-6-(2-{2-[(2,2,2-trifluoroethyl)amino]phenyl}ethyl)-1,4-dihydro-3,5-pyridinedicarboxylate;

Dimethyl-4-(2,6-dichlorophenyl)-2-{2-[2-({[4-(methylamino)-4-oxobutanoyl]amino}methyl)phenyl]ethyl}-6-{2-[4-(8-methyl-8-azabicyclo[3.2.1]oct-3-yl)-1-piperazinyl]-2-oxoethyl}-1,4-dihydro-3,5-pyridinedicarboxylate;

Dimethyl-4-(2,6-dichlorophenyl)-2-[2-(2-{[2-(diethylamino)ethoxy]methyl}phenyl)ethyl]-6-{2-[4-(8-methyl-8-azabicyclo[3.2.1]oct-3-yl)-1-piperazinyl]-2-oxoethyl}-1,4-dihydro-3,5-pyridinedicarboxylate;

4-(2,6-Dichloro-phenyl)-2-{2-[2-(2-diethylamino-ethoxymethyl)-phenyl]-ethyl}-6-{2-[4-(8-methyl-8-azabicyclo[3.2.1]oct-3-yl)-piperazin-1-yl]-2-oxo-ethyl}-1,4-dihydro-pyridine-3,5-dicarboxylic acid dimethyl ester;

Dimethyl-4-(2,6-dichlorophenyl)-2-{2-[4-(8-methyl-8-azabicyclo[3.2.1]oct-3-yl)-1-piperazinyl]-2-oxoethyl}-6-[2-(2-{[(trifluoromethyl)sulfonyl]amino}phenyl)ethyl]-1,4-dihydro-3,5-pyridinedicarboxylate;

Dimethyl-4-(2,6-dichlorophenyl)-2-{2-[4-(8-methyl-8-azabicyclo[3.2.1]oct-3-yl)-1-piperazinyl]-2-oxoethyl}-6-(2-[2-(1-piperazinylcarbonyl)phenyl]ethyl}-1,4-dihydro-3,5-pyridinedicarboxylate;

Dimethyl-4-(2,6-dichlorophenyl)-2-[2-(2-{[2-(ethylamino)ethoxy]methyl}phenyl)ethyl]-6-{2-[4-(8-methyl-8-azabicyclo[3.2.1]oct-3-yl)-1-piperazinyl]-2-oxoethyl}-1,4-dihydro-3,5-pyridinedicarboxylate;

Dimethyl-4-(2,6-dichlorophenyl)-2-[2-(2-{[2-pyrrolidinoethoxy]methyl}phenyl)ethyl]-6-{2-[4-(8-methyl-8-azabicyclo[3.2.1]oct-3-yl)-1-piperazinyl]-2-oxoethyl}-1,4-dihydro-3,5-pyridinedicarboxylate;

Dimethyl-4-(2,6-dichlorophenyl)-2-[2-(2-{[2-morpholinoethoxy]methyl}phenyl)ethyl]-6-{2-[4-(8-methyl-8-azabicyclo[3.2.1]oct-3-yl)-1-piperazinyl]-2-oxoethyl}-1,4-dihydro-3,5-pyridinedicarboxylate;

Dimethyl-4-(2,6-dichlorophenyl)-2-{2-[4-(8-methyl-8-azabicyclo[3.2.1]oct-3-yl)-1-piperazinyl]-2-oxoethyl}-6-[2-(2-{[2-(1-pyrrolidinyl)ethoxy]methyl}phenyl)ethyl]-1,4-dihydro-3,5-pyridinedicarboxylate;

Dimethyl-4-(2,6-dichlorophenyl)-2-{2-[4-(8-methyl-8-azabicyclo[3.2.1]oct-3-yl)-1-piperazinyl]-2-oxoethyl}-6-[2-(2-{[2-(4-morpholinyl)ethoxy]methyl}phenyl)ethyl]-1,4-dihydro-3,5-pyridinedicarboxylate;

and the pharmaceutically acceptable salts thereof.

Examples of more preferred compounds of the formula (I) of this invention are:

Dimethyl-2-(2-{2-[(2-aminoethoxy)methyl]phenyl}ethyl)-4-(2,6-dichlorophenyl)-6-{2-[4-(8-methyl-8-azabicyclo[3.2.1]oct-3-yl)-1-piperazinyl]-2-oxoethyl}-1,4-dihydro-3,5-pyridinedicarboxylate;

Dimethyl-4-(2,6-dichlorophenyl)-2-(2-{2-[3-(dimethylamino)propyl]phenyl}ethyl)-6-{2-[4-(8-methyl-8-azabicyclo[3,2,1]oct-3-yl)-1-piperazinyl]-2-oxoethyl}-1,4-dihydro-3,5-pyridinecarboxylate;

Dimethyl-4-(2,6-dichlorophenyl)-2-(2-(2-[(diethylamino)methyl]phenylethyl)-6-{2-[4-(8-methyl-8-azabicyclo[3.2.1]oct-3-yl)-1-piperazinyl]-2-oxoethyl}-1,4-dihydro-3,5-pyridinedicarboxylate;

Dimethyl-4-(2,6-dichlorophenyl)-2-{2-[4-(8-methyl-8-azabicyclo[3.2.1]oct-3-yl)-1-piperazinyl]-2-oxoethyl}-6-(2-{2-[(methylsulfonyl)amino]phenylethyl)-1,4-dihydro-3,5-pyridinedicarboxylate;

Dimethyl-4-(2,6-dichlorophenyl)-2-{2-[4-(8-methyl-8-azabicyclo[3.2.1]oct-3-yl)-1-piperazinyl]-2-oxoethyl}-6-(2-{2-[2-(2-oxo-1-pyrrolidinyl)ethoxy]phenyl}ethyl)-1,4-dihydro-3,5-pyridinedicarboxylate;

Dimethyl-4-(2,6-dichlorophenyl)-2-{2-[2-(({[4-(methylamino)-4-oxobutanoyl]amino}methyl)phenyl]ethyl}-6-{2-[4-(8-methyl-8-azabicyclo[3.2.1]oct-3-yl)-1-piperazinyl]-2-oxoethyl}-1,4-dihydro-3,5-pyridinedicarboxylate;

Dimethyl-4-(2,6-dichlorophenyl)-2-[2-(2-{[2-(diethylamino)ethoxy]methyl}phenyl)ethyl]-6-{2-[4-(8-methyl-8-azabicyclo[3.2.1]oct-3-yl)-1-piperazinyl]-2-oxoethyl}-1,4-dihydro-3,5-pyridinedicarboxylate;

4-(2,6-Dichloro-phenyl)-2-{2-[2-(2-diethylamino-ethoxymethyl)-phenyl]-ethyl}-6-{2-[4-(8-methyl-8-azabicyclo[3.2.1]oct-3-yl)-piperazin-1-yl]-2-oxo-ethyl}-1,4-dihydro-pyridine-3,5-dicarboxylic acid dimethyl ester;

Dimethyl-4-(2,6-dichlorophenyl)-2-{2-[4-(8-methyl-8-azabicyclo[3.2.1]oct-3-yl)-1-piperazinyl]-2-oxoethyl}-6-{2-[2-(1-piperazinylcarbonyl)phenyl]ethyl}-1,4-dihydro-3,5-pyridinedicarboxylate;

and the pharmaceutically acceptable salts thereof.

An example of a preferred compound of the formula (I) of this invention is (4R)-(−)-4-(2,6-Dichloro-phenyl)-2-(2-[2-(2-diethylamino-ethoxymethyl)-phenyl]-ethyl}-6-{2-[4-(exo)-(8-methyl-8-aza-bicyclo[3.2.1]oct-3-yl)-piperazin-1-yl]-2-oxo-ethyl}-1,4-dihydro-pyridine-3,5-dicarboxylic acid dimethyl ester, and the pharmaceutically acceptable salts thereof.

Another example of a preferred compound of the formula (I) of this invention is (4R)-(−)-4-(2,6-Dichloro-phenyl)-2-{2-[2-(2-diethylamino-ethoxymethyl)-phenyl]-ethyl)-6-{2-[4-(exo)-(8-methyl-8-aza-bicyclo[3.2.1]oct-3-yl)-piperazin-1-yl]-2-oxo-ethyl}-1,4-dihydro-pyridine-3,5-dicarboxylic acid dimethyl ester, monosuccinic acid.

Preferable compounds of this invention have potent $B_2$ antagonistic activity without metabolic liability or drug—drug interactions, especially inhibition of P-450 isozymes such as CYP3A4.

The compounds of formula (1) of the present invention exhibit significant bradykinin receptor-binding activity, and thus, the compounds of formula (I) of the present invention are readily adapted to therapeutic use as bradykinin antagonists for the control and/or treatment of a wide variety of clinical conditions in mammals, including humans. Such conditions include inflammation, cardiovascular disease, pain, common cold, allergies, asthma, pancreatitis, burns, virus infection, head injury, multiple trauma and the like.

As discussed above, the compounds of formula (I) of this invention have an antagonistic action towards bradykinin and are thus useful in therapeutics, particularly for the treatment of inflammation and inflammatory disorders, rheumatoid arthritis, cystitis, post-traumatic and post ischemic cerebral eczema, liver cirrhosis and other liver/kidney diseases, Alzheimer's disease, cardiovascular disease, pain, common cold, allergies and immunology/allergy disorders, asthma, pancreatitis, burns and other skin disorders, virus infection and other infectious diseases, head injury, multiple trauma, rhinitis, hepatorenal failure, diabetes and other metabolic diseases, metastasis, pancreatitis, neovascularization, corneal haze, glaucoma, ocular pain, ocular hypertension and other eye diseases, angio edema or the like in mammalian, especially humans.

As discussed above, the compounds of formula (I) of this invention have an antagonistic action towards bradykinin and are thus useful in therapeutics, particularly for the treatment of Huntington's disease, Parkinson's disease and other central nervous system disorders, Amyotrophic lateral sclerosis, multiple sclerosis, stroke, head trauma, post-surgical brain edema, brain edema (general), cytotoxic brain edema (such as that associated with brain tumors, stroke, head trauma, etc.), brain edema associated with metabolic diseases (renal failure, pediatric metabolic diseases, etc.), rheumatoid arthritis, osteoarthritis, migraine, neuropathic pain, pruritis, brain tumor and other cancers, pseudotumor cerebri, glaucoma, hydrocephalus, spinal cord trauma, spinal cord edema, neurodegenerative diseases, respiratory diseases, diuresis, natriuresis calciuresis, COPD (chronic obstructive pulmonary disease), post-traumatic brain injury, itching, sepsis or the like in mammalian, especially humans.

The present invention relates to a pharmaceutical composition for the treatment of disease conditions mediated by bradykinin, in a mammalian subject, which comprises a therapeutically effective amount of a compound of formula (I), or a pharmaceutically acceptable salt thereof, and a pharmaceutically acceptable carrier.

The present invention also relates to a pharmaceutical composition for the treatment of inflammation, rheumatoid arthritis, cystitis, post-traumatic and post ischemic cerebral edema, liver cirrhosis, Alzheimer's disease, cardiovascular disease, pain, common cold, allergies, asthma, pancreatitis, burns, virus infection, head injury, multiple trauma, rhinitis, hepatorenal failure, diabetes, metastasis, pancreatitis, neovascularization, corneal haze, glaucoma, ocular pain, ocular hypertension, angio edema or the like, which comprises a therapeutically effective amount of a compound of formula (I), or a pharmaceutically acceptable salt thereof, and a pharmaceutically acceptable carrier.

The present invention also relates to a pharmaceutical composition for the treatment of Amyotrophic lateral sclerosis, Huntington's disease, Parkinson's disease, Multiple sclerosis, Stroke, head trauma, Post-surgical brain edema, Brain edema (general), Cytotoxic brain edema (such as that associated with brain tumors, stroke, head trauma, etc.), Brain edema associated with metabolic diseases (renal failure, pediatric metabolic diseases, etc.), Rheumatoid arthritis, Osteoarthritis, Migraine, Neuropathic Pain, Pruritis, Brain Tumor, Pseudotumor cerebri, Glaucoma, Hydrocephalus, Spinal cord trauma, Spinal cord edema, neurodegenerative diseases, respiratory diseases, diuresis, natriuresis calciuresis, COPD (chronic obstructive pulmonary disease), post-traumatic brain injury, itching or Sepsis, which comprises a therapeutically effective amount of a compound of formula (I), or a pharmaceutically acceptable salt thereof, and a pharmaceutically acceptable carrier.

Preferably, the compounds of the present invention may be used to treat inflammation, asthma, allergic rhinitis and pain. More preferably, the compounds of the present invention may be used to treat inflammation, asthma and allergic rhinitis. Most preferably, the compounds of the present invention may be used to treat inflammation and allergic rhinitis.

The present invention relates to a method for the treatment of disease conditions mediated by bradykinin, in a mammalian subject, which comprises administering to said subject a therapeutically effective amount of a compound of formula (I) or a pharmaceutically acceptable salt thereof.

The present invention also relates to a method for the treatment of inflammation, rheumatoid arthritis, cystitis, post-traumatic and post ischemic cerebral edema, liver cirrhosis, Alzheimer's disease, cardiovascular disease, pain, common cold, allergies, asthma, pancreatitis, burns, virus infection, head injury, multiple trauma, rhinitis, hepatorenal failure, diabetes, metastasis, pancreatitis, neovascularization, corneal haze, glaucoma, ocular pain, ocular hypertension, angio edema or the like, in a mammalian subject, which comprises administering to said subject a therapeutically effective amount of a compound of formula (I) or a pharmaceutically acceptable salt thereof.

The present invention also relates to a method for the treatment of Amyotrophic lateral sclerosis, Huntington's disease, Parkinson's disease, Multiple sclerosis, Stroke, head trauma, Post-surgical brain edema, Brain edema (general), Cytotoxic brain edema (such as that associated with brain tumors, stroke, head trauma, etc.), Brain edema associated with metabolic diseases (renal failure, pediatric metabolic diseases, etc.), Rheumatoid arthritis, Osteoarthritis, Migraine, Neuropathic Pain, Pruritis, Brain Tumor, Pseudotumor cerebri, Glaucoma, Hydrocephalus, Spinal cord trauma, Spinal cord edema, neurodegenerative diseases, respiratory diseases, diuresis, natriuresis calciuresis, COPD (chronic obstructive pulmonary disease), post-traumatic brain injury, itching or Sespis, in a mammalian subject, which comprises administering to said subject a therapeutically effective amount of a compound of formula (I) or a pharmaceutically acceptable salt thereof.

The present invention also relates to a pharmaceutical formulation comprising a compound of formula (I), a pharmaceutically acceptable carrier and, optionally, one or more other pharmacologically active agents.

The present invention also includes isotopically labeled compounds, which are identical to those recited in formula (I), but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of formula (I) of this invention and prodrugs thereof can generally be prepared by carrying out the procedures disclosed in the Schemes and/or in the Examples and Preparations below, by substituting a readily available isotopically labeled reagent for a non-isotopically labeled reagent.

This invention also encompasses pharmaceutical compositions containing prodrugs of compounds of the formula (I). Compounds of formula (I) having free amino, amido, hydroxy or carboxylic groups can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of formula (I). The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Prodrugs also include compounds wherein carbonates, carbamates, amides and alkyl esters which are covalently bonded to the above substituents of formula (I) through the carbonyl carbon prodrug side chain.

The present invention also encompasses sustained release compositions.

The term "treating", as used herein, refers to reversing, alleviating, inhibiting the progress of, or preventing the disorder or condition to which such term applies, or one or more symptoms of such disorder or condition. The term "treatment", as used herein, refers to the act of treating, as "treating" is defined immediately above.

"Inflammatory disorders," as used herein, refers to disorders such as rheumatoid arthritis, ankylosing spondylitis, psoriatic arthritis, psoriasis, chondrocalcinosis, gout, inflammatory bowel disease, ulcerative colitis, Crohn's disease and cachexia.

"Immunology/allergy disorders," as used herein, refers to disorders such as organ transplant toxicity, allergic reactions, allergic contact hypersensitivity, autoimmune disorders such as those disorders associated with granulomatous inflammation/tissue remodeling (such as asthma), immunosuppression and sarcoid.

"Infectious diseases," including those mediated by viruses, bacteria, fungi or mycobacterial infection, as used herein, refers to disorders such as septic arthritis, AIDS, fever, Prion diseases, myasthenia gravis, Malaria, sepsis, hemodynamic shock, and septic shock.

"Respiratory diseases," as used herein, refers to disorders such as chronic obstructive pulmonary disease (including emphysema), acute respiratory distress syndrome, asthma, hyperoxic alveolar injury and idiopathic pulmonary fibrosis and other fibrotic lung diseases. It also includes obstructive or inflammatory airways diseases of whatever type, etiology, or pathogenesis; or an obstructive or inflammatory airways disease that is a member selected from the group consisting of asthma; pneumoconiosis; chronic eosinophilic pneumonia; chronic obstructive pulmonary disease (COPD); COPD that includes chronic bronchitis, pulmonary emphysema or dyspnea associated therewith; COPD that is characterized by irreversible, progressive airways obstruction; acute respiratory distress syndrome (AIDS); and exacerbation of airways hyper-reactivity consequent to other drug therapy.

Asthma includes asthma of whatever type, etiology, or pathogenesis; or asthma that is a member selected from the group consisting of atopic asthma; non-atopic asthma; allergic asthma; atopic, bronchial, IgE-mediated asthma; bronchial asthma; essential asthma; true asthma; intrinsic asthma caused by pathiophysiologic disturbances; extrinsic asthma caused by environmental factors; essential asthma of unknown or inapparent cause; non-atopic asthma; bronchitic asthma; emphysematous asthma; exercise-induced asthma; occupational asthma; infective asthma caused by bacterial, fungal, protozoal, or viral infection; non-allergic asthma; incipient asthma; and wheezy infant syndrome.

"Cardiovascular diseases," as used herein, refers to disorders such as atherosclerosis including atherosclerotic plaque rupture; aortic aneurysm including abdominal aortic aneurysm and brain aortic aneurysm; congestive heart failure; myocardial and cerebral infarction; stroke; cerebral ischemia; coagulation and acute phase response; left ventricular dilation; post ischemic reperfusion injury; angiofibromas; hemangiomas; and restenosis.

"Eye diseases," as used herein, refers to disorders such as aberrant angiogenesis, ocular angiogenesis, ocular inflammation, keratoconus, Sjogren's syndrome, myopia, ocular tumors, corneal graft rejection, corneal injury, neovascular glaucoma, corneal ulceration, corneal scarring, macular degeneration (including Age Related Macular Degeneration (ARMD) including both wet and dry forms), proliferative vitreoretinopathy and retinopathy of prematurity.

"Metabolic diseases," as used herein, refers to disorders such as diabetes (including non-insulin dependent diabetes mellitus, diabetic retinopathy, insulin resistance and diabetic ulceration).

"Central Nervous System" (CNS) disorders, as used herein, refers to disorders such as head trauma, spinal cord injury, inflammatory diseases of the central nervous system, neuro-degenerative disorders (acute and chronic), Alzheimer's disease, demyelinating diseases of the nervous system, Huntington's disease, Parkinson's disease, peripheral neuropathy, pain, cerebral amyloid angiopathy, nootropic or cognition enhancement, amyotrophic lateral sclerosis, multiple sclerosis, migraine, depression and anorexia.

"Liver/Kidney diseases," as used herein, refers to disorders such as nephrotic syndromes, including glomerulonephritis and glomerular disease of the kidney, proteinuria, cirrhosis of the liver and interstitial nephrilis.

"Skin disorders," as used herein, refers to disorders such as skin aging, pressure sores, psoriasis, eczema, dermatitis, radiation damage, tissue ulceration, decubital ulcers, epidermolysis bullosa, abnormal wound healing (topical and oral formulations), burns and scleritis.

"Cancers," as used herein, refers to disorders such as solid tumor cancer including colon cancer, breast cancer, lung cancer and prostrate cancer, tumor invasion, tumor growth, tumor metastasis, cancers of the oral cavity and pharynx (lip, tongue, mouth, pharynx), esophagus, stomach, small intestine, large intestine, rectum, liver and biliary passages, pancreas, larynx, lung, bone, connective tissue, skin, cervix uteri, corpus endometrium, ovary, testis, bladder, kidney, other urinary tissues, eye, brain and central nervous system, thyroid and other endocrine gland, Hodgkin's disease, non-Hodgkin's lymphomas, multiple myeloma, and hematopoietic malignancies including leukemias and lymphomas including lymphocytic, granulocytic and monocytic.

Rhinitis includes seasonal allergic rhinitis; or perennial allergic rhinitis; or sinusitis of whatever type, etiology, or pathogenesis; or sinusitis that is a member selected from the group consisting of purulent or nonpurulent sinusitis; acute or chronic sinusitis; and ethmoid, frontal, maxillary, or sphenoid sinusitis.

Rheumatoid arthritis includes rheumatoid arthritis of whatever type, etiology, or pathogenesis; or rheumatoid arthritis that is a member selected from the group consisting of acute arthritis; acute gouty arthritis; chronic inflammatory arthritis; degenerative arthritis; infectious arthritis; Lyme arthritis; proliferative arthritis; psoriatic arthritis; and vertebral arthritis.

One of ordinary skill in the art will appreciate that the compounds of the present invention are useful in treating a diverse array of diseases. One of ordinary skill in the art will also appreciate that when using the compounds of the present invention in the treatment of a specific disease, the compounds of the present invention may be combined with various existing therapeutic agents used for that disease.

The compounds of formula (I) of the present invention may be expected to exhibit more effective therapeutic effects when used in combination with an $H_1$-antagonist.

Thus, the present invention also relates to a pharmaceutical composition for the treatment of inflammation, rheumatoid arthritis, cystitis, post-traumatic and post ischemic cerebral edema, liver cirrhosis, Alzheimer's disease, cardiovascular disease, pain, common cold, allergies, asthma, pancreatitis, burns, virus infection, head injury, multiple trauma, rhinitis, hepatorenal failure, diabetes, metastasis, cystitis, pancreatitis, amyotrophic lateral sclerosis, Hunting-ton's disease, Parkinson's disease, multiple sclerosis, stroke, head trauma, post-surgical brain edema, brain edema (general), cytotoxic brain edema (such as that associated with brain tumors, stroke, head trauma, etc.), brain edema associated with metabolic diseases (renal failure, pediatric metabolic diseases, etc.), rheumatoid arthritis, osteoarthritis, migraine, neuropathic pain, pruritus, brain tumor, pseudotumor cerebri, glaucoma, hydrocephalus, spinal cord trauma, spinal cord edema, neurodegenerative diseases, respiratory diseases, diuresis, natriuresis calciuresis, COPD (chronic obstructive pulmonary disease), post-traumatic brain injury, itching, sepsis, or the like in a mammal, including a human, which comprises a therapeutically effective amount of a compound of formula (I) or pharmaceutically acceptable salt thereof and an Hl-antagonist or pharmaceutically acceptable salt thereof, and a pharmaceutically acceptable carrier.

The combination of a compound of formula (I) of the present invention with an anti-histamine ($H_1$ antagonist) is particularly favored for use in the prophylaxis and treatment of asthma and rhinitis. Examples of anti-histamines are chlorpheniramine, brompheniramine, clemastine, ketotifen, azatadine, loratadine, terfenadine, cetirizine, astemizole, tazifylline, levocabastine, diphenhydramine, temelastine, etolotifen, acrivastine, azelastine, ebastine, mequitazine, KA-398, FK-613, mizolastine, MDL-103896, levocetirizine, mometasone furoate, DF-1111301, KC-11404, carebastine, ramatroban, desloratadine, noberastine, selenotifen, alinastine, E-4716, efletirizine, tritoqualine, norastemizole, ZCR-2060, WY-49051, KAA-276, VUF-K-9015, tagorizine, KC-11425, epinastine, MDL-28163 terfenadine, HSR-609, acrivastine and BMY-25368.

The compounds of the invention may advantageously be employed in combination with one or more other therapeutic agents, including an antibiotic, anti-fungal, or anti-viral agent, an anti-histamine, a non-steroidal anti-inflammatory drug or disease modifying anti-rheumatic drug.

For the treatment of rheumatoid arthritis, the compounds of the present invention may be combined with agents such as TNF-α inhibitors such as anti-TNF monoclonal antibodies (such as Remicade, CDP-870 and $D_2E_7$) and TNF receptor immunoglobulin molecules (such as Enbrel®), COX-2 inhibitors (such as meloxicam, celecoxib, rofecoxib, valdecoxib and etoricoxib) low dose methotrexate, leflunomide, hydroxychloroquine, d-penicillamine, auranofin or parenteral or oral gold.

The compounds of the present invention can also be used in combination with existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib, valdecoxib, rofecoxib and etoricoxib, analgesics and intraarticular therapies such as corticosteroids and hyaluronic acids such as hyalgan and synvisc.

The compounds of the present invention may also be used in combination with anticancer agents such as endostatin and angiostatin or cytotoxic drugs such as adriamycin, daunomycin, cis-platinum, etoposide, taxol, taxotere and alkaloids, such as vincristine, farnesyl transferase inhibitors, VegF inhibitors, and antimetabolites such as methotrexate.

The compounds of the present invention may also be used in combination with antiviral agents such as Viracept, AZT, aciclovir and famciclovir, and antisepsis compounds such as Zovant, tifacogin, NOX-100 and 13R270773.

The compounds of the present invention may also be used in combination with cardiovascular agents such as calcium channel blockers, lipid lowering agents such as statins, fibrates, beta-blockers, Ace inhibitors, Angiotensin-2 receptor antagonists and platelet aggregation inhibitors.

The compounds of the present invention may also be used in combination with CNS agents such as antidepressants (such as sertraline), anti-Parkinsonian drugs (such as deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase), and anti-Alzheimer's drugs such as donepezil, tacrine, COX-2 inhibitors, propentofylline or metryfonate.

The compounds of the present invention may also be used in combination with osteoporosis agents such as roloxifene, droloxifene, lasofoxifene or fosomax and immunosuppressant agents such as FK-506 and rapamycin.

The present invention still further relates to the combination of a compound of formula (I) together with one or more members selected from the group consisting of the following: (a) leukotriene biosynthesis inhibitors: 5-lipoxygenase (5-LO) inhibitors and 5-lipoxygenase activating protein (FLAP) antagonists selected from the group consisting of zileuton; ABT-761; fenleuton; tepoxalin; Abbott-79175; Abbott-85761; N-(5-substituted)-thiophene-2alkylsulfonamides of Formula (5.2.8); 2,6-di-tert-butylphenol hydrazones of Formula (5.2.10); the class of methoxytetrahydropyrans which includes Zeneca ZD-2138 of Formula (5.2.11); the compound SB-210661 of Formula (5.2.12) and the class to which it belongs; the class of pyridinyl-substituted 2-cyanonaphthalene compounds to which L-739,010 belongs; the class of 2-cyanoquinoline compounds to which L-746,530 belongs; the classes of indole and quinoline compounds to which MK-591,, MK-886, and BAYx 1005 belong; (b) receptor antagonists for leukotrienes $LTB_4$, $LTC_4$, $LTD_4$, and $LTE_4$ selected from the group consisting of the phenothiazin-3-one class of compounds to which L-651,392 belongs; the class of amidino compounds to which CGS-25019c belongs; the class of benzoxaolamines to which ontazolast belongs; the class of benzenacarboximidamides to which BIIL 2841260 belongs; and the classes of compounds to which zafirlukast, ablukast, montelukast, praniukast, verlukast (MK-679), RG-12525, Ro-2459913, iralukast (CGP 45715A), and BAYx 7195 belong; (c) PDE4 inhibitors including inhibitors of the isoform PDE4D; (d) 5-Lipoxygenase (5-LO) inhibitors; or 5-lipoxygenase activating protein (FLAP) antagonists; (e) dual inhibitors of 5-lipoxygenase (5-LO) and antagonists of platelet activating factor (PAF); (f) leukotriene antagonists (LTRAs) including antagonists of $LTB_4$, $LTC_4$, $LTD_4$, and $LTE_4$; (g) antihistaminic $H_1$ receptor antagonists including cetirizine, loratadine, desloratadine, fexofenadine, astemizole, azelastine, and chlorpheniramine; (h) gastroprotective $H_2$ receptor antagonists; (i) $α_1$- and $α_2$-adrenoceptor agonist vasoconstrictor sympathomimetic agents administered orally or topically for decongestant use, including propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride; (j) $α_1$- and $α_2$-adrenoceptor agonists in combination with inhibitors of 5-lipoxygenase (5-LO); (k) anticholinergic agents including ipratropium bromide; tiotropium bromide; oxitropium bromide; pirenzepine; and telenzepine; (I) [3- to $β_4$-adrenoceptor agonists including metaproterenol, isoproterenol, isoprenaline, albuterol, salbutamol, formoterol, salmeterol, terbutaline, orciprenaline, bitolterol mesylate, and pirbuterol; (m) methylxanthanines including theophylline and aminophylline; (n) sodium cromoglycate; (o) muscarinic receptor (M1, M2, and M3) antagonists; (p) COX-1 inhibitors (NSAIDs); COX-2 selective inhibitors including rofecoxib; and nitric oxide NSAIDs; (q) insulin-like growth factor type I (IGF-1) mimetics; (r) ciclesonide; (s) inhaled glucocorticoids with reduced systemic side effects, including prednisone, prednisolone, flunisolide, triamcinolone acetonide, beclomethasone dipropionate, budesonide, fluticasone propionate, and mometasone furoate; (t) tryptase inhibitors; (u) platelet activating factor (PAF) antagonists; (v) monoclonal antibodies active against endogenous inflammatory entities; (w) IPL 576; (x) anti-tumor necrosis factor (TNFα) agents including Etanercept, Infliximab, and D2E7; (y) DMARDs including Leflunomide; (z) TCR peptides; (aa) interleukin converting enzyme (ICE) inhibitors; (bb) IMPDH inhibitors; (cc) adhesion molecule inhibitors including VLA-4 antagonists; (dd) cathepsins; (ee) MAP kinase inhibitors; (ff) glucose-6 phosphate dehydrogenase inhibitors; (hh) gold in the form of an aurothio group together with various hydrophilic groups; (ii) immunosuppressive agents, e.g., cyclosporine, azathioprine, and methotrexate; (jj) anti-gout agents, e.g., colchicine; (kk) xanthine oxidase inhibitors, e.g., allopurinol; (ll) uricosuric agents, e.g., probenecid, sulfinpyrazone, and benzbromarone; (mm) antineoplastic agents, especially antimitotic drugs including the vinca alkaloids such as vinblastine and vincristine; (nn) growth hormone secretagogues; (oo) inhibitors of matrix metalloproteases (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11); (pp) transforming growth factor (TGFP); (qq) platelet-derived growth factor (PDGF); (rr) fibroblast growth factor, e.g., basic fibroblast growth factor (bFGF); (ss) granulocyte macrophage colony stimulating factor (GM-CSF); (tt) capsaicin cream; (uu) Tachykinin NK, and $NK_3$ receptor antagonists selected from the group consisting of NKP-608C; SB-233412 (talnetant); and D-4418; and (vv) elastase inhibitors selected from the group consisting of UT-77 and ZD-0892.

The present invention also relates to processes for preparing the compounds of formula (I) and to intermediates used in such processes.

Thus, the present invention also relates to a compound of the formula

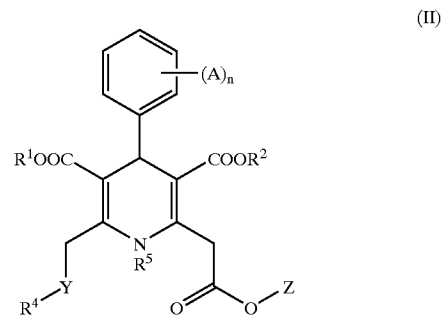

(II)

wherein

A is independently halo;

Y is —$(CH_2)_m$—, —C(O)— or —S(O)—;

Z is hydrogen or $C_{1-4}$ alkyl;

$R^1$ and $R^2$ are independently $C_{1-4}$ alkyl;

$R^4$ is phenyl substituted at 2-position with substituent selected from (a) $C_{1-4}$ alkyl substituted with one, two or three substituents independently selected from amino, amino-$C_{2-4}$ alkoxy, phenylthio, $C_{1-4}$ alkyl-phenylthio, di-$C_{1-4}$ alkylamino-$C_{2-4}$ alkoxy, $C_{1-4}$ alkylamino-$C_{2-4}$ alkoxy, $C_{1-4}$ alkylamino, di-$C_{1-4}$ alkylamino, hydroxy, $C_{1-4}$ alkoxy, piperazinyl, oxopyrrolidinyl, pyrrolidinyl, $C_{2-4}$ alkylenedioxy, $C_1$ acyloxy, oxo, morpholino, $C_{1-4}$ alkylaminocarbonyl-$C_{1-6}$ acylamino, $C_{1-4}$ alkoxycarbonyl-$C_{1-6}$ acylamino, $C_{1-4}$ alkoxycarbonylpiperazinyl, Cl 6 acylpiperaizinyl, $C_{1-4}$ alkylthio, heterocyclic-$C_{1-4}$ alkoxy, (di-$C_{1-4}$ alkylamino)($C_{3-7}$ cycloalkyl)$C_{2-4}$ alkoxy, ($C_{1-4}$ alkylamino)($C_{3-7}$ cycloalkyl)$C_{2-4}$ alkoxy and (amino)($C_{3-7}$ cycloalkyl)$C_2A$ alkoxy;

(b) $C_{5-7}$ alkyl optionally substituted with one, two or three substituents independently selected from amino, amino-$C_{2-4}$ alkoxy, phenylthio, $C_{1-4}$ alkyl-phenylthio, di-$C_{1-4}$ alkylamino-$C_{2-4}$ alkoxy, $C_{1-4}$ alkylainino-$C_{2-4}$ alkoxy, $C_{1-4}$ alkylamino, di-$C_{1-4}$ alkylamino, hydroxy, $C_{1-4}$ alkoxy, piperazinyl, oxopyrrolidinyl, pyrrolidinyl, $C_{2-4}$ alkylenedioxy, $C_{1-6}$ acyloxy, oxo, morpholino, $C_{1-6}$ alkylaminocarbonyl-$C_{1-6}$ acylamino, $C_{1-4}$ alkoxycarbonyl-$C_{1-6}$ acylamino, $C_{1-4}$ alkoxycarbonylpiperazinyl, $C_{1-6}$ acylpiperazinyl, $C_{1-4}$ alkylthio, heterocyclic-$C_{1-4}$ alkoxy, (di-$C_{1-4}$ alkylamino)($C_{3-7}$cycloalkyl)$C_{2-4}$ allcoxy, ($C_{1-4}$ alkylamino)($C_{3-7}$ cycloalkyl)$C_{2-4}$ alkoxy and (amino)($C_{3-7}$ cycloalkyl)$C_{2-4}$ alkoxy;

(c) $C_{1-4}$ alkoxy or $C_{1-4}$ alkylthio, the $C_{1-4}$ alkoxy or $C_{1-4}$ alkylthio being substituted with one, two or three substituents independently selected from amino, amino-$C_{2-4}$ alkoxy, phenylthio, $C_{1-4}$ alkyl-phenylthio, di-$C_{1-4}$ alkylamino-$C_{2-4}$ alkoxy, $C_{1-4}$ alkylamino-$C_{2-4}$ alkoxy, $C_{1-4}$ alkylamino, di-$C_{1-4}$ alkylamino, hydroxy, $C_{1-4}$ alkoxy, piperazinyl, oxopyrrolidinyl, pyrrolidinyl, $C_{2-4}$ alkylenedioxy, $C_{1-6}$ acyloxy, oxo, morpholino, $C_{1-4}$ alkylaminocarbonyl-$C_{1-6}$ acylamino, $C_{1-4}$ alkoxycarbonyl-$C_{1-6}$ acylamino, $C_{1-4}$ alkoxycarbonylpiperazinyl, $C_{1-6}$ acylpiperazinyl, $C_{1-4}$alkylthio, heterocyclic-$C_{1-4}$ alkoxy, (di-ClA alkylamino)($C_{3-7}$ cycloalkyl)$C_{2-4}$ alkoxy, ($C_{1-4}$ alkylamino)($C_{3-7}$ cycloalkyl)($C_{2-4}$ alkoxy and (amino)($C_{3-7}$cycloalkyl)$C_{2-4}$ alkoxy;

(d) $C_{5-7}$ alkoxy or $C_{5-7}$ alkylthio, the $C_{5-7}$ alkoxy or $C_{5-7}$ alkylthio being optionally substituted with one, two or three substituents independently selected from amino, amino-$C_{2-4}$ alkoxy, phenylthio, $C_{1-4}$ alkyl-phenylthio, di-$C_{1-4}$ alkylamino-$C_{2-4}$ alkoxy, $C_{1-4}$ alkylamino-$C_{2-4}$ alkoxy, $C_{1-4}$ alkylamino, di-$C_{1-4}$ alkylamino, hydroxy, $C_{1-4}$ alkoxy, piperazinyl, oxopyrrolidinyl, pyrrolidinyl, $C_{2-4}$ alkylenedioxy, $C_{1-6}$ acyloxy, oxo, morpholino, $C_{1-4}$ alkylaminocarbonyl-$C_{1-6}$ acylamino, $C_{1-4}$ alkoxycarbonyl-$C_{1-6}$ acylamino, $C_{1-4}$ alkoxycarbonylpiperazinyl, $C_{1-6}$ acylpiperazinyl, $C_{1-4}$ alkylthio, heterocyclic-$C_{1-4}$alkoxy, (di-$C_{1-4}$ alkylamino)($C_{3-7}$ cycloalkyl)$C_{2-4}$ alkoxy, ($C_{1-4}$ alkylamino)($C_{3-7}$ cycloalkyl)$C_{2-4}$ alkoxy and (amino)($C_{3-7}$ cycloalkyl)$C_{2-4}$ alkoxy;

(e) amino, $C_{1-4}$ alkylamino, $C_{1-6}$ acylamino, aminoacetylamino, $C_{1-4}$ alkylsulfonylamino, halosubstituted-$C_{1-4}$ alkylsulfonylamino, halosubstituted-$C_{1-4}$ alkylamino or $C_{1-4}$ alkoxycarbonylaminoacetylamino;

(f) piperazinylcarbonyl, morpholinocarbonyl, nitro, cyano, hydroxy, $C_{1-4}$ alkylsulfonyl, $C_{1-4}$ alkylsulfinyl or di-$C_{1-4}$ alkylaminosulphenyl;

(g) $C_{1-4}$ alkylthio, $C_{1-6}$ acylthio, amino-$C_{1-6}$ acylthio, $C_{1-4}$ alkylsulfonylthio, halosubstituted-$C_{1-4}$ alkylthio or $C_{1-4}$ alkoxyaminoacetylthio;

(h) $C_{2-7}$ alkenyl or $C_{2-7}$ alkynyl, the $C_{2-7}$ alkenyl or $C_{2-7}$ alkynyl being optionally substituted with one, two or three substituents independently selected from amino, $C_{1-4}$ alkylamino, di-$C_{1-4}$ alkylamino, hydroxy, ($C_{1-4}$ alkoxy, piperazinyl, oxopyrrolidinyl, pyrrolidinyl, $C_{2-4}$ alkylenedioxy, halo, $C_{1-6}$ acyloxy, oxo, morpholino, $C_{1-4}$ alkylaminocarbonyl-$C_1$-acylamino, $C_{1-4}$ alkoxycarbonyl-$C_{1-6}$ acylamino, $C_{1-4}$ alkoxycarbonylpiperazinyl, $C_{1-6}$ acylpiperazinyl and $C_{1-4}$ alkylthio; and (i) $C_{7-14}$ azacycloalkyl optionally substituted with one or two substituents independently selected from oxo and $C_{1-4}$ alkyl;

$R^5$ is hydrogen or $C_{1-4}$ alkyl;

m is 0, 1 or 2; and n is 0, 1, 2, 3, 4 or 5;

and the pharmaceutically acceptable salts and prodrugs thereof.

Preferred compounds of this invention are those of the formula (II) wherein (A), is 2,6-dichloro; Y is —(CH$_2$)—; $R^1$ and $R^2$ are methyl;

$R^4$ is phenyl substituted at the 2-position with substituent selected from ethylenedioxyethyl, aminoethoxymethyl, aminoethoxy, aminopropoxy, aminopropoxymethyl, phenylthiomethyl, (dimethylamino)propyl, diethylaminomethyl, hydroxy, morpholinomethyl, methanesulphonylamino, oxopyrrol dinoethoxy, t-butoxycarbonylpiperazinomethyl, trifluoroethylamino, methylcarbamoylpropanoylaminomethyl, diethylaminoethoxymethyl, trifuloromethanesulfonylamino, piperazinocarbonyl, ethylaminoethoxymethyl, pyrrolidinoethoxymethyl, morpholinoethoxymethyl, piperidinoethoxy and dimethylaminoethoxy; and $R^5$ is hydrogen.

The present invention also relates to a process for preparing a compound of the formula

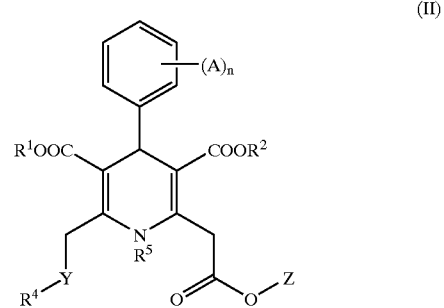

(II)

wherein

A is independently halo;

Y is —(CH$_2$)$_m$—, —C(O)— or —S(O)—;

Z is hydrogen, $C_{1-4}$ alkyl or metal;

$R^1$ and $R^2$ are independently $C_{1-4}$ alkyl;

$R^4$ is phenyl substituted at the 2-position with substituent selected from (a) $C_{1-4}$ alkyl substituted with one, two or three substituents independently selected from amino, amino-$C_{2-4}$ alkoxy, phenylthio, $C_{1-4}$ alkyl-phenylthio, di-$C_{1-4}$ alkylamino-$C_{2-4}$ alkoxy, $C_{1-4}$ alkylamino-$C_{2-4}$ alkoxy., $C_{1-4}$ alkylamino, di-$C_{1-4}$ alkylamino, hydroxy, $C_{1-4}$ alkoxy, piperazinyl, oxopyrrolidinyl, pyrrolidinyl, $C_{2-4}$ alkylenedioxy, $C_{1-4}$ acyloxy, oxo, morpholino, $C_{1-4}$ alkylaminocarbonyl-$C_{1-6}$ acylamino, $C_{1-4}$ alkoxycarbonyl-$C_{1-6}$ acylamino, $C_{1-4}$ alkoxycarbonylpiperazinyl, $C_{1-4}$ acylpiperazinyl, $C_{1-4}$ alkylthio, heterocyclic-$C_{1-4}$ alkoxy, (di-$C_{1-4}$ alkylamino)($C_{3-7}$ cycloalkyl)$C_{2-4}$ alkoxy, ($C_{1-4}$ alkylamino)($C_{3-7}$ cycloalkyl)$C_{2-4}$ alkoxy and (amino)($C_{3-7}$ cycloalkyl)$C_{2-4}$ alkoxy;

(b) $C_{5-7}$ alkyl optionally substituted with one, two or three substituents independently selected from amino, amino-$C_{2-4}$ alkoxy, phenylthio, $C_{1-4}$ alkyl-phenylthio, di-$C_{1-4}$ alkylamino-$C_{2-4}$ alkoxy, $C_{1-4}$ alkylamino-$C_{2-4}$ alkoxy, $C_{1-4}$ alkylamino, di-$C_{1-4}$ alkylamino, hydroxy, $C_{1-4}$ alkoxy, piperazinyl, oxopyrrolidinyl, pyrrolidinyl, $C_{2-4}$ alkylenedioxy, $C_{1-4}$ acyloxy, oxo, morpholino, $C_{1-4}$ alkylaminocarbonyl-$C_{1-6}$ acylamino, $C_{1-4}$ alkoxycarbonyl-$C_{1-6}$ acylamino, $C_{1-4}$ alkoxycarbonylpiperazinyl, $C_{1-6}$ acylpiperazinyl, $C_{1-4}$ alkylthio, heterocyclic-$C_{1-4}$ alkoxy, (di-$C_{1-4}$ alkylamino)($C_{3-7}$ cycloalkyl)$C_{2-4}$ alkoxy, ($C_{1-4}$ alkylamino)($C_{3-7}$ cycloalkyl)$C_{2-4}$ alkoxy and (amino)($C_{3-7}$ cycloalkyl)$C_{2-4}$ alkoxy;

(c) $C_{1-4}$ alkoxy or $C_{1-4}$ alkylthio, the $C_{1-4}$ alkoxy or $C_{1-4}$ alkylthio being substituted with one, two or three substituents independently selected from amino, amino-$C_{2-4}$ alkoxy, phenylthio, $C_{1-4}$ alkyl-phenylthio, di-$C_{1-4}$ alkylamino-$C_{2-4}$ alkoxy, $C_{1-4}$ alkylamino-$C_{2-4}$ alkoxy, $C_{1-4}$ alkylamino, di-$C_{1-4}$ alkylamino, hydroxy, $C_{1-4}$ alkoxy, piperazinyl, oxopyrrolidinyl, pyrrolidinyl, $C_{2-4}$ alkylenedioxy, $C_{1-6}$ acyloxy, oxo, morpholino, $C_{1-4}$ alkylaminocarbonyl-$C_{1-6}$ acylamino, $C_{1-4}$ alkoxycarbonyl-$C_{1-6}$ acylamino, $C_{1-4}$ alkoxycarbonylpiperazinyl, $C_{1-6}$ acylpiperazinyl, $C_{1-4}$ alkylthio, heterocyclic;-$C_{1-4}$ alkoxy, (di-$C_{1-4}$ alkylamino)($C_{3-7}$ cycloalkyl)$C_{2-4}$ alkoxy, ($C_{1-4}$ alkylamino)($C_{3-7}$ cycloalkyl)$C_{2-4}$ alkoxy and (amino)($C_{3-7}$ cycloalkyl)$C_{2-4}$ alkoxy;

(d) $C_{5-7}$ alkoxy or $C_{5-7}$ alkylthio, the $C_{5-7}$ alkoxy or $C_{5-7}$ alkylthio being optionally substituted with one, two or three substituents independently selected from amino, amino-$C_{2-4}$ alkoxy, phenylthio, $C_{1-4}$ alkyl-phenylthio, di-$C_{1-4}$ alkylamino-$C_{2-4}$ alkoxy, $C_{1-4}$ alkylamino-$C_{2-4}$ alkoxy, $C_{1-4}$ alkylamino, di-$C_{1-4}$ alkylamino, hydroxy, $C_{1-4}$ alkoxy, piperazinyl, oxopyrrolidinyl, pyrrolidinyl, $C_{2-4}$ alkylenedioxy, $C_{1-6}$ acyloxy, oxo, morpholino, $C_{1-4}$ alkylaminocarbonyl-$C_{1-6}$ acylamino, $C_{1-4}$ alkoxycarbonyl-$C_{1-6}$ acylamino, $C_{1-4}$ alkoxycarbonylpiperazinyl, $C_{1-6}$-acylpiperazinyl, $C_{1-4}$ alkylthio, heterocyclic-$C_{1-4}$ alkoxy, (di-$C_{1-4}$ alkylamino)($C_{3-7}$ cycloalkyl)$C_{2-4}$ alkoxy, ($C_{1-4}$ alkylamino)($C_{3-7}$ cycloalkyl)$C_{2-4}$ alkoxy and (amino)($C_{3-7}$ cycloalkyl)$C_{2-4}$ alkoxy;

(e) amino, $C_{1-4}$ alkylamino, $C_{1-6}$ acylamino, aminoacetylamino, $C_{1-4}$ alkylsulfonylamino, halosubstituted-$C_{1-4}$ alkylsulfonylamino, halosubstituted-$C_{1-4}$ alkylamino or $C_{1-4}$ alkoxycarbonylaminoacetylamino;

(f) piperazinylcarbonyl, morpholinocarbonyl, nitro, cyano, hydroxy, $C_{1-4}$ alkylsulfonyl, $C_{1-4}$ alkylsulfinyl or di-$C_{1-4}$ alkylaminosulphenyl;

(g) $C_{1-4}$ alkylthio, $C_{1-6}$ acylthio, amino-$C_{1-6}$ acylthio, $C_{1-4}$ alkylsulfonylthio, halosubstituted-$C_{1-4}$ alkylthio or $C_{1-4}$ alkoxyaminoacetylthio;

(h) $C_{2-7}$ alkenyl or $C_{2-7}$ alkynyl, the $C_{2-7}$ alkenyl or $C_{2-7}$ alkynyl being optionally substituted with one, two or three substituents independently selected from amino, $C_{1-3}$ alkylamino, di-$C_{1-4}$ alkylamino, hydroxy, $C_{1-4}$ alkoxy, piperazinyl, oxopyrrolidinyl, pyrrolidinyl, $C_{2-4}$ alkylenedioxy, halo, $C_{1-6}$ acyloxy, oxo, morpholino, $C_{1-4}$ alkylaminocarbonyl-$C_{1-6}$ acylamino, $C_{1-4}$ alkoxycarbonyl-$C_{1-6}$ acylamino, $C_{1-4}$ alkoxycarbonylpiperazinyl, $C_{1-6}$ acylpiperazinyl and $C_{1-4}$alkylthio; and (i) $C_{7-14}$ azacycloalkyl optionally substituted with one or two substituents independently selected from oxo and $C_{1-4}$ alkyl;

$R^5$ is hydrogen or $C_{1-4}$ alkyl;

m is 0, 1 or 2; and n is 0, 1, 2, 3, 4 or 5;

or a pharmaceutically acceptable salt thereof, comprising (a) reacting a compound of formula $R^4$—$X'$ (V-3') wherein $X'$ is halo or trifluoromethanesulfonate, and $R^4$ is as defined above, with a compound of formula $CH_2$=CH—COOH or $CH_2$=CH—$COOR^1$, in the presence of Pd Catalyst, to obtain a compound of formula $R^4$—$CH_2$=CH—COOH (V-2) or $R^4$—$CH_2$=CH—$COOR^1$;

(b) reducing the compound of formula $R^4$—$CH_2$=CH—COOH (V-2) or $R^4$—$CH_2$=CH—$COOR^1$ to obtain a compound of formula $R^4$—$(CH_2)_2$—COOH (V-1') or $R^4$—$(CH_2)_2$—$COOR^1$;

(c) hydrolyzing the compound of formula $R^4$—$(CH_2)_2$—$COOR^1$ to obtain a compound of formula $R^4$—$(CH_2)_2$—COOH (V-1');

(d) decarboxylative carbon alkylating a compound of formula $CH_3O_2CCH_2COOK$ with the compound of formula $R^4$—$(CH_2)_2$—COOH (V-1') to obtain a compound of formula

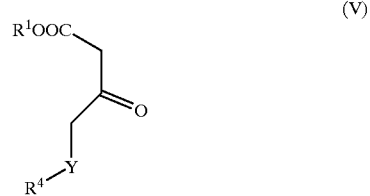

(V)

wherein $R^1$, $R^4$ and Y are as defined above;

(e) reacting the compound of formula (V) with a compound of formula

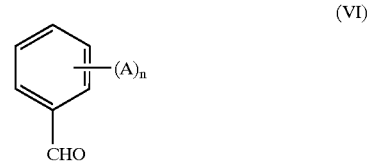

(VI)

wherein A and n are as defined above, to obtain a compound of formula

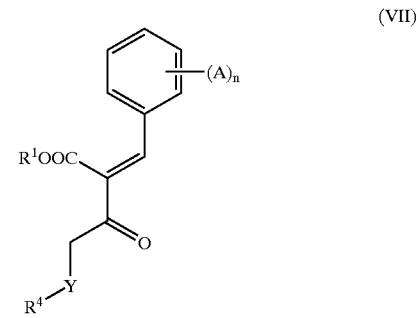

(VII)

wherein $R^1$, $R^4$, Y, A and n are as defined above;

(f) reacting the compound of formula (VII) with a compound of formula

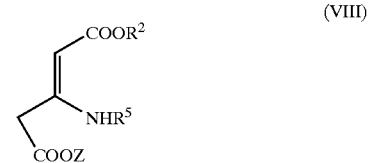

(VIII)

wherein $R^2$, $R^5$ and Z are as defined above, to obtain a compound of the formula (II).

In a preferred embodiment, the above process relates to the preparation of a compound of the formula (II), wherein $(A)_n$ is 2,6-dichloro; Y is —$(CH_2)$—; Z is hydrogen, $C_{1-4}$ alkyl, Li, K or Na; $R^1$ and $R^2$ are methyl;

$R^4$ is phenyl substituted at the 2-position with substituent selected from ethylenedioxyethyl, aminoethoxymethyl, aminoethoxy, aminopropoxy, aminopropoxymethyl, phenylthiomethyl, (dimethylamino)propyl, diethylaminomethyl, hydroxy, morpholinomethyl, methanesulphonylamino, oxopyrrolidinoethoxy, t-butoxycarbonylpiperazinomethyl, trifluoroethylamino, methylcarbamoylpropanoylaminomethyl, diethylaminoethoxymethyl, trifuloromethane-sulfonylamino, piperazinocarbonyl, ethylaminoethoxymethyl, pyrrolidinoethoxymethyl, morpholinoethoxymethyl, piperidinoethoxy and dimethylaminoethoxy; and $R^5$ is hydrogen.

DETAILED DESCRIPTION OF THE INVENTION

The 1,4-dihydropyridine compounds of formula (I) of this invention may be prepared by a variety of synthetic methods known to those skilled in the art. For example, the 1,4-dihydropyridine compounds of formula (I), may be prepared by reaction of compound (II) with compound (III), followed, if desired, by conversion of a compound (Ill) in which $R^3$ is H into a compound (III) in which $R^3$ is other than H, as indicated in the following Preparation Method A.

Preparation Method A

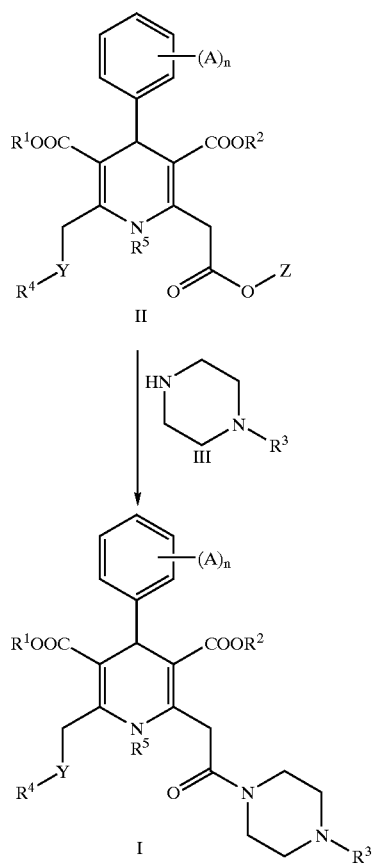

(wherein Z is hydrogen or lower alkyl (e.g., $C_{1-4}$ alkyl) such as methyl and ethyl; and the other symbols are as already defined)

In Preparation Method A, when Z is lower alkyl, the compound (II) may be first subjected to selective saponification of the ester residue at the 2-position of the dihydropyridine ring, followed by acidification to afford a free acid, which is coupled with the compound (III) to give the 1,4-dihydropyiridine (I). When Z is H, the compound (II) may be directly coupled with the compound (III) to obtain the 1,4-dihydropyridine (I).

The selective saponification and the acidification may be carried out by conventional procedures. In a typical procedure, the selective saponification is carried out by treatment with sodium hydroxide in a suitable reaction-inert solvent at a temperature in the range from −20 to 40° C., usually from 10° C. to 30° C. for 3 minutes to 4 hours, usually 15 minutes to 1 hour. In a typical procedure, the acidification is carried out by treatment with diluted hydrochloric acid in a suitable reaction-inert solvent such as water at a temperature in the range from 0 to 30° C., usually from 5° C. to 25° C. for 1 minute to 1 hour, usually 5 minutes to 15 minutes.

The 1,4-dihydropyridine (I) can be obtained from the corresponding 1,4-dihydropyridine (II) wherein $R^3$ is H by a coupling reaction between the obtained acid and 4-N-substituted piperazine. The condensation may be carried out in a reaction-inert solvent such as aqueous or non-aqueous organic solvents (e.g., tetrahydrofuran, DMF, dioxane, acetone, dimethoxyethane and acetonitrile); halogenated hydrocarbons such as chloroform, dichloromethane and dichloroethane (preferably dichloromethane) using a coupling agent such as dicyclohexylcarbodiimide (DCC), water soluble carbodiimide (WSC), 2-ethoxy-N-ethoxycarbonyl-1,2-dihydroquinoline, benzotriazol-1-yloxy-tris (dimethylamino) phosphonium hexafluorophosphate (BOP), diethyl azodicarboxylate-triphenylphosphine, diethylcyanophosphonate (DEPC), diphenylphosphorylazide (DPPA), bromotripyrrolidino phosphonium hexafluorophosphate (PyBrop[trademark]), bis(2-oxo-3-oxazolidinyl) phosphinic chloride (BOPCI), benzotriazole-1-yl-oxy-tris-pyrrolidino-phosphonium hexafluorophosphate (PyBOP), 2-(1-H-benzotriazole-1-yl)-1,1,3,3,-tetramethyluronium hexafluorophosphate (HBTU) and ethyl chloroformate. This reaction may be carried out at a temperature in the range from −30 to 40° C., usually from 0° C. to 25° C. for 10 minutes to 96 hours, usually 30 minutes to 24 hours.

In addition, when $R^3$ is substituted-alkyl, the 4-N-substituted piperazines (III) as used herein may be either known or may be prepared by known methods. For example, the 4-N-substituted piperazines may be prepared by means of (1) N-alkylation of 1-N-protected piperazine with appropriate alkyl halide, $R^3$-halo, (2) reductive amination of 1-N-protected piperazine with appropriate aldehyde or ketone in the presence of a reducing agent, followed by deprotection of the 1-N-protecting group, or (3) Michael addition of 1-N-protected piperazine with appropriate conjugated ketones, esters or amides, or (4) piperazine ring construction from N-substituted amine. Suitable 1-N-protecting groups include, for example, benzyl, benzyloxycarbonyl and t-butoxycarbonyl group.

The reductive alkylation may be carried out with appropriate aldehyde or ketone in a suitable reaction-inert solvent such as aqueous or non-aqueous organic solvents (e.g., tetrahydrofuran, dioxane, acetone, dimethoxyethane and acetonitrile); halogenated hydrocarbons such as chloroform, dichloromethane and dichloroethane (preferably dichloromethane), in the presence of a suitable reducing agent such as sodium borohydride, sodium cyanoborohydride or sodium triacetoxy borohydride at a temperature in the range from −20 to 120° C., usually 0 to 80° C. for 10 minutes to 1 week, usually 30 minutes to 96 hours, optionally in the presence of molecular sieves. Alternatively, alkylation can be made by two step synthesis. A ketone may be treated with an amine in an inert solvent such as toluene or xylene, at a temperature in the range from 80 to 130° C., usually 100 to 120° C. for 10 hours to 2 week, usually 1 days to 1 week, preferably 3 to 5 days. The product may be reduced by hydrogenation in the presence of appropriate catalyst such as palladium on carbon and platinum oxide (IV), usually platinum oxide (IV) in an inert solvent such as ethanol and ethyl acetate, usually ethyl acetate, at a temperature in the range from 10 to 60° C., A usually 20 to 30° C. for 1 hour to 3 days, usually 3 hours to 10 hours.

Typical Micheal addition reaction may be carried out at a temperature in the range from 30° C. to 120° C., usually from 60° C. to 100° C. for 5 hours to a week, usually 10 hours to 4 days.

Preparation Method B-I

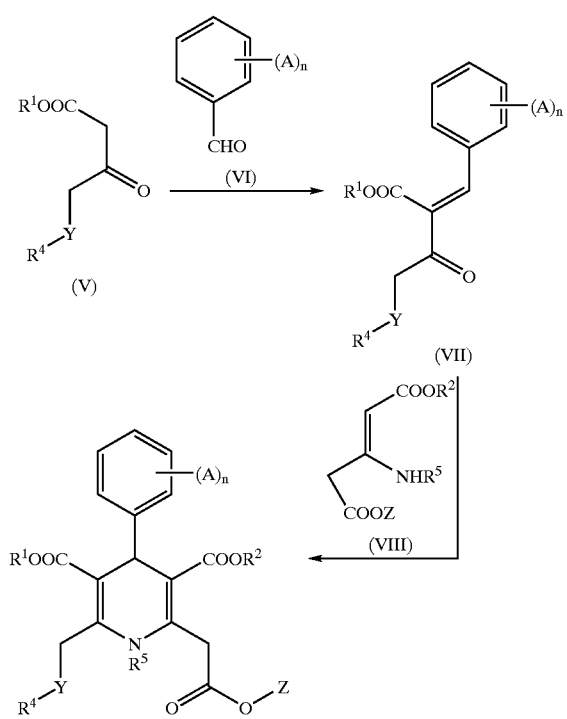

(wherein Z is lower alkyl such as methyl and ethyl; and the other symbols are as already defined)

Scheme B-I

This method utilizes the modified Hantzsch synthesis as described in A. Sausins and G. Duburs, *Heterocycles*, 1988, 27, 269. In this method, beta-keto ester (V) is first reacted with substituted benzaldehyde (VI) to obtain compound (VII). This reaction may be carried out in a suitable reaction-inert solvent. Suitable solvents include, for example, aromatic hydrocarbons such as benzene, toluene and xylene; alcohols such as methanol, ethanol, propanol and butanol; ethers such as diethyl ether, dioxane and tetrahydrofuran; halogenated hydrocarbons such as methylene dichloride, chloroform and dichloroethane; amides such as N,N-dimethylformamide; and nitrites such as acetonitrile. This reaction may be carried out at a temperature of 0° C. to 200° C., preferably from 80° C. to 120° C. for 30 minutes to 24 hours, preferably 30 minutes to 6 hours. If desired, this reaction may be catalyzed by a base such as piperidine, pyridine or alkoxide, or by an acid catalyst such as acetic acid, $TiCl_4$ or p-toluenesulfonic acid.

Thereafter, the benzylidene (VII) as obtained above is reacted with enamine (VII) in the presence of, or absence of a suitable condensing agent such as Lewis acids, to obtain the 1,4-dihydropyridine (II). This reaction may be carried out in the presence of, or absence of the reaction-inert solvent as listed above. However, this reaction may preferably carried out in the absence of a solvent. This reaction may be carried out at a temperature of 0° C. to 20° C., preferably, from 60° C. to 150° C. for 30 minutes to 48 hours, preferably 10 hours to 20 hours.

In addition, the beta-keto esters (V) which can be used herein may be prepared by known methods as shown in, for example: (1) *J. Labelled Compds. Radiopharm.*, 1989, 27, 599; (2) *J. Org. Chem.*, 1989, 54, 3258; (3) *J. Am. Chem. Soc.*, 1974, 96, 1082; (4) *J. C. S. Perkin I*, 1979, 529; (5) *Synthesis*, 1986, 37; (6) *J. C. S. Chem. Commun.*, 1977, 932, (7) *Angew. Chem. Int. Ed. Engl.*, 1979, 18, 72 and (8) *Tetrahedron Lett.*, 1983, 24, 5425. The benzaldehydes (VI) which can be used herein may be either already known or may be prepared according to the reported methods.

Preparation Method B-II

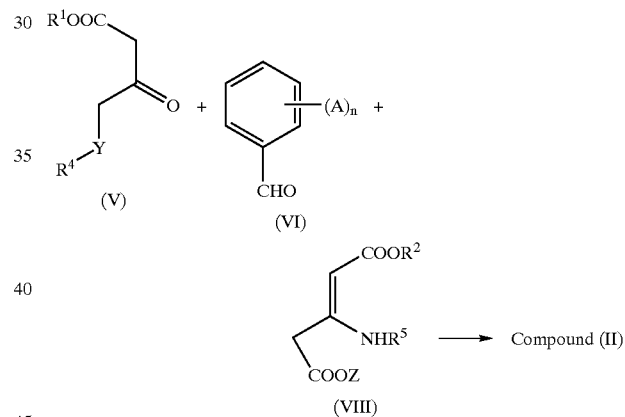

(wherein all the symbols are as already definred)

Scheme B-II

This method utilizes the three components Hantzsch reaction. In a typical procedure, the beta-keto ester (V), the substituted benzaldehyde (VI) and the enamine (VII) may be heated together in a suitable reaction-inert solvent as listed above (preferably lower alkanols such as methanol and ethanol). Preferably, a small amount of a lower alkanoic acid such as acetic acid is added as catalyst. The reaction mixture may be heated at 80° C. to 200° C., preferably from 100° C. to 140° C. for 30 minutes to 1 week, usually 24 hours to 96 hours.

Preparation Method B-III

Compounds of formula (VIII) may be prepared by a process of this invention according to Scheme B-III.

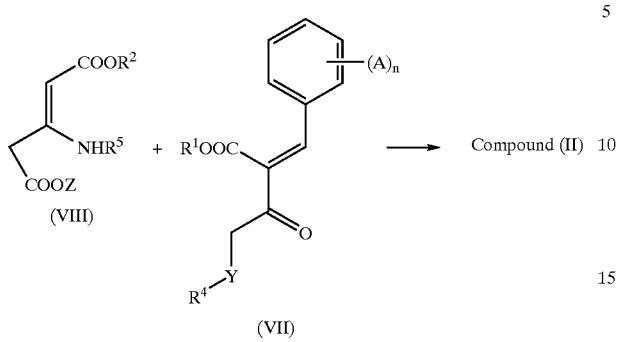

Scheme B-III

Scheme B-II exemplifies a process of this invention for preparing a compound of formula (II) comprising step (a): addition of an enamine compound of formula (VII) to an alkylene compound of formula (VII) followed by step (b) acid catalyzed cyclization reaction of the resulting compound in step (a).

The former addition step (a) may be carried out under conditions applied to nucleophilic addition reactions using a suitable base in a reaction inert solvent. More preferably, the reaction may be carried out under conditions commonly used in Michael-type addition. Preferred bases for this reaction are those used in Michael-type reactions. Examples of the preferred bases include alkylmagnesium halides known as Grignard reagents and halomagnesium alkoxides. More preferred bases include ($C_1$–$C_6$)alkylmagnesium bromide and tert-butoxy-magnesium bromide. Preferred solvents used in this reaction include ($C_1$–$C_4$)alkanol, tetrahydrofuran (THF), diethyl ether, dioxane, hexane, toluene, 1,2-dimethoxy ethane (DME) and the like. This reaction may be carried out at a temperature from about –150° C. to reflux, preferably from about –100 to 100° C. In view of convenience, this reaction may be carried out at about room temperature using, for example, halomagnesium ($C_1$–$C_4$) alkoxides, ($C_1$–$C_6$)alkylmagnesiumhalides, metalhydrides, metal ($C_1$–$C_3$)alkoxides, magnesium-di[($C_1$–$C_3$)alkoxides], metal-n-butoxide, metal-sec-butoxide, metal-tert-butoxide or a metalcarbonate such as $K_2CO_3$. In case of the base is $K_2CO_3$, the reaction is effectively run in THF. In case of the base is CsF or KF, the reaction is effectively run in THF or methanol (MeOH) at an elevated temperature such as at about 60° C. In case of using butyllithium (BuLi), the reaction is effectively run in THF at from about –780 to about –30° C. In case of using halomagnesium ($C_1$–$C_4$) alkoxides or ($C_1$–$C_6$)alkylmagnesiumhalides, a preferred solvent is THF. Suitable reaction time ranges from about 3 minutes to about 2 days, preferably from about 30 minutes to about 40 hours.

The subsequent cyclization process step (b) may be carried out in the presence of a protonic acid. Suitable protonic acids include ($C_1$–$C_6$)alkanoic acid such as acetic acid, hydrochloric acid (HCl) and sulfonic acids such as p-toluenesulfonic acid. It is preferred to add a non-protonic Lewis acid to the reaction mixture in combination with the protonic acid, when the base used in Step (a) is other than magnesium (VII) bases. This reaction may be carried out at a temperature from about –150° C. to reflux, preferably from about –100° to 100° C. The reaction time ranges from about 1 second to 5 days, preferably 5 minutes to 20 houres.

Generally, those reactions illustrated in Scheme B-III may be carried out at about –78° C. using dry-ice/acetone or dry-ice/methanol, about 0° C. using an ice-bath, room temperature or 100° C., preferably at about 0° C. or about room temperature.

The reaction steps (a) and (b) are performed in the same reaction vessel under mild conditions with high-yield.

An enamine compound of formula (VIII) may be prepared according to procedures known to those skilled in the art, such as those illustrated in Scheme B-Ill-a.

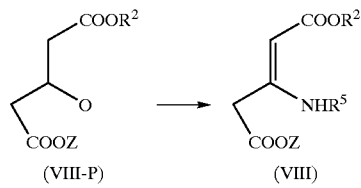

Scheme B-III-a

Typically, a beta-keto ester compound of formula (VIII-P) may be transformed to a compound of formula (VIII) wherein $R^2$, $R^5$ and Z are defined as above. This reaction may be carried out in a reaction inert solvent resolving ammonia gas at a temperature in the range of from about 0° to 60° C. Suitable reaction inert solvents include lower alkanols such as methanol and ethanol. Alternatively, an ammonia gas containing solution given above may be added to a solution containing a beta-keto ester (VIII-P). The mixture is reacted at a temperature in the range of from about 0 to 60° C. to yield the enamine compound (VIII). More conveniently, the compund of formula (VII) may be synthesized by a reaction of the compound of formula (VIII-P) with ammonium hydrogencarbonate or ammonium acetate in a reaction inert solvent or neat at in a range of ambient temperature to 120° C., preferablly, at 30 to 80° C. Suitable reaction inert solvents include lower alkanols, such as methanol and ethanol, DMF, $CH_3CN$ or DMSO, but more easily the reaction may be run without solvent.

An alkylene compound of formula (VII) may be prepared according to procedures known to those skilled in the art scheme B-III-b illustrates one embodiment of the preparation process.

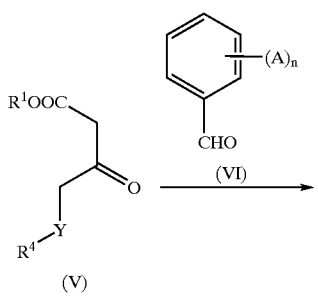

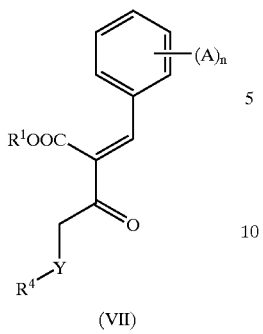

(VII)

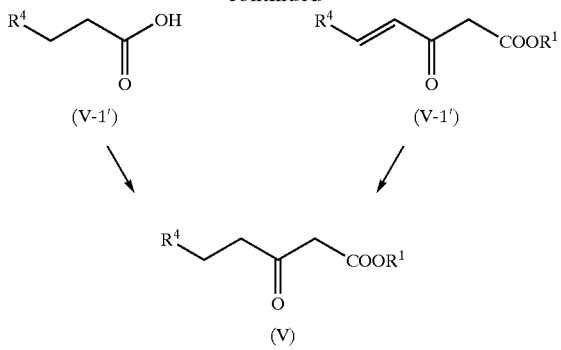

(V)

Scheme B-III-b

A carbonyl compound of formula (V) may be subjected to a coupling reaction with an aldehyde compound of formula (VI) to give the alkylene compound of formula (VII) according to a known procedure. For example, a compound of formula (V) may be reacted with a compound of formula (VI) according to a procedure reported by L. Tietze et al. Liebigs Ann. Chem., pp. 321–329, 1988. This reaction may be carried out in a suitable reaction inert-solvent for example an aromatic hydrocarbon such as benzene, toluene and xylene, an alcohol such as methanol, ethanol, propanol and butanol, an ether such as diethyl ether, dioxane and tetrahydrofuran (THF), a halogenated hydrocarbon such as methylene dichloride, chloroform and dichloroethane, an amide such as N,N-dimethylformamide (DMF), and a nitrile such as acetonitrile. This reaction may be carried out at a temperature in a range of from about 0° C. to the reflux temperature of the reaction mixture, preferably from about 800 to the 120° C. for from about 30 minutes to 24 hours, preferably from 30 minutes to 6 hours. This reaction may conveniently be carried in the presence of a base or acid catalyst. Suitable base catalysts are such as piperidine, pyridine and alkoxide, and suitable acid catalysts are such as acetic acid, $TiCl_4$ and p-toluenesulfonic acid.

An intermediate compound of formula (V) may be prepared starting from a known compound according to a procedure known to those skilled in the art. For example, a compound of formula (V) may be prepared according to the procedure described in Scheme B-III-c.

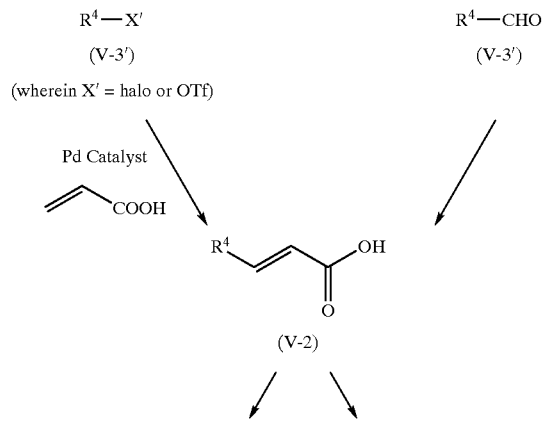

Scheme B-III-c

An aldehyde compound (V-3), wherein $R^4$ is defined as above, is reacted with malonic acid under a basic condition. For example, this reaction may be carried out in the presence of a weak base such as piperidine in a reaction inert solvent such as pyridine to give a carboxylic acid compound of formula (V-2). Alternatively, the compound of formula (V-2) may be synthesized by a so-called "Heck reaction". Thus, $R_4$—X' (X'=Cl, Br, I, trifluoromethanesulfonate (OTf) may be reacted with acrylic acid in the presence of appropriate Pd catalyst in a reaction inert solvent, such as DMF, $H_2O$, dimethylacetamide, N-ethylpiperidine, triethylamine, tributylamine, toluene, xylene, acetonitrile, 1,3-dimethyl-3,4,5,6-tetrahydropyrimidone, 1,3-dimethyl-2-imidazolinone, 1-methyl-2-pyrrolidinone, tetrahydrofuran, dimethoxyethane, t-butylmethylether, dimethylsulfoxide, sulforane, preferably DMF, $H_2O$ and tributylamine. The compound (V-2) thus obtained may be subjected to an aliphatic nucleophilic substitution reaction in the presence of a coupling agent to give a pentenoate compound of formula (V-1). This reaction may conveniently be carried out first by treating the compound of formula (V-1) with a coupling agent such as N,N'-carbonyldiimidazole in a reaction inert solvent such as dimethylformamide, then reacting with a neucleophilic reagent such as $CH_3O_2CCH_2COOK$ in the presence of a Lewis acid such as magnesium chloride. The former treatment may be carried out at a temperature in the range of 0° to 60° C., preferably at about room temperature for from about 1 minutes to 12 hours. The latter reaction may be carried out at the temperature in the range of from about 0° to 100° C., preferably from about room temperature to 60° C. for from about 1 minutes to 12 hours. The compound of formula (V-1) may be reduced over a metal catalyst under hydrogen atmosphere to give the compound of formula (V) according to a known procedure. Suitable catalysts are such as Raney nickel catalyst and a noble metal catalysts including palladium on carbon and palladium hydroxide. This reaction may be carried out in a reaction inert solvent such as methanol, at about room temperature under hydrogen atmosphere at an appropriate pressure for about 1 minutes to 12 hours. Alternatively, a compund of formula (V) may be synthesized by reduction of a compund of formula (V-2) and following nucleophilic coupling of the resulting a compund of formula (V-1') with $CH_3O_2CCH_2COOK$ as indicated reaction condition above. Instead of the $CH_2=CH—COOH$ we can use $CH_2=CH—COO—R^1$ etc.

A ketone compound of formula (V) and a substituted benzaldehyde compound of formula (VI) may also be prepared according to known procedures (e.g., (1) D. Scherling, *J. Labelled Compds. Radiopharm.*, Vol. 27', pp. 599-, 1989, (2) C. R. Holmquist et al., *J. Org. Chem.*, Vol. 54, pp. 3528-, 1989, (3) S. N. Huckin et al., *J. Am. Chem. Soc.*, Vol. 96, pp. 1082-, 1974, (4) *J. C. S. Perkin I*, pp. 529-, 1979, (5) *Synthesis* pp. 37, 1986, and (6) *J. C. S. Chem. Commun.*, pp. 932-, 1977).

Preparation Method B-IV

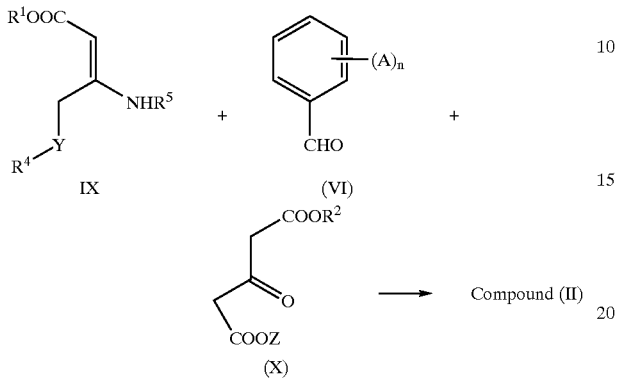

(wherein all the symbols are as already defined)

This method also utilizes the three components Hantzsch reaction as mentioned above. The reaction conditions similar to the above can be also used in this method.

The enamine (IX) may either be known compounds or may be prepared by known methods. For example, the enamine (IX) may be prepared by reacting the beta-keto ester (V) with ammonia or ammonium salt. More specifically, the beta-keto ester (V) may be dissolved in a suitable solvent such as lower alkanols (ex. methanol and ethanol). Excess amount of ammonia gas is introduced into the solution at a temperature of 0 to 60° C. Alternatively, a solution containing ammonia dissolved in the above solvent is added to the solution containing the beta-keto ester (V), and the resultant mixture is reacted at a temperature of 0 to 60° C., to obtain the enamine (IX). More conveniently, the compund of formula (VIII) may be synthesized by et reaction of the compound of formula (VIII-P) with ammonium hydrogencarbonate or ammonium acetate in a reaction inert solvent or neat at in a range of ambient temperature to 120° C., preferably, at 30 to 80° C. Suitable reaction inert solvents include lower alkanols, such as methanol and ethanol, DMF, $CH_3CN$ or DMSO, but more easily the reaction may be run without solvent.

The compounds of formula (I), and the intermediates above-mentioned preparation methods can be isolated and purified by conventional procedures, such as recrystallization or chromatographic purification.

General Synthesis of the Optical Active 1,4-dihydropyridine

The optically active compounds of this invention can be prepared by several methods. For example, the optically active compounds of this invention may be obtained by chromatographic separation or fractional crystallization from the final compounds or the intermediates in racemic form thereof.

For example, the optically active 1,4-dihydropyridine (I-o) may be prepared by reaction of the compound (II-o) with the compound (III), followed, if desired, by conversion of the compound (III) in which $R^3$ is H into the compound (III) in which $R^3$ is other than H, as indicated in the following Preparation Method A-o.

Preparation Method A-o

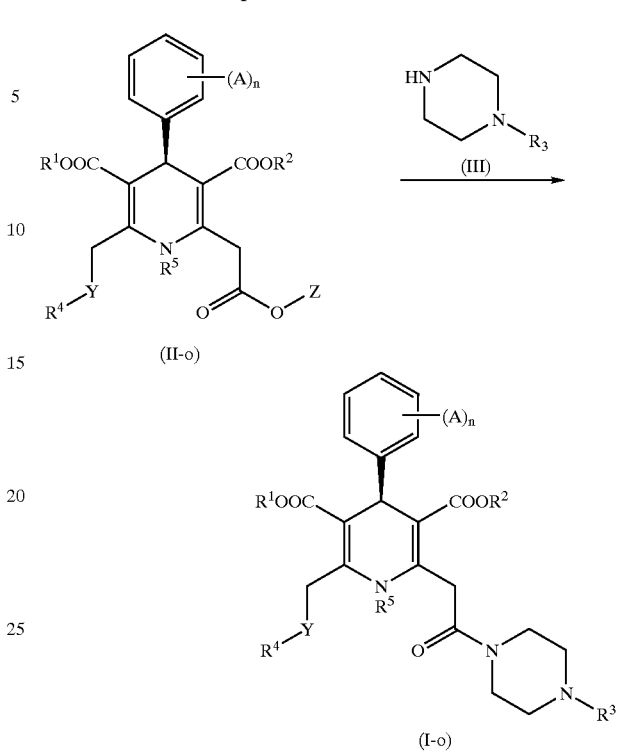

(wherein Z is hydrogen or lower alkyl (e.g., $C_{1-4}$ alkyl) such as methyl and ethyl; and the other symbols are as already defined)

In Preparation Method A-I, when Z is lower alkyl, the compound (11-o) may be first subjected to selective saponification of the ester residue at the 2-position of the dihydropyridine ring, followed by acidification to afford a free acid, which is coupled with the compound (III) to give the 1,4-dihydropyridine (1-o). When Z is H, the compound (11-o) may be directly coupled with the compound (III) to obtain the 1,4-dihydropyridine (I-o).

The selective saponification and the acidification may be carried out by conventional procedures. In a typical procedure, the selective saponification is carried out by treatment with sodium hydroxide in a suitable reaction-inert solvent such as methanol, dioxane and tetrahydrofuran (THF) at a temperature in the range from −20 to 40° C., usually from 10° C. to 30° C. for 3 minutes to 4 hours, usually 15 minutes to 1 hour. In a typical procedure, the acidification is carried out by treatment with diluted hydrochloric acid in a suitable reaction-inert solvent such as water at a temperature in the range from 0 to 30° C., usually from 50° C. to 25° C. for 1 minute to 1 hour, usually 5 minutes to 15 minutes.

A compound (I-o) can be obtained from the corresponding compound (11-o) wherein $R^3$ is H by a coupling reaction between the obtained acid and 4-N-substituted piperazine. The condensation may be carried out in a recaction-inert solvent such as aqueous or non-aqueous organic solvents (e.g., tetrahydrofurar, dioxane, acetone, DMF, dimethoxyethane and acetonitrile); halogenated hydrocarbons such as chloroform, dichloromethane and dichloroethane (preferably dichloromethane) using a coupling agent such as dicyclohexylcarbodiimide (DCC), water soluble carbodiimide (WSC), 2-ethoxy-N-ethoxycarbonyl-1,2-dihydroquinoline, benzotriazol-1-yloxy-tris (dimethylamino) phosphonium hexafluorophosphate (BOP), diethyl azodicarboxylate-triphenylphosphine, diethylcyanophosphonate (DEPC), diphenylphosphorylazide (DPPA), bromotripyrrolidino phosphonium hexafluorophosphate (PyBrop[trademark]) and ethyl chloroformate. This reaction may be carried out at a temperature in the range from −30 to 40° C., usually from 0° C. to 25° C. for 10 minutes to 96 hours, usually 30 minutes to 24 hours.

In addition, when $R^3$ is substituted-alkyl, the 4-N-substituted piperazines (III) as used herein may be either known or may be prepared by known methods. For example, the 4-N-substituted piperazines may be prepared by means of (1) N alkylation of 4-N-protected piperazine with appropriate alkyl halide, $R^3$-halo, (2) reductive amination of 4-N-protected piperazine with appropriate aldehyde or ketone in the presence of a reducing agent, followed by deprotection of the amino-protecting group, or (3) Michael addition of 4-N-protected piperazine with appropriate conjugated ketone, ester or amide, or (4) piperazine ring construction from N-substituted amine. Suitable amino-protecting groups include, for example, benzyl, benzyloxycarbonyl and t-butoxycarbonyl group.

The reductive alkylation may be carried out with appropriate aldehyde or ketone in a suitable reaction-inert solvent such as aqueous or non-aqueous organic solvents (e.g., tetrahydrofuran, dioxane, acetone, dimethoxyethane, acetonitrile, methanol and ethanol); halogenated hydrocarbons such as chloroform, dichloromethane and dichloroethane (preferably dichloromethane), in the presence of a suitable reducing agent such as sodium borohydride, sodium cyanoborohydride or sodium triacetoxyborohydride at a temperature in the range from −20 to 120° C., usually 0 to 80° C. for 10 minutes to 1 week, usually 30 minutes to 96 hours, optionally in the presence of molecular sieves. Alternatively, alkylation can be made by two step synthesis. A ketone may be treated with an amine in an inert solvent such as toluene or xylene, at a temperature in the range from 80 to 130° C., usually 100 to 120° C. for 10 hours to 2 week, usually 1 days to 1 week, preferably 3 to 5 days. The product may be reduced by hydrogenation in the presence of appropriate catalyst such as Palladium on carbon and platinum oxide (IV), usually platinum oxide in an inert solvent such as ethanol and ethyl acetate, usually ethyl acetate, at a temperature in the range from 10 to 60° C., usually 20 to 30° C. for 1 hour to 3 days, usually 3 hours to 10 hours.

Typical Micheal addition reaction may be carried out at a temperature in the range from 30° C. to 120° C., usually from 60° C. to 100° C. for 5 hours to a week, usually 10 hours to 4 days.

The optically active intermediates of formula (II) can be prepared by the following methods.

Preparation Method B-I-o (Fractional Crystallization)

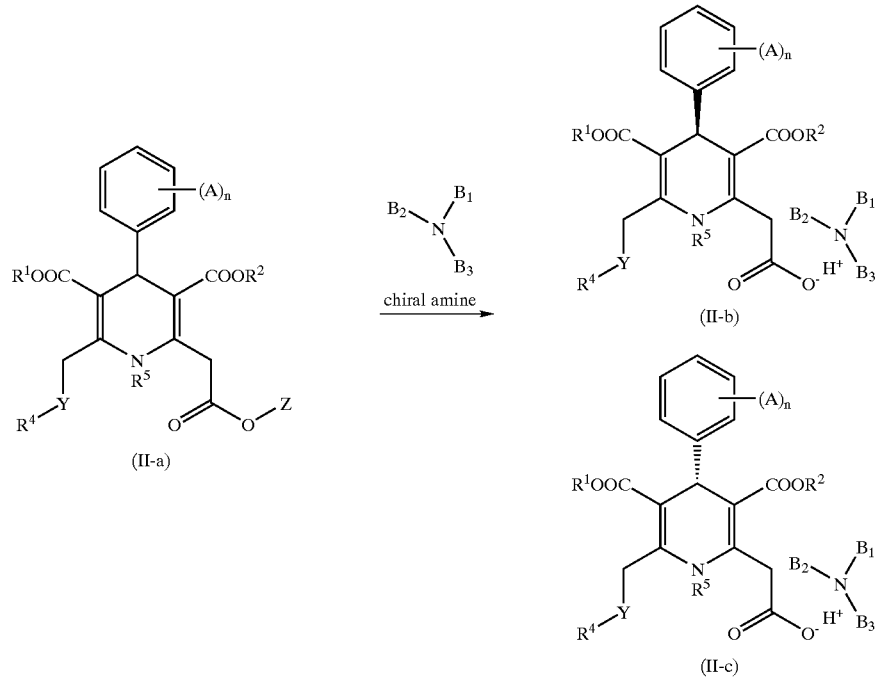

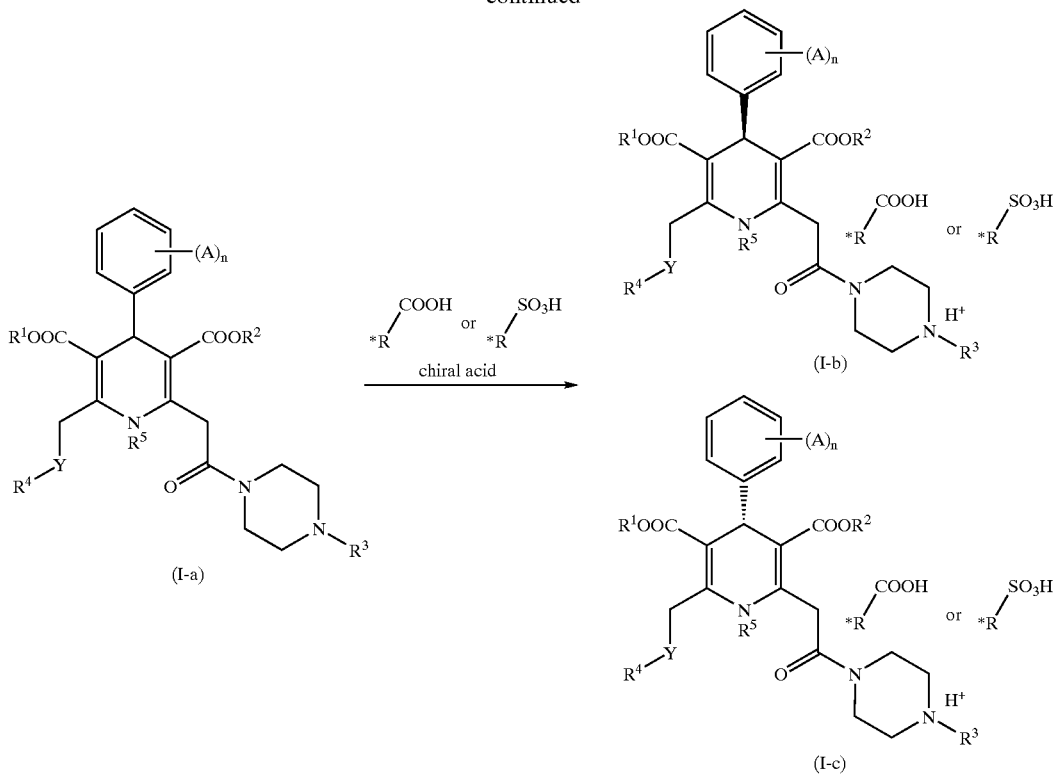

(wherein [B¹ B² B³]NH⁺ is a chiral amine residue; Z is hydrogen; R*COOH and R*SO₃H are chiral acids and the other symbols are already defined.)

In this method, an acid compound (II-a) may be subjected to a fractional crystallization with a chiral amine such as cinchonidine, cinchonine, quinine, burcine and phenethylamine or their derivatives, amino acids to obtain an amine salt (II-b). This reaction may be conducted in an organic solvent, preferably a pure or mixed alcoholic solvent selected from methanol, ethanol, 2-propanol and mixture thereof. The resulted salt may be further purified by several times recrystallization. The pure salt thus obtained may be converted to the corresponding carboxylic acid (an enantiomer of compound (II) wherein Z is H) by a partition between organic solvent such as ethyl acetate or dichloromethane and acid solution such as diluted hydrochloric acid followed by concentration. On the other hand, the salt of the antipode contained in the resulted mother liquid may be converted to the corresponding carboxylic acid (an enantiomer of compound (II) wherein Z is H) by the same procedure described above after concentration of the mother liquid. This acid may be further purified by crystallization in organic or inorganic solvents to give the antipode. This crystallization of the acid may be performed several times, if necessary, to improve its optical purity. Instead of R*COOH or R*SO₃H, we can use phosphonic acid such as (R*O)₂P(O)OH and R*O(R'O)P(O)OH.

Furthermore, a final compound (I-a) may be resolved into each salt of both enantiomers by the same procedure described above using chiral acid. The resolved salts thus obtained may be converted to the corresponding amines (each enantiomer of I-a) by a partition between organic solvent such as dichloromethane and basic solution such as aqueous sodium hydrogencarbonate or sodium hydroxide.

The preparation of other compounds of the formula (I), and intermediates thereof, not specifically described in the foregoing experimental section can be accomplished using combinations of the reactions described above that will be apparent to those skilled in the art.

The isolation and purification of compounds of formula (I), and the intermediates shown in the above reaction schemes, not specifically described in the foregoing experimental section can be accomplished using conventional procedures, such as recrystallization or chromatographic separation.

The compounds of formula (I) and their pharmaceutically acceptable salts can be administered to mammals, including humans, via either the oral, parenteral or topical routes. In general, these compounds are most desirably administered in doses ranging from about 0.3 mg to about 750 mg per day, preferably in doses ranging from about 10 mg to about 500 mg per day, in single or divided doses (i.e., from 1 to 4 doses per day), although variations will necessarily occur depending upon the species, weight and condition of the subject being treated, the disease state being treated and the particular route of administration chosen. For example, a dosage level that is in the range of from about 0.06 mg to about 2 mg per kg of body weight per day is most desirably employed for the treatment of inflammation.

The compounds of the present invention may be administered alone or in combination with pharmaceutically acceptable carriers or diluents by either of the routes previously indicated, and such administration may be carried out in single or multiple doses. More particularly, the novel therapeutic agents of the present invention can be administered in a wide variety of different dosage forms, i.e., they may be combined with various pharmaceutically acceptable inert carrier, in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various nontoxic organic solvents, etc. Moreover, oral pharmaceutical compositions can be suitably sweetened and/or flavored. In general, the therapeutically-effective compounds of this invention are present in such dosage forms at concentration levels ranging from about 5% to about 70% by weight, preferably from about 10% to about 50% by weight.

For oral administration, tablets containing various excipients such as microcrystalline cellulose, sodium citrate, calcium carbonate, dicalcium phosphate and glycine may be employed along with various disintegraits such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well known to those skilled in the art.

Additionally, it is also possible to administer the compounds of the present invention topically when treating inflammatory conditions of the skin and this may preferably be done by way of creams, jellies, gels, pastes, patches, ointments and the like, in accordance with standard pharmaceutical practice.

Method for Assessing Biological Activities:

The activity of the compounds of formula (I) of the present invention, as bradykinin antagonists, is determined by their ability to inhibit the binding of bradykinin at its receptor sites in recombinant human bradykinin B2 receptor expressing CHO-KL cells (from Receptor Biology, Inc.) employing radioactive ligancis.

The bradykinin antagonist activity of the 1,4-dihydropyridine compounds is evaluated by using the standard assay procedure described in, for example, Baenziger N. L., Jong Y-J. I., Yocum S. A., Dalemar L. R., Wilhelm E B., Vaurek R., Stewart J. M., *Eur. J. Cell Biol,* 1992, 58, 71–80. This method essentially involves determining the concentration of the individual compound required to reduce the amount of radiolabelled bradykinin ligands by 50% at their receptor sites in CHO-K1 cells, thereby affording characteristic $IC_{50}$ values for each compound tested.

More specifically, the assay is carried out as follows. First, rat, guinea pig or monkey ileum tissues are minced and suspended in 25 mM piperazine-N,N'-bis (2-ethanesulfonic acid) (PIPES) buffer (pH 6.8) containing 0.1 mg/ml of soybean trypsin inhibitor. Then, the tissues are homogenized using a Polytron homogenizer at setting 7 for 30 seconds three times, and then rehomogenized with a Teflon-coated homogenizer. The homogenized suspension is centrifuged at 1,200× g for 15 minutes. The pellet is rehomogenized and then centrifuged at 1,200× g for 15 minutes. The supernatant is centrifuged at 10,000× g for 60 minutes. The tissue pellets, CHO-KL cell membrane are suspended in 25 mM PIPES buffer (pH6.8) containing 1.25 mM dithiothreitol, 1.75 μg/ml bacitracin, 1 mM o-phenanthroline, 18.75 μM captopril and 1.25 mg/ml bovine serum albumin (BSA), in order to prepare tissue/cell suspensions. Then, 10 μl of test compound solution dissolved in phosphate buffered saline (PBS, pH 7.5) containing 2% DMSO (final) and 0.1% BSA (w/v) or 10 ml of 12.5 mM bradykinin in PBS (pH 7.5) containing 0.1% BSA (w/v) are placed in a reaction 96-well plate. 15 μl of 8.3 nM [3H]bradykinin is added to the compound solution or bradykinin solution in the 96-well plate. Finally 100 μl of the tissue or cell suspension is added to the mixture in the plate, and incubated at room temperature for 1 hour in the absence of light. After incubation, the resultant product in the reaction plates is filtered through 0.1% polyethylenimine presoaked LKB filermat. The filtrate is, washed using a Skatron auto cell harvester. The tissue bound radioactivity is determined using a LKB betaplate counter. The $IC_{50}$ value is determined using the equation:

$$\text{Bound} = B_{max}/(1+[l]/IC_{50})$$

wherein [l] means the concentration of the test compound.

All compounds prepared in the Examples described below were tested by this method and showed an $IC_{50}$ value of 0.1 nM to 21 nM in CHO-KL cells with respect to inhibition of binding at its receptor.

The most preferred compounds prepared in the working examples as described below were tested by this method and snowed an $IC_{50}$ value of 0.1 nM to 2.4 nM in CHO-K1 cells with respect to inhibition of binding at its receptor.

The possibility of drug—drug interactions of the 1,4-dihydropyridine compounds of the present invention, as bradykinin antagonists, is determined by their ability to inhibit the testosterone 6p-hydroxylase activity raised by CYP3A4 which is the most abundant subtype of cytochrome P-450 in human.

CYP3A4 Interaction Assay

This method essentially involves determining the concentration of the individual compound required to reduce the amount of 6p-hydroxytestosterone by 50%.

More specifically, the assay is carried out as follows. Human liver microsomes (0.2 mg/ml) are mixed with appropriate concentrations of kinin B2 antagonist. The mixture is then incubated in the presence of 50 μM testosterone, 1.3 mM NADP$^+$, 0.9 mM NADH, 3.3 mM glucose-6-phosphate, 3.3 mM MgCl$_2$, and glucose-6-phosphate dehydrogenase (8 units/ml) in a total volume of 0.2 ml of 100 mM potassium phosphate buffer, pH 7.4, at 37° C. After incubation (20 minutes), 10 μl of methylalchohol containing internal standard is withdrawn. The medium is filtrated by membrane filter with centrifugation at 1,800× g for 10 minutes, and the resulting filtrate is removed.

A 6β-hydroxylated metabolite of testosterone in samples is analyzed by HPLC. A sample of 20 μl is injected to the HPLC system equipped with a Polymer C18 column (2.0× 75 mm). The mobile phase consists of 24% to 66% acetonitorile linear gradient, including 10 mM of ammonium phosphate, with a flow rate of 0.35 ml/min.

The $IC_{50}$ value is determined using the equation:

Activity=Activity$_{control}$(1+[1]/IC$_{50}$)

wherein [1] means the concentration of the test compound.

The most preferred compounds among the title compounds of the Examples described below showed $IC_{50}$ values of less than 5 μM, preferably less than 1 μm, and more preferably less than 500 nM.

EXAMPLES

The present invention is illustrated by the following non-limiting examples in which, unless otherwise stated: all operations were carried out at room or ambient temperature, that is, in the range of 18–25° C.; evaporation of solvent was carried out using a rotary evaporator under reduced pressure with a bath temperature of up to 60° C.; reactions were monitored by thin layer chromatography (tic) and reaction times are given for illustration only; melting points (m.p.) given are uncorrected (polymorphism may result in different melting points); the structure and purity of all isolated compounds were assured by at least one of the following techniques: tic (Merck silica gel 60 $F_{254}$ precoated TLC plates or Merck $NH_2$ $F_{254}$, precoated HPTLC plates), mass spectrometry, nuclear magnetic resonance (NMR), infrared red absorption spectra (IR) or microanalysis. Yields are given for illustrative purposes only. Flash column chromatography was carried out using Merck silica gel 60 (230–400 mesh ASTM) or Fuji Silysia Chromatorex® DU3050 (Amino Type, 30–50 Em). Low-resolution mass spectral data (E1) were obtained on a Automass 120 (JEOL) mass spectrometer. Low-resolution mass spectral data (ESI) were obtained on a Quattro II (Micromass) mass spectrometer. NMR data was determined at 270 MHz (JEOL JNM-LA 270 spectrometer) or 300 MHz (JEOL JNM-LA300) using deuterated chloroform (99.8% D) or dimethylsulfoxide (99.9% D) as a solvent, unless otherwise indicated, relative to tetramethylsilane (TMS) as internal standard in parts per million (ppm). Conventional abbreviations used are: s=singlet, d=doublet, t=triplet, q=quartet, m=multiplet, br.= broad, etc. IR spectra were measured by a Shimazu infrared spectrometer (IR-470). Optical rotations were measured using a JASCO DIP-370 Digital Polarimeter (Japan Spectroscopic CO, Ltd.).

Chemical symbols have their usual meanings; b.p. (boiling point), m.p. (melting point), 1 (liter(s)), ml (milliliter(s)), g (gram(s)), mg (milligram(s)), mol (moles), mmol (millimoles), eq. (equivalent(s)).

Example 1

Dimethyl 2-(2-{2-[(2-aminoethoxy)methyl]phenyl}ethyl)-4-(2,6-dichlorophenyi)-6-{2-[4-(8-methyl-8-azabicyclo[3.2.1]oct-3-yl)-1-piperazinyl]-2-oxoethyl}-1,4-dihydro-3,5-pyridinedicarboxylate A. 2-[[2-(Chloromethyl)benzyl]oxy]-N-tritylethanamine A solution of 2-(triphenylmethylamino)ethanol (5.00 g, 16.5 mmol) in THF (20 ml) was added dropwise to a suspension of NaH (60% in oil, 0.79 g, 19.8 mmol) in THF (30 ml) at room temperature and the mixture was stirred for 0.5 hour. α,α-Dichloro-o-xylene (1.56 g, 66.0 mmol) was added and the mixture was stirred for 24 h at reflux temperature. The mixture was poured into water (50 ml) and the whole was extracted with ether (50 ml×2). The combined organic layers were washed with brine, dried over magnesium sulfate, and concentrated in vacuo. The residue was purified by column chromatography on silica gel (hexane/ethyl acetate=15/1 as eluent) to afford the titled compound as a colorless oil. (1.00 g, 14%)

$^1$H NMR (CDCl$_3$) δ: 7.49–7.10 (m, 9H), 4.66 (s, 2H), 4.57 (s, 2H), 3.61 (t, J=5.1 Hz, 2H), 2.36 (t, J=5.1 Hz, 2H) ppm.

B. Methyl 3-oxo-5-[2-[[2-(tritylamino)ethoxy]methyl]phenyl]pentanoate

NaH (60% in oil, 204 mg, 5.09 mmol) was added portionwise to a solution of methyl acetoacetate (0.55 ml, 5.09 mmol) in THF (20 ml) at 0° C. and the mixture was stirred for 30 min. n-BuLi (1.53 M in hexane, 3.3 ml, 5.09 mmol) was added dropwise and the mixture stirred for 30 minutes. 2-[[2-(Chlorometyl)benzyl]oxy]-N-tritylethylamine (1.50 g, 3.39 mmol) in THF (10 ml) was added dropwise at 0° C. and the mixture was stirred at ambient temperature. The mixture was quenched with sat. NaH$_2$PO$_4$aq. and extracted with ethyl acetate (40 ml×2). The combined organic layers were washed with brine, dried over MgSO$_4$, and evaporated in vacuum. The residue was purified by column chromatography on silica gel (hexane/ethyl acetate=15/1 as eluent) to afford the titled compound as a colorless oil. (511 mg, 29%)

$^1$H NMR (CDCl$_3$) δ: 7.50–7.12 (m, 19H), 4.45 (s, 2H), 3.68 (s, 3H), 3.61 (t, J=5.2 Hz, 2H), 3.32 (s, 2H), 2.96–2.76 (m, 4H), 2.37 (t, J=5.2 Hz, 2H) ppm.

C. Methyl3-(2,6-dichlorophenyl)-2-[3-[2-[[2-(tritylamino)ethoxy]methyl]phenyl]propanoyl]-2-propenoate A mixture of methyl 3-oxo-5-[2-[[2-(tritylamino)ethoxy]methyl]phenyl]pentanoate (3.33 g, 6.38 mmol), 2,6-dichlorobenzaldehyde (1.12 g, 6.38 mmol), acetic acid (0.5 ml), piperidine (0.5 ml) and benzene (50 ml) was stirred for 4 hours at reflux temperature azeotropically. The reaction mixture was quenched with water (40 ml) and the whole was extracted with Et$_2$O (20 ml×2). The combined extracts were washed with brine, dried over MgSO$_4$, and concentrated in vacuo to afford the titled compound as a yellow oil. (quant.)

$^1$H NMR (CDCl$_3$) δ: 7.63 (s, 0.5H), 7.59 (s, 0.5H), 7.50–7.10 (m, 22H), 4.49 (s, 1H), 4.40 (s, 1H), 3.68 (s, 3H), 3.84–3.55 (m, 5H), 3.12–2.31 (m, 6H) ppm.

D. Dimethyl 4-(2,6-dichlorophenyl)-2-(2-methoxy-2-oxoethyl)-6-[2-[2-[[2-(tritylamino)ethoxy]methyl]phenyl]ethyl]-1,4-dihydro-3,5-pyridinedicarboxylate To a stirred solution of 2-methyl-2-propanol (1.25 g, 16.9 mmol) in anhydrous THF (50 ml) was added dropwise a 0.95 M solution of MeMgBr in THF (17.8 ml, 16.0 mmol) at room temperature under nitrogen atmosphere. The resulting solution was stirred at room temperature for 0.5 hour. Then to the mixture was added a solution of dimethyl 3-amino-2-pentenedioate (1.33 g, 7.66 mmol) in anhydrous THF (20 ml) dropwise at room temperature. The resulting pale yellow solution was stirred at the same temperature for 0.5 hour, then a solution of methyl 3-(2,6-dichlorophenyl)-2-[3-[2-[[2-(tritylamino)ethoxy]methyl]phenyl]propanoyl]-2-propenoate (6.38 mmol) in anhydrous THF (20 ml) was added at room temperature. The reaction mixture was stirred at room temperature for 8 h under nitrogen atmosphere, then acetic acid (3 ml) was added. The resulting mixture was stirred at room temperature for 16 hours. The mixture was poured into water, and the whole was extracted with ethyl acetate (20 ml×2). The combined organic layers were washed with 2N-HClaq. (50 ml) and sat.NaHCO$_3$aq. (50 ml), dried over MgSO$_4$ and concentrated to afford a crude mixture. Purification on silica gel column chromatography eluted with hexane/EtOAc (3/1) to afford the titled compound as a yellow amorphous. (3.80 g, 85%).

$^1$H NMR (CDCl$_3$) δ: 7.48–7.14 (m, 22H), 6.99 (t, J=7.5 Hz, 1H), 5.97 (s, 1H), 4.63–4.45 (m, 2H), 3.74–3.50 (m, 13H), 3.04–2.78 (m, 4H), 2.45–2.35 (m, 2H) ppm.

E. [4-(2,6-Dichlorophenyl)-3,5-bis(methoxycarbonyl)-)-6-[2-[2-[[2-(tritylamino)ethoxy]methyl]phenyl]ethyl]-1,4-dihydro-2-pyridinyl]acetic acid To a stirred solution of dimethyl 4-(2,6-dichlorophenyl)-2-(2-methoxy-2-oxoethyl)-6-[2-[2-[[2-(tritylamino)ethoxy]methyl]phenyl]ethyl]-1,4-dihydro-3,5-pyridinedicarboxylate (3.80 g, 4.56 mmol) in MeOH (20 ml) and THF (20 ml) was added 2 N NaOHaq. (5 ml, 10 mmol). The reaction mixture was stirred at room temperature for 3 h. The mixture was acidified with 2 N HCl (5 ml) and sat.NaH$_2$PO$_4$aq (20 ml). The whole mixture was extracted with ethyl acetate (50 ml×2), the organic layers were washed with brine (50 ml), dried (MgSO$_4$) and then evaporated to afford the titled compound as a yellow amorphous. (3.60 g, 96%)

$^1$H NMR (CDCl$_3$) δ: 8.17 (s, 1H), 7.50–7.13 (m, 21H), 7.00 (t, J=7.0 Hz, 1H), 5.96 (s, 1H), 4.68 (d, J=16.0 Hz, 1H), 4.49 (d, J=16.0 Hz, 1H), 3.80–3.30 (m, 10H), 3.05–2.68 (m, 6H) ppm.

F. Dimethyl 4-(2,6-dichlorophenyl)-2-[4-(8-methyl-8-azabicyclo[3.2.1]oct-3-yl)-1-piperazinyl]-2-oxoethyl]-6-[2-[[2-(tritylamino)ethoxy]methyl]phenethyl]-1,4-dihydro-3,5-pyridinedicarboxylate To a solution of [4-(2,6-dichlorophenyl)-3,5-bis(methoxycarbonyl)-)-6-[2-[2-[[2-(tritylamino)ethoxy]methyl]phenyl]ethyl]-1,4-dihydro-2-pyridinyl]acetic acid (2.90 g, 3.54 mmol) in dichloromethane (40 ml) was added water soluble carbodiimide (0.81 g, 4.25 mmol) followed by 4-(8-methyl-8-azabicyclo[3.2.1]oct-3-yl)piperazine (0.89 g, 4.25 mmol) at ambient temperature, and then the resulting solution was stirred overnight. The solution was quenched with water (20 ml) and the whole was extracted with dichloromethane (50 ml×2). The combined extracts were washed with water (50 ml), dried over magnesium sulfate, filtered and concentrated. The residue was purified by column chromatography (NH$_2$ gel, dichloromethane/methanol=100:1) to afford the titled compound as a yellow amorphous. (2.60 g, 68%)

$^1$H-NMR (CDCl$_3$) δ: 8.17 (s, 1H), 7.48–6.95 (m, 22H), 5.99 (s, 1H), 4.58 (dd, J=1.8 Hz, 10.9 Hz, 2H), 4.13 (d, J=15.0 Hz, 1H), 3.72–3.50 (m, 11H), 3.28–3.17 (m, 4H), 2.99–2.81 (m, 4H), 2.60–2.31 (m, 7H), 2.27 (s, 3H), 2.04–1.96 (m, 2H), 1.80–1.47 (m, 6H) ppm.

G. Dimethyl 2-[2-[(2-aminoethoxy)methyl]phenethyl]-4-(2,6-dichlorophenyl)-2-[4-(8-methyl-8-azabicyclo[3.2.1]oct-3-yl)-1-piperazinyl]-2-oxoethyl]-1,4-dihydropyridine-3,5-dicarboxylate A mixture of dimethyl 4-(2,6-dichlorophenyl)-2-[4-(8-methyl-8-azabicyclo[3.2.1]oct-3-yl)-1-piperazinyl]-2-oxoethyl]-6-[2-[[2-(tritylamino)ethoxy]methyl]phenethyl]-1,4-dihydro-3,5-pyridinedicarboxylate (1.60 g, 1.48 mmol), p-TsOH-H$_2$O (0.90 g, 5.53 mmol), methanol (40 ml) and water (15 ml) was stirred for 6 h at reflux temperature. The reaction mixture was poured into sat.NaHCO$_3$aq., and the whole was extracted with dichloromethane (50 ml×3). The combined organic layers were wasted with brine, dried over MgSO$_4$, and evapolated in vacuum. The residue was purified on NH-gel, eluting with dichloromethane-methanol (30:1) to afford the titled product as a yellow amorphous. (0.95 g, 83%)

$^1$H-NMR (CDCl$_3$) δ: 8.40 (s, 1H), 7.39–7.15 (m, 6H), 7.00 (t, J=7.5 Hz, 1H), 6.00 (s, 1H), 4.63 (dd, J=11.3 Hz, 18.9 Hz, 2H), 4.04 (d, J=15.0 Hz, 1H), 3.80 (d, J=15.0 Hz, 1H), 3.66–3.52 (m, 12H), 3.20 (s, 2H), 3.30–2.132 (m, 6H), 2.66–2.44 (m, 5H), 2.27 (s, 3H), 2.06–1.96 (m, 8H) ppm.

H. Formation of Citric Acid Salt

A mixture of dimethyl 2-(2-{2-[(2-aminoethoxy)methyl]phenyl}ethyl)-4-(2,6-dichlorophenyl)-6-{2-[4-(8-methyl-8-azabicyclo[3.2.1]oct-3-yl)-1-piperazinyl]-2-oxoethyl}-1,4-dihydro-3,5-pyridinedicarboxylate (495 mg, 0.643 mmol) and citric acid (122 mg, 0.643 mmol) was dissolved in hot methanol (about 3 ml), then added about 9 ml ethanol. An off-white precipitate was occurred after adding suitable amount of diethyl ether. The precipitate was filtered and dried in vacuo to afford an off-white amorphous (473 mg) as the titled compound.

$^1$H-NMR (DMSO-d$_6$, 270 MHz) δ: 7.43–7.10 (m, 7H), 5.85 (s, 1H), 4.64 (s, 2H), 4.14 (d, J=16.0 Hz, 1H), 3.42 (s, 3H), 3.37 (s, 3H), 4.00–2.20 (m, 27H), 2.10–1.50 (m, 8H) ppm.

IR (KBr)σ$_{max}$: 3389, 2949, 1693, 1628–1570 (broad) cm$^{-1}$.

ES$^+$: 768.33 (M+1)
ES$^-$: 766.49 (M−1)

Example 2

Dimethyl 2-{2-[2-(2-aminoethoxy)phenyl]ethyl}-4-{2,6-dichlorophenyl)-6-{2-[4-(8-methyl-8-azabicyclo[3.2.1]oct-3-yl)-1-piperazinyl]-2-oxoethyl}-1,4-dihydro-3,5-pyridinedicarboxylate A. Methyl 3-[2-[2-(tritylamino)ethoxy)phenyl]propionate Diethyl azodicarboxylate (4.2 ml, 26.4 mmol) was added to a mixture of 2-(tritylamino)ethanol (6.08 g, 20.0 mmol), methyl 3-(2-hydroxyphenyl)propionate (5.00 g, 26.4 mmol), triphenylphosphine (6.91 g, 30.5 mmol) and THF (90 ml) at room temperature under nitrogen, and the mixture was standing for 20 hours at room temperature. The solvent was removed in vacuum. The residue was purified on SiO$_2$, eluting with ethyl acetate-hexane (1:15), to afford the titled product as a colorless oil. (5.88 g, 49%)

$^1$H-NMR (CDCl$_3$) δ: 7.79 (dd, J=1.8 Hz, 7.5 Hz, 1H), 7.56–7.39 (m, 7H), 7.32–7.15 (m, 9H), 7.03–6.90 (m, 2H), 4.15 (t, J=5.1 Hz, 2H), 3.69 (s, 3H), 2.60 (t, J=5.1 Hz, 2H) ppm.

B. Methyl 3-oxo-5-[2-[2-(tritylamino)ethoxy]phenyl]pentanoate

A mixture of methyl 3-[2-[3-(tritylamino)propoxy]phenyl]propionate (5.88 g, 12.6 mmol), 2N—NaOHaq. (13 ml, 26.0 mmol) and methanol (50 ml) was stirred for 5 hours at reflux temperature. The reaction mixture was quenched with sat.NaH$_2$PO$_4$aq. and extracted with ethyl acetate (30 ml×3). The combined extracts were washed with brine, dried over MgSO$_4$ and concentrated in vacuo. The residue was dissolved with THF (50 ml) and to the solution was added carbonyldiimidazole (2.45 g, 15.1 mmol). And then magnesium chloride (1.20 g, 12.6 mmol) and potassium methyl malonate (1.97 g, 12.6 mmol) were added. The mixture was stirred for 24 h at reflux temperature. The reaction mixture was quenched with 2N-HCl and extracted with ethyl acetate (100 ml×2). The combined extracts were washed with sat.NaHCO$_3$aq. and brine, dried over MgSO$_4$ and concentrated in vacuo. The residue was purified on SiO$_2$, eluting with ethyl acetate-hexane (1:4) to afford the titled product as a colorless oil. (4.60 g, 72%).

$^1$H NMR (CDCl$_3$) δ: 7.53–7.10 m, 17H), 6.89–6.78 (m, 2H), 4.084.03 (m, 2H), 3.61 (s, 3H), 3.24 (s, 2H), 2.90–2.75 (m, 4H), 2.61–2.54 (m, 2H) ppm.

C. Methyl3-(2,6-dichlorophenyl)-2-[3-(2-[2-(tritylamino)ethoxy]phenyl]propenoate This compound was prepared by a procedure similar to that described in example 1-C as a yellow amorphous.

$^1$H NMR (CDCl$_3$) δ: 7.60–6.73 (m, 23H), 4.12–4.00 (m, 2H), 3.69 (s, 1.5H), 3.52 (s, 1.5H), 3.12–2.53 (m, 6H) ppm.

D. Dimethyl4-(2,6-dichlorophenyl)-2-(2-methoxy-2-oxoethyl)-6-[2-[2-[2-(tritylamino)ethoxy]phenyl]ethyl]-1,4-dihydro-3,5-pyridinedicarboxylate This compound was prepared by a procedure similar to that described in example 1-D as a yellow amorphous.

¹H NMR (CDCl₃) δ: 7.57–7.11 (m, 19H), 7.01–6.80 (m, 3H), 6.52 (s, 1 h), 5.96 (s, 1H), 3.80–3.30 (m, 13H), 3.10–2.80 (m, 4H), 2.70–2.55 (m, 2H) ppm.

E. [4-(2,6-Dichlorophenyl)-3,5-bis(methoxycarbonyl)-)-6-[2-[2-[3-(tritylamino)propoxy]phenyl]ethyl]-1,4-dihydro-2-pyridinyl]acetic acid This compound was prepared by a procedure similar to that described in example 1-E as a yellow amorphous. This compound was used in next step without purification.

F. Dimethyl 4-(2,6-dichlorophenyl)-2-[4-(8-methyl-8-azabicyclo[3.2.1]oct-3-yl)-1-piperazinyl]-2-oxoethyl]-6-[2-[2-(tritylamino)ethoxy]phenethyl]-1,4-dihydro-3,5-pyridinedicarboxylate This compound was prepared by a procedure similar to that described in example 1-F as a yellow amorphous.

¹H NMR (CDCl₃) δ: 7.76 (s, 1H), 7.55–6.80 (m, 22H), 5.96 (s, 1H), 4.24–4.10 (m, 4H), 3.60–3.40 (m, 12H), 3.24–2.32 (m, 11H), 2.27 (s, 3H), 2.07–1.45 (m, 8H) ppm.

G. Dimethyl 2-[2-(2-aminoethoxy)phenetyl]-4-(2,6-dichlorophenyl)-6-[4-(8-methyl-8-azabicyclo[3.2.1]oct-3-yl)-1-piperazinyl]-2-oxoethyl]-1,4-dihydro-3,5-pyridinedicarboxylate This compound was prepared by a procedure similar to that described in example 1-G as a yellow amorphous.

¹H NMR (CDCl₃) δ: 8.16 (s, 1H), 7.29–7.13 (m, 4H), 7.03–6.81 (m, 3H), 5.98 (s, 1H), 4.20 (d, J=15.0 Hz, 1H), 4.08–4.01 (m, 2H), 3.69–3.51 (m, 11H), 3.23–3.13 (m, 4H), 2.98–2.88 (m, 4H), 2.63–2.43 (m, 5H), 2.27 (m, 3H), 2.04–1.47 (m, 8H) ppm.

Example 3

Dimethyl 2-{2-[2-(3-aminopropoxy)phenyl]ethyl}-4-(2,6-dichlorophenyl)-6-{2-[4-(8-methyl-8-azabicyclo[3.2.1]oct-3-yl)-1-piperazinyl]-2-oxoethyl}-1,4-dihydro-3,5-pyridinedicarboxylate A. Methyl 3-[2-[3-(tritylamino)propoxy]phenyl]propionate This compound was prepared by a procedure similar to that described in example 2-A as a colorless oil.

¹H-NMR (CDCl₃) δ: 7.50–7.10 (m, 17H), 6.90–6.80 (m, 2H), 4.09 (t, J=6.1 Hz, sH), 3.62 (s, 3H), 2.81 (t, J=7.5 Hz, 2H), 2.44 (t, J=7.5 Hz, 2H), 2.33 (t, J=6.7 Hz, 2H), 2.04–1.93 (m, 2H) ppm.

B. Methyl 3-oxo-5-[2-[3-(tritylamino)propoxy]phenyl] pentanoate

This compound was prepared by a procedure similar to that described in example 2-B as a colorless oil.

¹H NMR (CDCl₃) δ: 7.50–7.08 (m, 17H), 6.89–6.80 (m, 2H), 4.14–4.05 (m, 2H), 3.68 (s, 3H), 3.28 (s, 2H), 2.83–2.63 (m, 4H), 2.37–2.28 (m, 2H), 2.02–1.93 (m, 2H) ppm.

C. Methyl3-(2,6-dichlorophenyl)-2-[3-[2-[3-(tritylamino) propoxy]phenyl]propenoate This compound was prepared by a procedure similar to that described in example 1-C as a yellow amorphous.

¹H NMR (CDCl₃) δ: 7.64–6.75 (m, 23H), 4.15–4.00 (m, 2H), 3.81 (s, 1.5H), 3.58 (s, 1.5H), 3.10–2.70 (m, 4H), 2.40–2.25 (m, 2H), 2.05–1.90 (m, 2H) ppm.

D. Dimethyl 4-(2,6-dichlorophenyl)-2-(2-methoxy-2-oxoethyl)-6-[2-[2-[3-(tritylamino)propoxy]phenyl]ethyl]-1,4-dihydro-3,5-pyridinedicarboxylate This compound was prepared by a procedure similar to that described in example 1-D as a yellow amorphous.

¹H NMR (CDCl₃) δ: 7.48–7.13 (m, 18H), 7.03–6.83 (m, 3H), 6.64 (s, 1H), 5.97 (s, 1H), 4.21–4.13 (m, 2H), 3.62 (s, 3H), 3.60–3.51 (m, 8H), 2.89–2.69 (m, 4H), 2.40–2.32 (m, 2H), 2.11–2.00 (m, 2H) ppm.

E. [4-(2,6-Dichlorophenyl)-3,5-bis(methoxycarbonyl)-)-6-[2-[2-[3-(tritylamino)propoxy]phenyl]ethyl]-1,4-dihydro-2-pyridinyl]acetic acid This compound was prepared by a procedure similar to that described in example 1-E as a yellow amorphous.

¹H NMR (CDCl₃) δ: 8.41 (s, 1H), 7.48–6.68 (m, 22H), 3.93–3.87 (m, 2H), 3.70–3.40 (m, 8H), 2.97–2.50 (m, 6H), 2.38–2.25 (m, 2H) ppm.

F. Dimethyl 4-(2,6-dichlorophenyl)-2-[4-(8-methyl-8-azabicyclo[3.2.1]oct-3-yl)-1-piperazinyl]-2-oxoethyl]-6-[2-[3-(tritylamino)propoxy]phenethyl]-1,4-dihydro-3,5-pyridinedicarboxylate This compound was prepared by a procedure similar to that described in example 1-F as a yellow amorphous.

¹H NMR (CDCl₃) δ: 7.76 (s, 1H), 7.50–7.10 (m, 19H), 7.12–6.80 (m, 3H), 5.97 (s, 1H), 4.28–4.10 (m, 3H), 3.68–3.35 (m, 1OH), 3.32–3.15 (m, 3H), 2.90–2.30 (m, 11H), 2.27 (s, 3H), 2.19–1.95 (m, 4H), 1.80–1.43 (m, 6H) ppm.

G. Dimethyl 2-[2-(3-aminopropoxy)phenetyl]-4-(2,6-dichlorophenyl)-6-[4-(8-methyl-8-azabicyclo[3.2.1]oct-3-yl)-1-piperazinyl[-2-oxoethyl]-1,4-dihydro-3,5-pyridinedicarboxylate This compound was prepared by a procedure similar to that described in example 1-G as a yellow amorphous.

¹H NMR (CDCl₃) δ: 8.06 (s, 1H), 7.28–6.82 (m, 7H), 5.98 (s, 1H), 4.26–4.07 (m, 3H), 3.66–3.51 (m, 11H), 3.19 (s, 2H), 3.00–2.78 (m, 6H), 2.64–2.43 (m, 5H), 2.27 (s, 3H), 2.09–1.47 (m, 10H) ppm.

Example 4

Dimethyl 2-(2-{2-[(3-aminopropoxy)methyl]phenyl}ethyl)-4-(2,6-dichlorophenyl)-6-{2-[4-(8-methyl-8-azabicyclo [3.2.1]oct-3-yl)-1-piperazinyl]-2-oxoethyl)-1,4-dihydro-3,5-pyridinedicarboxylate A. 3-(Tritylamino)-1-propanol 3-(Tritylamino)-1-propanol was prepared according to the literature procedure (*J.Heterocycl.Chem.;* 1993, 30, 1197). To a solution of 3-amino-1-propanol (15.0 g/200 mmol) in THF (100 ml) was added a solution of tritylchloride (23.2 g/83.3 mmol) in THF (100 ml) dropwise at 0° C., and then the resulting solution was stirred at room temperature for 4 days. The solution was evaporated. The resulting residue was dissolved in water (100 ml) and dichloromethane (100 ml). The organic layer was separated. The aqueous layer was extracted with dichloromethane (100 ml×2). The combined organic layer was washed with brine (30 ml), dried over magnesium sulfate, filtered and concentrated. The residue was purified by recrystallization from toluene/hexane to afford a white crystal. (21.0 g/80%).

¹H NMR (CDCl₃) δ: 7.45–7.16 (m, 15H), 3.85 (t, J=5.5 Hz, 2H), 2.37 (t, J=6.0 Hz, 2 H), 1.72–1.65 (m, 2H) ppm.

B. 3-{[2-(Bromomethyl)benzyl]oxy}-N-trityl-1-propanamine

To a suspension of NaH (909 mg/22.7 mmol) in THF (50 ml) was added 3-(tritylamino)-1-propanol, and the solution was stirred at reflux temperature for 2 hours. To the solution was added α,α'-dibromo-o-xylene, and the solution was stirred at reflux temperature for 16 hours. After cooling, the mixture was poured into water. The whole was extracted with ethyl acetate (100 ml×2). The combined organic layer was washed with brine (30 ml), dried over magnesium sulfate, filtered and concentrated. The residue was purified by column chromatography (SiO$_2$, 200–350 mesh/hexane:ethyl acetate=100:0–20:1) to afford a yellow oil (4.84 g/51%).

$^1$H NMR (CDCl$_3$) δ: 7.47–7.15 (m, 19H), 4.61 (s, 2H), 4.50 (s, 2H), 3.61 (t, J=6.0 Hz, 2H), 2.24 (t, J=6.4 Hz, 2H), 1.87–1.78 (m, 2H) ppm.

C. Methyl 3-oxo-5-(2-{[3-(tritylamino)propoxy]methyl}phenyl)pentanoate

To a suspension of NaH (448 mg/1 1.2 mmol) in THF (22 ml) was added a solution of methyl acetoacetate (1.30 g/11.2 mmol) in THF (4.5 ml) dropwise at 0° C. over 15 minutes. After 20 minutes at 0° C., n-butyl lithium (7,3 ml/11.2 mmol) was added dropwise at 0° C. over 15 minutes. After 20 minutes at 0° C., a solution of 3-{[2-(bromomethyl)benzyl]oxy}-N-trityl-1-propanamine in THF (6.6 ml) was added dropwise at 0° C., and the solution was stirred at 0° C. for 3 hours. The mixture was quenched with water, and the whole was extracted with ethyl acetate (100 ml×2). The combined organic layer was washed with brine (30 ml), dried over magnesium sulfate, filtered and concentrated. The residue was dissolved in diethylether (100 ml) and hexane (100 ml). The solution was washed with water (50 ml×5), brine, dried over magnesium sulfate, filtered and concentrated. The residue was purified by column chromatography (SiO$_2$, 200–350 mesh/hexane:ethyl acetate=10:0–3:1) to afford a colorless oil (3.70 g/74%).

$^1$H NMR (CDCl$_3$) δ: 7.46–7.43 (m, 6H), 7.27–7.13 (m, 13H), 4.48 (s, 2H), 3.69 (s, 3H), 3.59 (t, J=6.4 Hz, 2H), 3.39 (s, 2H), 2.29–2.78 (m, 4H), 2.23 (t, J=6.4 Hz, 2H), 1.81–1.77 (m, 2H) ppm.

D. Methyl 3-(2,6-dichlorophenyl)-2-[3-(2-{[3-(tritylamino)propoxy]methyl}phenyl)propanoyl]-2-propenoate This compound was prepared by a procedure similar to that described in example 1-C as an orange oil.

$^1$H NMR (CDCl$_3$) δ: 7.62–7.04 (m, 22H), 4.52 (s, 1H), 4.42 (s, 1H), 3.81 (s, 1H), 3.63–3.54 (m, 5H), 3.14–2.80 (m, 4H), 2.21 (t, J=6.6 Hz, 2H), 1.84–1.75 (m, 2H) ppm.

E. Dimethyl4-(2,6-dichlorophenyl)-2-[2-(2-ethyl-3-{[3-(tritylamino)propoxy]methyl}phenyl)ethyl]-6-(2-methoxy-2-oxoethyl)-1,4-dihydro-3,5-pyridinedicarboxylate This compound was prepared by a procedure similar to that described in example 1-D as a yellow oil.

$^1$H NMR (CDCl$_3$) δ: 7.46–6.95 (m, 22H), 5.97 (s, 1H), 4.60 (dd, J=3.3, 11.5 Hz, 2H), 3.75–3.40 (m, 13H), 3.00–2.70 (m, 4H), 2.18 (t, J=6.8 Hz, 2H), 1.79 (t, J=6.8 Hz, 2H) ppm.

F. 2-[4-(2,6-Dichlorophenyl)-3,5-bis(methoxycarbonyl)-6-[2-(1,3-thiazol-2-yl)ethyl]-1,4-dihydro-2-pyridinyl]acetic acid This compound was prepared by a procedure similar to that described in example 1-E as a yellow oil, and used for next reaction without further purification.

G. Dimethyl 4-(2,6-dichlorophenyl)-2-{2-[4-(8-methyl-8-azabicyclo[3.2.1]oct-3-yl)-1-piperazinyl]-2-oxoethyl)-6-[2-(2-{[3-(tritylamino)propoxy]methyl}phenyl)ethyl]-1,4-dihydro-3,5-pyridinedicarboxylate This compound was prepared by a procedure similar to that described in example 1-F as a yellow oil.

$^1$H NMR (CDCl$_3$) δ: 7.46–6.95 (m, 22H), 5.99 (s, 1H), 4.60 (s, 2H), 4.08 (d, J=15.2 Hz, 1H), 3.72–3.53 (m, 9H), 3.19 (s, 2H), 2.96–2.82 (m, 4H), 2.60–2.45 (m, 5H), 2.27 (s, 3H), 2.26–1.50 (m, 16H) ppm.

H. Dimethyl 2-(2-{2-[(3-aminopropoxy)methyl]phenyl}ethyl)-4-(2,6-dichlorophenyl)-6-{2-[4-(8-methyl-8-azabicyclo[3.2.1]oct-3-yl)-1-piperazinyl]-2-oxoethyl}-1,4-dihydro-3,5-pyridinedicarboxylate A mixture of dimethyl 4-(2,6-dichlorophenyl)-2-{2-[4-(8-methyl-8-azabicyclo[3.2.1]oct-3-yl)-1-piperazinyl]-2-oxoethyl}-6-[2-(2-{[3-(tritylamino)propoxy]methyl}phenyl)ethyl]-1,4-dihydro-3,5-pyridinedicarboxylate (355 mg/0.346 mmol) and p-toluenesulfonic acid monohydrate (246 mg/1.29 mmol) in methanol (9.4 ml) and water (3.5 ml) was stirred at reflux temperature for 4 hours. After cooling, the mixture was poured into saturated NaHCO$_3$ aqueous solution. The whole was extracted with dichloromethane (100 ml×2). The combined organic layer was washed with brine (30 ml), dried over magnesium sulfate, filtered and concentrated. The residue was purified by column chromatography (NH$_2$ gel/200–350 mesh/dichloromethane:methanol=100:1–1100:2–100:5) to afford a yellow amorphous (190 mg/70%).

Free Base $^1$H-NMR (CDCl$_3$) δ: 7.32–6.97 (m, 7H), 5.99 (s, 1H), 4.62 (s, 2H), 4.13–4.05 (m, 1H), 3.79–3.53 (m, 9H), 3.35–3.21 (m, 4H), 2.95–2.77 (m, 6H), 2.61–2.49 (m, 5H), 2.28 (s, 3H), 2.05–1.51 (m, 12H) ppm.

HCl salt was prepared by a procedure similar to that described in example 1-H as a yellow solid.

mp 195–197° C.(dec.)

Example 5

Dimethyl 4-(2,6-dichlorophenyl)-2-2-[4-(8-methyl-8-azabicyclo[3.2.1]oct-3-yl)-1-piperazinyl]-2-oxoethyl}-6-{2-[(phenylsulfanyl)methyl]phenethyl)-1,4-dihydro-3,5-pyridinedicarboxylate A. Methyl 5-[2-({[tert-butyl(dimethyl)silyl]oxy}methyl)phenyl]-3-oxopentanoate This compound was prepared by a procedure similar to that described in example 1-B as a brown oil.

$^1$H NMR (CDCl$_3$) δ: 7.34–7.00 (m, 4H), 4.62 (s, 2H), 3.62 (s, 3H), 3.34 (s, 2H), 2.88–2.72 (m, 4H), 0.83 (s, 9H), 0.00 (s, 6H) pprn.

B. Methyl 2-{3-[2-({[tert-butyl(dimethyl)silyl]oxy}methyl)phenyl]propanoyl}-3-(2,6-dichlorophenyl)-2-propenoate This compound was prepared by a procedure similar to that described in example 1-C as a pale yellow oil.

$^1$H NMR (CDCl$_3$) δ: 7.53 (s, 0.5H), 7.51 (s, 0.5H), 7.34–6.50 (m, 7H), 4.66 (s, 1H), 4.58 (s, 1H), 3.75 (s, 1.5H), 3.51 (s, 1.5H), 3.10–2.68 (m, 4H), 0.82 (s, 9H), 0.00 (s, 6H) ppm.

C. Dimethyl 4-(2,6-dichlorophenyl)-2-{2-[2-(hydroxymethyl) phenyl]ethyl}-6-(2-methoxy-2-oxoethyl)-1,4-dihydro-3,5-pyridinedicarboxylate and Dimethyl 2-[2-(2-{[tert-butyl(dimethyl)silyl]oxy}phenyl)ethyl]-4-(2,6-dichlorophenyl)-6-(2-methoxy-2-oxoethyl)-1,4-dihydro-3,5-pyridinedicarboxylate These compounds were prepared by a procedure similar to that described in example 1-D.

Dimethyl 2-[2-(2-{[tert-butyl(dimethyl)silyl]oxyphenyl)ethyl]-4-(2,6-dichlorophenyl)-6-(2-methoxy-2-oxoethyl)-1,4-dihydro-3,5-pyridinedicarboxylate ¹H NMR (CDCl₃) δ:7.27–7.05 (m, 7H), 6.85 (t, J=6.8 Hz, 1H), 6.76 (brs, 1H), 5.82 (s, 1H), 4.73 (d, J=10.9 Hz, 1H), 4.64 (d, J=1.1.0 Hz, 1H), 3.54 (s, 3H), 3.43 (s, 3H), 3.37 (s, 3H), 3.37 (d, J=15.7 Hz, 1H), 3.19 (d, J=15.3Hz, 1H), 3.10–2.98 (m, 1H), 2.96–2.76 (m, 2H), 2.70–2.56 (m, 1H), 0.80 (s, 9H), 0.00 (s, 6H) ppm.

Dimethyl 4-(2,6-dichlorophenyl)-2-{2-[2-(hydroxymethyl) phenyl]ethyl}-6-(2-methoxy-2-oxoethyl)-1,4-dihydro-3,5-pyridinedicarboxylate ¹H NMR (CDCl₃) δ:7.57 (brs, 1H), 7.32–7.16 (m, 7H), 7.00 (t, J=6.9 Hz, 1H), 5.98 (s, 1H), 4.78 (s, 2H), 3.78 (d, J=14.7 Hz, 1H) 3.73 (s, 3H), 3.61 (d, J=14.8 Hz, 1H), 3.56 (s, 3H), 3.52 (s, 3H), 3.08–2.83 (m, 4H) ppm D. Dimethyl 4-(2,6-dichlorophenyl)-2-(2-methoxy-2-oxoethyl)-6-(2-{2-[(phenylsulfanyl)methyl]phenyl}ethyl)-1,4-dihydro-3,5-pyridinedicarboxylate To a mixture of dimethyl 4-(2,6-dichlorophenyl)-2-{2-[2-(hydroxymethyl) phenyl]ethyl}-6-(2-methoxy-2-oxoethyl)-1,4-dihydro-3,5-pyridinedicarboxylate (547 mg/1.0 mmol) and diphenyl disulfide (437 mg/2.0 mmol) in pyridine (8 ml) was added tri-n-butylphosphine (300 μl/1.2 mmol) at 0° C. and stirred for 18 hours at room temperature. The mixture was quenched by addition of water (10 ml) and extracted with ethyl acetate. The combined organic layer was washed with brine, dried over sodium sulfate, and concentrated in vacuo. The residue was; purified by column chromatography on silica gel (Hexane/Ethyl acetate=3/1) to afford dimethyl 4-(2,6-dichlorophenyl)-2-(2-methoxy-2oxoethyl)-6-(2-{2-[(phenylsulfanyl)methyl]phienyl}ethyl)-1,4-dihydro-3,5-pyridinedicarboxylate as a pale yellow amorphous (517.8 mg/81%,).

¹HNMR (CDCl₃) δ: 7.40–6.98 (m, 12H), 5.98 (s, 1H), 4.31 (d, 1H, J=11.9 Hz), 4.24 (d, 1H, J=11.9 Hz), 3.68 (d, 1H, J=16.8 Hz), 3.67 (s, 3H), 3.54 (s, 3H), 3.52 (s, 3H), 3.44 (d, 1H, J=16.8 Hz), 3.10–2.98 (m, 4H) ppm E. [4-(2,6-dichlorophenyl)-3,5-bis(methoxy carbonyl)-6-(2-{2-[(phenylsulfanyl)methyl]phenyl}ethyl)-1,4-dihydro-2-pyridinyl]acetic Acid This compound was obtained according to a similar manner to that of example 1-E as a yellow amorphous.

¹HNMR (CDCl₃) δ: 7.41–7.10 (m, 11H), 7.03 (t, 1H, J=7.5 Hz), 5.97 (s, 1H), 4.31 (d, 1H, J=11.9 Hz), 4.24 (d, 1H, J=11.9 Hz), 3.61 (s, 3H), 3.53 (s, 3H), 3.53 (d, 1H, J=13.6 Hz), 3.25 (d, 1H, J=13.6 Hz), 3.06–2.85 (m, 4H) ppm F. Dimethyl 4-(2,6-dichlorophenyl)-2-(2-{4-(8-methyl-8-azabicyclo[3.2.1]oct-3-yl)-1-piperazinyl]-2-oxoethyl}-6-{2-[(phenylsulfanyl)methyl]phenethyl}-1,4-dihydro-3,5-pyridinedicarboxylate This compound was obtained according to a similar manner to that of example 1-F as a yellow amorphous.

¹HNMR (CDCl₃) δ: 8.19 (s, 1H), 7.41–7.10 (m, 11H), 7.00 (t, 1H, J=7.9 Hz), 5.98 (s, 1H), 4.31 (d, 1H, J=12.0 Hz), 4.25 (d, 1H, J=12.0 Hz), 4.07 (d, 1H, J=15.3 Hz), 3.76 (d, 1H, J=15.3 Hz), 3.64–3.50 (m, 10H), 3.28–3.10 (m, 2H), 3.06–2.86 (m, 4H), 2.62–2.42 (m, 5H), 2.27 (s, 3H), 2.07–1.94 (m, 2H), 1.72–1.48 (m, 6H) ppm HCl salt was prepared by a procedure similar to that described in example 1-H as a yellow solid.

mp 218–220° C.(dec.)

IR (KBr)ν$_{max}$: 3170, 3080, 3000, 2436, 2364, 1707, 1684, 1647, 1616, 1506, 1458, 1429, 1290, 1215, 1180, 1109, 1049, 968, 765, 745 cm⁻¹.

¹H-NMR (DMSO-d6) δ 7.43–7.08 (m, 12H), 5.86 (s, 1H), 4.41 (d, 1H, J=12.5 Hz), 4.35 (d, 1H, J=12.5 Hz), 4.10–3.90 (br, 2H), 3.90–2.40 (m, 24H), 2.40–1.87 (m, 8H) ppm.

MS (m/z): 817 (M+H)⁺

Example 6

Dimethyl 4-(2,6-dichlorophenyl)-2-(2-(2-[3-(dimethylamino)propyl]phenylethyl)-6-{2-[4-(8-methyl-8-azabicyclo[3,2,1]oct-3-yl)-1-piperazinyl]-2-oxoethyl}-1,4-dihydro-3,5-pyridinecarboxylate A. Methyl 5-(2-iodophenyl)-3-oxopentanoate This compound was prepared by a procedure similar to that described in example 1-B as a brown oil. This product was used for next step without purification.

B. Methyl 3-(2,6-dichlorophenyl)-2-[3-(2-iodophenyl) propanoyl]-2-propenoate

This compound was prepared by a procedure similar to that described in example 1-C as a brown oil.

¹HNMR (CDCl₃) 7.82 (d, J=8.0 Hz, 0.5H), 7.75 (d, J=7.9 Hz. 0.5H), 7.63 (s, 1H), 7.36–7.14 (m, 5H), 3.65 (s, 1.5H), 3.63 (s, 1.5H), 3.14 (s, 1.5H), 2.97 (s, 1.5H) ppm C. Dimethyl 4-(2,6-dichlorophenyl)-2-[2-(2-iodophenyl) ethyl]-6-(2-methoxy-2-oxoethyl)-1,4-dihydro-3,5-pyridinedicarboxylate This compound was prepared by a procedure similar to that described in example 1-D as a brown oil.

¹HNMR (CDCl₃) 7.79 (d, J=7.1 Hz, 1H), 7.38–7.20 (m, 2H), 7.23 (d, J=6.8 Hz, 2H), 7.04–6.50 (m, 2H), 6.88 (t, J=7.3 Hz, 1H), 5.97 (s, 1H), 3.82 (d, J=16.9 Hz, 1H), 3.69 (d, J=15.9 Hz, 1H), 3.72 (s, 3H), 3.54 (s, 3H), 3.52 (s, 3H), 3.06–2.70 (m, 4H) ppm D. Dimethyl 4-(2,6-dichlorophenyl)-2-(2-{2-[3-(dimethylamino)-1-propynyl]phenyl}ethyl)-6-(2-methoxy-2-oxclethyl)-1,4-dihydro-3,5-pyridinedicarboxylate A mixture of dimethyl 4-(2,6-dichlorophenyl)-2-[2-(2-iodophenyl)ethyl]-6-(2-methoxy-2-oxoethyl)-1,4-dihydro-3,5-pyridinedicarboxylate (11.721 g, 18.23 mmol), N,N-dimethyl-N-(2-propynyl)amine (10 ml), PdCl₂(PPh₃)₂ (686 mg) and CuI (449 mg) in triethylamine (90 ml) was heated at 75° C. for 19 hours. The mixture was then cooled to room temperature and filtered through a pad of celite. The filtrate was diluted with CH₂Cl₂ (400 ml) and washed with brine, then dried over MgSO₄ and concentrated in vacuo. Flash column chromatography of the residue [silica gel 300 g, CH₂Cl₂/MeOH (100/1 to 20/1) as eluent]afforded the desired product 8.195 g (75% yield) as a yellow amorphous.

¹H NMR (CDCl₃, 270 MHz) δ: 7.44.-7.12 (m, 6H), 7.00 (t, J=7.9 Hz, 1H), 6.01 (s, 1 H), 3.82 (d, J=16.6 Hz, 1H), 3.72 (s, 3H), 3.63 (d, J=16.6 Hz, 1H), 3.57 (s, 3H), 3.53 (s, 3 H), 3.45 (s, 2H), 3.72–2.75 (m, 4H), 2, 37 (s, 6H) ppm.

E. Dimethyl4-(2,6-dichlorophenyl)-2-(2-{2-[3-(dimethylamino)propyl]phenyl}ethyl)-6-(2-methoxy-2-oxoethyl)-1,4-dihydro-3,5-pyridinedicarboxylate A mixture of dimethyl 4-(2,6-dichlorophenyl)-2-(2-{2-[3-(dimethylamino)-1-propynyl]phenyl}ethyl)-6-(2-methoxy-2-oxo(thyl)-1,4-dihydro-3,5-pyridinedicarboxylate (8.195 g, 13.67 mmol) and 10% palladium on carbon (4.1 g) in AcOEt (140 ml) was stirred under hydrogen atmosphere by balloon for 15 hours. Catalyst was removed by filtration and the filtrate was concentrated by evaporation. Flash column chromatography of the residue [silica gel 150 g, CH₂Cl₂/MeOH (100/1 to 10/1) as eluent]afforded the desired product 4.31 g (52% yield) as a yellow amorphous.

¹H NMR (CDCl₃, 270 MHz) δ: 7.52 (bv, 1H), 7.35–7.10 (m, 6H), 7.00 (t, J=8.0 Hz, 1H), 6.01 (s, 1H), 3.83 (d, J=16.9 Hz, 1H), 3.73 (s, 3H), 3.68 (d, J=16.9 Hz, 1H), 3.57 (s, 3H), 3.53 (s, 3H), 3.02–2.66 (m, 6H), 2.44–2.34 (m, 2H), 2.23 (s, 6H), 1.83–1.72 (m, 2 H) ppm.

F. [4-(2,6-dichlorophenyl)-6-(2-{2-[3-(dimethylamino) propyl]phenyl}ethyl)-3,5-bis(methoxycarbonyl)-1,4-dihydro-2-pyridinyl]acetic acid To a solution of dimethyl 4-(2,6-dichlorophenyl)-2-(2-{2-[3-(dimethylamino)propyl]phenyl}ethyl)-6-(2-methoxy-2-oxoethyl)-1,4-dihydro-3,5-pyridinedicarboxylate (4.31 g, 7.14 mmol) in 1,4-dioxane (61 ml) was added 2N NaOH. The reaction mixture was stirred at room temperature for 2.5 h. The residual 1,4-dioxane was removed by evaporation in vacuo. The residue was diluted with water (19 ml) and washed with diethyl ether (50 ml×2) and AcOEt (20 ml). The water phase was then acidified with aq. $NaH_2PO_4$ to about pH 5. The whole was extracted with $CH_2Cl_2$ (300 ml×3). The combined extract was washed with brine, dried over $MgSO_4$, and concentrated to afford the desired acid (4.30 g, 90% yield) as a yellow amorphous.

$^1H$ NMR ($CDCl_3$, 300 MHz) δ: 9.82 (bv, 1H), 7.43–7.06 (m, 6H), 6.98 (t, J=8.0 Hz, 1H), 6.01 (s, 1H), 4.04 (d, J=16.7 Hz, 1H), 3.66 (d, J=16.7 Hz, 1H), 3.58 (s, 3H), 3.54 (s, 3H), 3.16–2.74 (m, 8H), 2.83 (s, 6H), 2.14–2.00 (m, 2H) ppm.

G. Dimethyl 4-(2,6-dichlorophenyl)-2-(2-{2-[3-(dimethylamino)propyl]phenyl}ethyl)-6-{2-[4-(8-methyl-8-azabicyclo[3,2,1]oct-3-yl)-1-piperazinyl]-2-oxoethyl}-1,4-dihydro-3,5-pyridinecarboxylate This compound was obtained according to a similar manner to that of example 1-F as a yellow amorphous. $^1H$ NMR ($CDCl_3$, 300 Hz) δ: 8.25 (brs, 1H), 7.40–7.10 (m, 6H), 7.00 (t, J=7.9 Hz, 1H), 5.99 (s, 1H), 4.18 (d, J=15.0 Hz, 1H), 3.72 (d, J=15.0 Hz, 1H), 3.70–3.56 (m, 4H), 3.55 (s, 3H), 3.54 (s, 3H), 3.26–3.16 (m, 2H), 3.00–2.30 (m, 13H), 2.27 (s, 3H), 2.22 (s, 6H), 2.15–1.45 (m, 10H) ppm.

IR (KBr)$v_{max}$: 3219, 3096, 2945, 2862, 2810, 1697, 1632, 1562 $cm^{-1}$.

MS (m/z): 780 $(M+H)^+$

Example 7 dimethyl 4-(2,6-dichlorophenyl)-2-(2-{2-[(diethylamino)methyl]phenyl}ethyl)-6-{2-[4-(8-methyl-8-azabicyclo[3.2.1]oct-3-yl)-1-piperazinyl]-2-oxoethyl}-1,4-dihydro-3,5-pyridinedicarboxylate A. [2-(1,3-Diaxan-2-yl)phenyl]mathanol To a solution of 2-(1,3-dioxan-2-yl)bezaldehyde (20.0 g, 104 mmol, Tetrahedron, 47, 8687 (1991)) in methanol (300 ml).was added portionwise $NaBH_4$ (7.87 g, 208 mmol) at 0° C. and the mixture was stirred for 1 hour. The reaction mixture was quenched with water (100 ml) and extracted with ethyl acetate (200 ml×2). The combined extracts were washed with brine, dried over $MgSO_4$ and concentrated in vacuo. The residue was purified on $SiO_2$, eluting with ethyl acetate-hexane (4:5) to afford the titled compound as a colorless oil. (15.7 g, 78%)

$^1H$ NMR ($CDCl_3$) δ: 7.56–7.29 (m, 4H), 5.69 (s, 1H), 4.75 (d, J=6.8 Hz, 2H), 4.35–3.98 (m, 4H), 3.17–3.08 (m, 1H), 2.38–2.20 (m, 1H), 1.54–1.47 (m, 1H) ppm.

B. 2-(1,3-Dioxan-2-yl)benzyl methanesulfonate

To a solution of [2-(1,3-diaxan-2-yl)phenyl]mathanol (15.7 g, 80.8 mmol). and triethyamine (11.3 ml, 80.8 mmol) in dichloromethane (300 ml) was added dropwise methane-sulfonylchloride (6.3 ml, 80.8 mmol) at 0° C. and the mixture was stirred for 30 minutes. The reaction mixture was quenched with water (150 ml) and extracted with dichloromethane (50 ml×2). The combined extracts were washed with brine, dried over $MgSO_4$ and concentrated in vacuo to afford the titled compound as a white solid. (quant)

$^1H$ NMR ($CDCl_3$) δ: 7.63–7.38 (m, 4H), 5.69 (s, 1H), 5.51 (s, 2H), 4.31–3.98 (m, 4H), 2.91 (s, 3H), 2.35–2.19 (m, 1H), 1.53–1.43 (m, 1H) ppm.

C. Methyl 5-[2-(1,3-dioxan-2-yl)phenyl]-3-oxopentanoate

This compound was prepared by a procedure similar to that described in example 1-B as a yellow amorphous.

$^1H$ NMR ($CDCl_3$) δ 7.60–7.13 (m, 4H), 5.62 (s, 1H), 4.29–3.91 (m, 4H), 3.73 (s, 3H), 3.44 (s, 2H), 309–2.83 (m, 4H), 2.33–2.15 (m, 1H), 1.50–1.40 (m, 1H) ppm.

D. Methyl 3-(2,6-dichlorophenyl)-2-[2-(1,3-dioxan-2-yl)phenyl]propanate

This compound was prepared by a procedure similar to that described in example 1-C as a yellow amorphous.

$^1H$ NMR ($CDCl_3$) δ: 7.52–7.05 (m, 8H), 5.67 (s, 0.5H), 5.59 (s, 0.5H), 4.34–3.90 (m, 4H), 3.85 (s, 1.5H), 3.62 (s, 1.5H), 3.15 (s, 2H), 2.96 (s, 2H), 2.34–2.15 (m, 1H), 1.47–1.36 (m, 1H) ppm.

E. Dimethyl4-(2,6-dichlorophenyl)-2-(2-methoxy-2-oxoethyl)-6-[2-(2-formylphenyl)ethyl]-1,4-dihydro-3,5-pyridinedicarboxylate (Dimethyl 4-(2,6-dichlorophenyl)-2-(2-methoxy-2-oxoethyl)-6-[2-(1,3-dioxan-2-yl)phenyl]ethyl]-1,4-dihydro-3,5-pyridinedicarboxylate)

A mixture (1:1) of dimethyl 4-(2,(3-dichlorophenyl)-2-(2-methoxy-2-oxoethyl)-6-[2-(2-formylphenyl)ethyl]-1,4-dihydro-3,5-pyridinedicarboxylate and dimethyl 4-(2,6-dichlorophenyl)-2-[2-methoxy-2-oxoethyl)-6-[2-(1,3-dioxan-2-yl) phenyl]ethyl]-1,4-dihydro-3,5-pyridinedicarboxylate was prepared by a procedure similar to that described in example 1-D as a yellow amorphous.

$^1H$ NMR ($CDCl_3$)

Dimethyl 4-(2,6-dichlorophenyl)-2-(2-methoxy-2-oxoethyl)-6-[2-(2-formylphenyl)ethyl]-1,4-dihydro-3,5-pyridine(dicarboxylate δ 10.10 (s, 1H), 7.84 (s, 1H), 7.60–6.90 (m, 7H), 6.02 (s, 1H), 4.30–3.45 (m, 11H), 3.35–2.60 (m, 4H) ppm.

Dimethyl 4-(2,6-dichlorophenyl)-2-(2-methoxy-2-oxoethyl)-6-[2-(1,3-dioxan-2-yl)phenyl]ethyl]-1,4-dihydro-3,5-pyridinedicarboxylate δ 7.61–7.56 (m, 1H), 7.30–7.19 (m, 5H), 7.02–6.95 (m, 1H), 5.95 (s, 1H), 5.79 (s, 1H), 4.35–4.00 (m, 4H), 3.67 (s, 3H), 3.61 (d, J=16.6 Hz, 1H), 3.58 (s, 3H), 3.50 (s, 3H), 3.21 (d, J 16.6 Hz, 1H), 3.16–3.05 (m, 3H), 2.83–2.70 (m, 1H), 2.38–2.20 (m, 1H), 1.55–1.45 (m, 1H) ppm.

F. Dimethyl2-[2-[4-[[1-(amino methyl)cyclohexyl]methyl]-1-piperazinyl]-2-oxoethyl]-4-(2,6-dichlorophenyl)-6-[2-(diethylaminomethyl)phenethyl]-1,4-dihydro-3,5-pyridinedicarboxylate $NaBH(OAc)_3$ (0.71 g, 3.34 mmol) was added to a mixture (1:1) of dimethyl 4-(2,6-dichlorophenyl)-2-(2-methoxy-2-oxoethyl)-6-[2-(2-formylphenyl)ethyl]-1,4-dihydro-3,5-pyridined icarboxylate and dimethyl 4-(2,6-, dichlorophenyl)-2-(2-methoxy-2-oxoethyl)-6-[2-(1,3-dioxan-2-yl)phenyl]ethyl]-1,4-dihydro-3,5-pyridinedicarboxylate (0.80 g, 1.39 mmol) and diethylamine (0.17 ml, 1.67 mmol) in 1,2-dichloroethane (10 ml) in one portion and the mixture was stirred for 2 h. The reaction mixture was quenched with water and the whole was extracted with dichloromethane (10 ml×2). The combined extracts were washed with brine, dried over $MgSO_4$, and concentrated in vacuo. The residue was purified on $SiO_2$, eluting with dichloromethane-methanol (15:1), to afford the titled compound as a yellow amorphous. (280 mg, 33%)

$^1H$ NMR ($CDCl_3$) δ: 8.83 (s, 1H), 7.52–6.96 (m, 7H), 6.02 (s, 1H), 4.22–3.88 (m, 3H), 3.75–3.65 (m, 4H), 3.55 (s, 3H), 3.51 (s, 3H), 3.30–2.86 (m, 8H), 1.36 (t, J=7.2 Hz, 6H) ppm.

G. [4-(2,6-Dichlorophenyl)-3,5-bis(methoxycarbonyl)-)-6-[2-(diethylaminomethyl)phenethyl]-1,4-dihydro-2-pyridinyl]acetic acid This compound was prepared by a procedure similar to that described in example 1-E as a yellow amorphous.

$^1$H NMR (CDCl$_3$) δ: 9.31 (s, 1H), 7.55–6.93 (m, 7H), 5.91 (s, 1H), 4.44–4.20 (m, 2H), 4.04–3.58 (m, 2H), 3.52 (s, 3H), 3.44 (s, 3H), 3.30–2.95 (m, 8H), 1.39 (t, J=7.1 Hz, 6H) ppm.

H. Dimethyl 4-(2,6-dichlorophenyl)-2-[4-(8-methyl-8-azabicyclo[3.2.1]oct-3-yl)-1-piperazinyl]-2-oxoethyl]-6-[2-(diethylaminomethyl)phenethyl]-1,4-dihydro-3,5-pyridinedicarboxylate This compound was prepared by a procedure similar to that described in example 1-F as a yellow amorphous.

$^1$H NMR (CDCl$_3$) δ: 8.02 (s, 1H), 7.34–6.97 (m, 7H), 6.00 (s, 1H), 4.13 (d, J=15.0 Hz, 1H), 3.78–3.49 (m, 13H), 3.20 (s, 2H), 3.04–2.80 (m, 4H), 2.68–2.44 (m, 9H), 2.07–1.96 (m, 2H), 1.73–1.48 (m, 6H) ppm.

HCl salt was prepared by a procedure similar to that described in example 1-H as a yellow solid.

mp: 77–79° C. (dec.)

IR (KBr)Γ$_{max}$: 2945, 1697, 1635, 1508, 1288, 1101, 768 cm$^{-1}$.

MS (m/z) 780 (M+H)$^+$

Example 8

Dimethyl 4-(2,6-dichlorophenyl)-2-[2-(2-hydroxyphenyl)ethyl]-6-{2-[4-(8-methyl-8-azabicyclo[3.2.1]oct-3-yl)-1-piperazinyl]-2-oxoethyl}-1,4-dihydro-3,5-pyridinedicarboxylate A tert-Butyl[2-({[tert-butyl(dimethyl)silyl]oxy}methyl)phenoxy]dimethylsilane To a solution of 2-hydroxybenzyl alcohol (5.0 g/40.3 mmol) in DMF (44 ml) was added tert-butyldimethylsilyl chloride (14.6 g/96.7 mmol), imidazole (6.58 g/96.7 mmol), and then the resulting solution was stirred at room temperature for 2 hours. The mixture was poured into water. The whole was extracted with ethyl acetate (100 ml×4). The combined organic layer was washed with water (100 ml×4), brine (30 ml), dried over magnesium sulfate, filtered and concentrated. The compound was used for next reaction without further purification. (15.6 g/99%).

$^1$H NMR (CDCl$_3$) δ: 7.35 (d, J=7.2 Hz, 1H), 7.14–6.94 (m, 2H), 6.75 (d, J=7.9 Hz, 1H), 4.76 (s, 2H), 1.01 (s, 9H), 0.95 (s, 9H), 0.21 (s, 6H), 0.10 (s, 6H) ppm.

B. (2-{[tert-Butyl(dimethyl)silyl]oxy}phenyl)methanol (2-{[tert-Butyl(dimethyl)silyl]oxy}phenyl)methanol was prepared according to the literature procedure (*Tetrahedron Lett.*; 1998, 39, 5249). To a solution of tert-butyl[2-({[tert-butyl(dimethyl)silyl]oxy}methyl)phenoxy]diimethylsilane (14.2 g/40.3 mmol) in methanol (403 ml) was added carbon tetrabromide (1.34 g/4.03 mmol), and then the resulting solution was stirred at reflux temperature for 3 hours. After cooling, the solvent was evaporated. The residue was purified by column chromatography (SiO$_2$, 200–350 mesh/hexane:ethyl acetate=20:1) to afford a colorless oil (9.90 g/99%), $^1$H NMR (CDCl$_3$) 3: 7.30 (d, J=7.3 Hz, 1H), 7.21–7.16 (m, 1H), 6.98–6.93 (m, 1H), 6.82 (d, J=8.0 Hz, 1H), 4.68 (d, J=6.2 Hz, 2H), 1.03 (s, 9H), 0.27 (s, 6H) ppm.

C. [2-(Bromomethyl)phenoxy](tert-butyl)dimethylsilane

[2-(Bromomethyl)phenoxy](tert-butyl)dimethylsilane was prepared according to the literature procedure (*J. Chem. Soc. Perkin Trans.*1; 1988; 1417). To a solution of (2-([tert-butyl(dimethyl)silyl]oxy}phenyl)methanol (9.9 g/41.5 mmol) in acetonitrile (200 ml) was added carbon tetrabromide (14.5 g/43.6 mmol), triphenylphosphine (11.4 g/43.6 mmol) successively at 0° C., and then the resulting solution was stirred at room temperature for 16 hours. The solvent was evaporated. The residue was purified by column chromatography (SiO$_2$, 200–350 mesh/hexane:ethyl acetate=100:1–20:1–10:1) to afford a colorless oil (12.0 g/96%).

$^1$H NMR (CDCl$_3$) δ: 7.57 (d, J=7.5 Hz, 1H), 7.46–7.14 (m, 2H), 7.05 (d, J=8.0 Hz, 1H), 4.78 (s, 2H), 1.30 (s, 9H), 0.53 (s, 6H) ppm.

D. Methyl 5-(2-{[tert-butyl(dimethyl)silyl]oxy}phenyl)-3-oxopentanoate

This compound was prepared by a procedure similar to that described in example 1-B as a yellow oil.

$^1$H NMR (CDCl$_3$) δ: 7.14–7.07 (m, 2H), 6.90–6.77 (m, 2H), 3.72 (s, 3H), 3.42 (s, 2H), 2.90–2.82 (m, 4H), 1.00 (s, 9H), 0.24 (s, 611) ppm.

E. 2-[3-(2-{[tert-Butyl(dimethyl)silyl]oxy}phenyl)propanoyl]-3-(2,6-dichlorophenyl)-2-propenoate This compound was prepared by a procedure similar to that described in example 1-C as a yellow oil, and used for next reaction without further purification.

F. Dimethyl 2-[2-(2-{[tert-butyl(dimethyl)silyl]oxy}phenyl)ethyl]-4-(2,6-dichlorophenyl)-6-(2-methoxy-2-oxoethyl)-1,4-dihydro-3,5-pyridinedicarboxylate This compound was prepared by a procedure similar to that described in example 1-D as a yellow oil.

$^1$H NMR (CDCl$_3$) δ: 7.27–6.78 (m, 6H), 6.52 (s, 1H), 5.98 (s, 1H), 3.70 (s, 3H), 3.59 (d, J=2.6 Hz, 2H), 3.55 (s, 3H), 3.52 (s, 3H), 3.00–2.86 (m, 4H), 1.03 (s, 9H), 0.27 (s, 3H), 0.24 (s, 3H) ppm.

G. [6-[2-(2-{[tert-Butyl(dimethyl)silyl]oxy}phenyl)ethyl]-4-(2,6-dichlorophenyl)-3,5-bis(methoxycarbonyl)-1,4-dihydro-2-pyridinyl]acetic Acid This compound was prepared by a procedure similar to that described in example 1-E as a yellow oil.

The compound was used for next reaction without further purification.

H. Dimethyl 4-(2,6-dichorophenyl)-2-[2-(2-hydroxyphenyl)ethyl]-6-{2-[4-(8-methyl-8-azabicyclo[3.2.1]oct-3-yl)-1-piperazinyl]-2-oxoethyl}-1,4-d ihydro-3,5-pyridinedicarboxylate This compound was prepared by a procedure similar to that described in example 1-G as a yellow oil.

Free Base $^1$H-NMR (CDCl$_3$) δ: 8.33 (s, 1H), 7.27–6.78 (m, 6H), 5.98 (s, 1H), 4.11 (d, J=14 Hz, 1H), 3.87 (d, J=14 Hz, 1H), 3.65–3.62 (m, 5H), 3.58 (s, 3H), 3.54 (s, 3H), 3.21 (s, 2H), 3.01–2.83 (m, 3H), 2.63–2.49 (m, 6H), 2.28 (s, 3H), 2.04–1.99 (m, 2H), 1.73–1.51 (m, 5H) ppm.

HCl salt was prepared by a procedure similar to that described in example 1-H as a yellow solid.

mp 270–272° C.(dec.)

Example 9

Dimethyl 4-(2,6-dichlorophenyl 1-2-[2-[4-(8-methyl-8-azabicyclo[3.2.1]oct-3-yl)-1-piperazinyl]-2-oxoethyl]-6-[2-[2-(4-morptiolinylmethyl)phenyl]ethyl]-1,4-di hydro-3,5-pyridinedicarboxylate A. Dimethyl 2-[2-[4-[[1-(aminomethyl)cyclohexyl]methyl]-1-piperazinyl]-2-oxoethyl]-4-(2,6-dichlorophenyl)-6-[2-[2-(4-morpholinylmethyl)phenyl]ethyl]-1,4-dihydro-3,5-pyridinedicarboxylate This compound was prepared by a procedure similar to that described in example 7-E as a yellow amorphous.

$^1$H NMR (CDCl$_3$) δ: 7.32–6.98 (m, 8H), 6.00 (s, 1H), 3.74–3.47 (m, 14H), 3.09–2.88 (m, 4H), 2.53–2.43 (m, 4H) ppm.

B. [4-(2,6-Dichlorophenyl)-3, 5)-bis(methoxycarbonyl)-)-6-[2-[2-(4-morpholinylmethyl)phenyl]ethyl]-1,4-dihydro-2-pyridinyl]acetic Acid This compound was prepared by a procedure similar to that described in example 1-E as a yellow amorphous.

$^1$H NMR (CDCl$_3$) δ: 8.89 (s, 1H), 7.56–6.93 (m, 7H), 5.91 (s, 1H), 4.41–4.30 (m, 2H), 4.00–3.80 (m, 6H), 3.70–3.40 (m, 8H), 3.20–2.75 (m, 8H) ppm.

C. Dimethyl 4-(2,6-dichlorophenyl)-2-[4-(8-methyl-8-azabicyclo[3.2.1]oct-3-yl)-1-piperazinyl]-2-oxoethyl]-6-[2-[2-(4-morpholinylmethyl)phenyl]ethyl]-1,4-dihydro-3,5-pyridinedicarboxylate This compound was prepared by a procedure similar to that described in example 1-F as a yellow amorphous.

$^1$H NMR (CDCl$_3$) δ: 8.18 (s, 1H), 7.33–6.98 (m, 7H), 6.00 (s, 1H), 4.26 (d, J=15.0 Hz, 1H), 3.70–3.50 (m, 17H), 3.20 (s, 2H), 3.05–2.84 (m, 4H), 2.63–2.43 (m, 9H), 2.27 (s, 3H), 2.09–1.48 (m, 8H) ppm.

HCl salt was prepared by a procedure similar to that described in example 1-H as a yellow solid.

mp: 85–87° C. (dec.)

IR (KBr)ν$_{max}$: 2947, 1697, 1632, 1499, 1288, 1115, 768 cm$^{-1}$.

MS (m/z): 794 (M+H)$^+$

Example 10

Dimethyl 4-(2,6-dichlorophenyl)-2-{2-[4-(8-methyl-8-azabicyclo[3.2.1]oct-3-yl)-1-piperazinyl]-2-oxoethyl}-6-(2-{2-[(methylsulfonyl)amino]phenyl}ethyl)-1,4-dihydro-3,5-pyridinedicarboxylate A. Methyl 5-(2-nitrophenyl)-3-oxopentanoate 3-(2-Nitrophenyl)propanoic acid was prepared according to the literature procedure[Latv. Kim. Z. 4, 449–450 (1993)] This compound was prepared by a procedure similar to that described in example 3-B $^1$H NMR (CDCl$_3$) δ: 8.00–7.90 (m, 1H), 7.60–7.30 (m, 3H), 3.73 (s, 3H), 3.47 (s, 2H), 3.18 (t, J=7.3 Hz, 2H), 2.98 (t, J=7.3 Hz, 2H) ppm.

B. Methyl (2E, 2Z)-3-(2,6-dichlorophenyl)-2-[3-(2-nitrophenyl)propanoyl]-2-propenoate This compound was prepared by a procedure similar to that described in example 1-C $^1$H NMR (CDCl$_3$) δ: 8.00–7.86 (m, 1H), 7.65 and 7.63 (each s, total 1H), 7.60–7.15 (m, 6H), 3.86 and 3.62 (each s, total 3H), 3.35–3.05 (m, 4H) ppm C. Dimethyl 4-(2,6-dichlorophenyl)-2-(2-methoxy-2-oxoethyl)-6-[2-(2-nitrophenyl)ethyl]-1,4-dihydro-3,5-pyridinedicarboxylate This compound was prepared by a procedure similar to that described in example 1-D.

$^1$H NMR (CDCl$_3$) δ: 8.02–7.95 (m, 1H), 7.60–7.52 (m, 2H), 7.45–7.34 (m, 1H), 7.30–7.23 (m, 2H), 7.05–6.95 (m, 2H), 6.00 (s, 1H), 3.99 (d, J=16.9 Hz, 1H), 3.77 (s, 3H), 3.65 (d, J=16.9 Hz, 1H), 3.57 (s, 3H), 3.54 (s, 3H), 3.28–3.05 (m, 3H), 2.88–2.75 (m, 1H) ppm.

D. Dimethyl 2-[2-(2-aminophenyl)ethyl]-4-(2,6-dichlorophenyl)-6-(2-methoxy-2-oxoethyl)-1,4-dihydro-3,5-pyridinedicarboxylate A mixture of dimethyl 4-(2,6-dichlorophenyl)-2-(2-methoxy-2-oxoethyl)-6-[2-(2-nitrophenyl)ethyl]-1,4-dihydro-3,5-pyridinedicarboxylate (3.0 g) and palladium hydroxide, 20 wt % on carbon (300 mg) in MeOH (50 ml) was stirred under hydrogen atmosphere by balloon for 4 hours. Catalyst was removed by filtration and filter cake was washed with CH$_2$Cl$_2$. The combined organic solvent was evaporated to afford a dark green solid (2.61 g192%).

$^1$H NMR (CDCl$_3$) δ: 7.35 (s, 1H), 7.26 (m, 2H), 7.03 (m, 3H), 6.68 (m, 2H), 5.99 (s, 1H), 4.31 (br s, 2H), 3.88 (d, J=16.7 Hz, 1H), 3.74. (s, 3H), 3.65 (d, J=16.7 Hz, 1H), 3.55 (s, 3H), 3.54 (s, 3H), 3.05 (m, 1H), 2.82 (m, 2H), 2.51 (m, 1H) ppm E. Dimethyl 4-(2,6-dichlorophenyl)-2-(2-methoxy-2-oxoethyl)-6-(2-{2-[(methylsulfonyl)amino]phenyl}ethyl)-1,4-dihydro-3,5-pyridinedicarboxylate To a stirred solution of dimethyl 2-[2-(2-aminophenyl)ethyl]-4-(2,6-dichlorophenyl)-6-(2-methoxy-2-oxoethyl)-1,4-dihydro-3,5-pyridinedicarboxylate (500 mg/0.94 mmol) and methanesulfonyl chloride (107 mg/0.94 mmol) in anhydrous CH$_2$Cl$_2$(15 ml) was added triethylamine (94.7 mg/0.94 mmol) at 0° C. under nitrogen atmosphere. The resulting solution was stirred at room temperature for 1 day. The reaction was quenched with water and the separated organic layer was washed with water and brine, dried over MgSO$_4$, filtered and concentrated to afford a crude mixture. This crude was purified by column chromatography on silica gel (Hexane:EtOAc=3:2) to afford a yellow solid (262 mg/46%).

$^1$H NMR (CDCl$_3$) δ: 8.26 (s, 1H), 7.55 (m, 1H), 7.33–6.99 (m, 6H), 5.98 (s, 1H), 3.99 (d, J=17.1 Hz, 1H), 3.74 (s, 3H), 3.67 (d, J=17.1 Hz, 1H), 3.62 (s, 3H), 3.53 (s, 3H), 3.03–2.78 (m, 3H), 2.99 (s, 3H), 2.52 (m, 1H) ppm.

F. [4-(2,6-dichlorophenyl)-3,5-bis(methoxycarbonyl)-6-(2-{2-[(methylsulfonyl)amino]phenyl}ethyl)-1,4-dihydro-2-pyridinyl]acetic acid This compound was prepared by a procedure similar to that described in example 1-E as a yellow solid. This product was used for next reaction without purification.

G Dimethyl 4-(2,6-dichlorophenyl)-2-{2-[4-(8-methyl-8-azabicyclo[3.2.1]oct-3-yl)-1-piperazinyl]-2-oxoethyl}-6-(2-{2-[(methylsulfonyl)amino]phenyl}ethyl)-1,4-dihydro-3,5-pyridinedicarboxylate This compound was prepared by Ea procedure similar to that described in example 1-F as a yellow amorphous.

$^1$H NMR (CDCl$_3$) δ: 8.41 (s, 1H), 7.58 (m, 1H), 7.27–7.00 (m, 6H), 5.95(s, 1H), 4.06 (d, J=15.4 Hz, 1H), 3.93 (d, J=15.4 Hz, H), 3.75–3.50 (m, 4H), 3.62 (s, 3H), 3.54 (s, 3H), 3.20 (m, 2H), 2.97–2.84 (m, 4H), 2.95 (s, 3H), 2.63–2.50 (m, 6H), 2.28 (s, 3H), 2.01 (m, 1H),1.72–1.51 (m, 6H) ppm.

HCl salt was prepared by a procedure similar to that described in example 1-H as a yellow solid.

mp 143° C.

IR (KBr)ν$_{max}$: 3226, 2947, 1697, 16:24, 1506, 1434, 1292, 1153, 1114, 767 cm$^{-1}$ MS (m/z): 788 (M+H)+

Example 11

Dimethyl 4-(2,6-dichlorophenyl)-2-{2-[4-(8-methyl-8-azabicyclo[3.2.1]oct-3-yl)-1-piperazinyl]-2-oxoethyl}-6-(2-{2-[2-(2-oxo-1-pyrrolidinyl)ethoxy]phenyl}ethyl)-1,4-dihydro-3,5-pyridinedicarboxylate A. Dimethyl 4-(2,6-dichlorophenyl)-2-[2-(2-hydroxyphenyl)ethyl]-6-(2-methoxy-2-oxoethyl)-1,4-dihydro-3,5-pyridinedicarboxylate To a solution of dimethyl 2-[2-(2-{[tert-butyl(dimethyl)silyl]oxy}phenyl)ethyl]-4-(2,6-dichlorophenyl)-6-(2-methoxy-2-oxoethyl)-1,4-dihydro-3,5-pyridinedicarboxylate (example 5, 3.90 g/6.01 mmol) in THF (39 ml) was added a solution of tetrabutylammonium fluoride (6.0 ml/6.0 mmol) at 0° C. and the resulting solution was stirred for 30 min at room temperature. The mixture was poured into water. The whole was extracted with dichloromethane (100 ml×2). The combined organic layer was washed with brine (30 ml), dried over magnesium sulfate, filtered and concentrated. The residue was purified by column chromatography (SiO$_2$, 200–350 mesh/hexane:ethyl acetate=4:1–2:1) to afford a yellow oil (3.20 g/99%).

$^1$H NMR (CDCl$_3$) δ: 7.81□ (br.s, 1H), 7.33–6.78 (m, 7H), 5.97 (s, 1H), 3.96 (d, J=17 Hz, 1H), 3.74 (s, 3H), 3.63 (d, J=17 Hz, 1H), 3.59 (s, 3H), 3.53 (s, 3H), 3.08–2.77 (m, 3H), 2.47–2.36 (m, 1H) ppm.

B. Dimethyl 4-(2,6-dichlorophenyl)-2-(2-methoxy-2-oxoethyl)-6-(2-{2-[2-(2-oxo-1-pyrrolidinyl)ethoxy]phenyl}ethyl)-1,4-dihydro-3,5-pyridinedicarboxylate To a solution of dimethyl 4-(2,6-dichlorophenyl)-2-[2-(2-hydroxyphenyl)ethyl]-6-(2-methoxy-2-oxoethyl)-1,4-dihydro-3,5-pyridinedicarboxylate (1.07 g/2.0 mmol) in benzene (35 ml) was added 1,1'-(azodicarbonyl)dipiperidine (1.01 g/4.0 mmol), tributylphosphine (809 mg/4.0 mmol), 1-(2-hydroxyethyl)-2-pyrrolidinone (2.58 g/20 mmol), and the resulting solution was stirred for 16 hours at room temperature. The solvent was evaporated. The residue was purified by column chromatography (SiO$_2$, 200–350 mesh/hexane:ethyl acetate=1:1) to afford a yellow oil (450 mg/35%).

$^1$H NMR (CDCl$_3$) δ: 8.87 (s, 1H), 7.33–6.73 (m, 6H), 6.04 (s, 1H), 4.16–3.75 (m, 7H), 3.71 (s, 3H), 3.56 (s, 3H), 3.51 (s, 3H), 3.49–3.46 (m, 1H), 2.98–2.70 (m, 3H), 2.55–2.36 (m, 3H), 2.12–2.03 (m, 2H) ppm.

C. [4-(2,6-Dichlorophenyl)-3,5-bis(methoxycarbonyl)-6-(2-{2-[2-(2-oxo-1-pyrrolidinyl)ethoxy]phenyl}ethyl)-1,4-dihydro-2-pyridinyl]acetic acid This compound was prepared by a procedure similar to that described in example 1-E as a yellow oil, and used for next reaction without further purification.

D. Dimethyl 4-(2,6-dichlorophenyl)-2-{2-[4-(8-methyl-8-azabicyclo[3.2.1]oct-3-yl)-1-piperazinyl]-2-oxoethyl}-6-(2-(2-[2-(2-oxo-1-pyrrolidinyl)ethoxy]phenyl}ethyl)-1,4-dihydro-3,5-pyridinedicarboxylate This compound was prepared by a procedure similar to that described in example 1-F as a yellow oil.

Free Base $^1$H NMR (CDCl$_3$) δ: 8.43 (s, 1H), 7.28–6.75 (m, 6H), 6.02 (s, 1H), 4.15–3.52 (m, 11H), 3.51 (s, 3H), 3.49 (s, 3H), 3.20 (s, 2H), 3.00–2.35 (m, 10H), 2.28 (s, 3H), 2.16–1.25 (m, 12H) ppm.

HCl salt was prepared by a procedure similar to that described in example 1-H as a yellow solid.

mp 148–150° C.(dec.)

Example 12

Dimethyl 2-[2-(2-{[4-(tert-butoxy carbonyl)-1-piperazinyl]methylephenyl)ethyl]-4-(2,6-dichlorophenyl)-6-{2-[4-(8-methyl-8-azabicyclo[3.2.1]oct-3-yl)-1-piperazinyl]-2-oxoethyl}-1,4-dihydro-3,5-pyridinedicarboxylate A. Dimethyl 2-[2-(2-{[4-(tert-butoxycarbonyl)-1-piperazinyl]methyl}phenyl)ethyl]-4-(2,6-dichlorophenyl)-6-(2-methoxy-2-oxoethyl)-1,4-dihydro-3,5-pyridinedicarboxylate This compound was prepared by a procedure similar to that described in example 7-F $^1$H NMR (CDCl$_3$) δ 7.32–6.97 (m, 8H), 6.00 (s, 1H), 3.76–3.48 (m, 13H), 3.43–3.37 (m, 4H), 3.07–2.85 (m, 4H), 2.48–2.34 (m, 4H), 1.45 (s, 9H) ppm.

B. [6-[2-(2-{[4-(tert-butoxycarbonyl)-1-piperazinyl]methyl}phenyl)ethyl]-4-(2,6-dichlorophenyl)-3,5-bis(methoxycarbonyl)-1,4-dihydro-2-pyridinyl]acetic Acid This compound was prepared by a procedure similar to that described in example 1-E.

$^1$H NMR (CDCl$_3$) 8.39 (br. s, 1H), 7.40–6.95 (m, 7H), 5.98 (s, 1H), 4.05–3.45 (m, 14H), 3.10–2.65 (m, 8H), 1.45 (s, 9H) ppm.

C. Dimethyl 2-[2-(2-{[4-(tert-butoxycarbonyl)-1-piperazinyl]methyl}phenyl)ethyl]-4-(2,6-dichlorophenyl)-6-{2-[4-(8-methyl-8-azabicyclo[3.2.1]oct-3-yl)-1-piperazinyl]-2-oxoethyl}-1,4-dihydro-3,5-pyridinedicarboxylate This compound was prepared by a procedure similar to that described in example 1-F.

$^1$H NMR (CDCl$_3$) 8.21 (br. s, 1H), 7.40–6.95 (m, 7H), 6.00 (s, 1H), 4.26 (d, J=15.0 Hz, 1H), 3.75–3.50 (m, 13H), 3.47–3.34 (m, 4H), 3.25–3.15 (m, 2H), 3.07–2.80 (m, 4H), 2.65–2.35 (m, 9H), 2.27 (s, 3H), 2.05–1.95 (m, 2H), 1.75–1.40 (m, 6H), 1.45 (s, 9H) ppm.

HCl salt was prepared by a procedure similar to that described in example 1-H as a yellow solid.

mp: 95–98° C. (dec.)

MS (m/z): 893 (M+H)$^+$.

IR (KBr)ν$_{max}$: 3290, 3229, 2945, 2810, 1697, 1631, 1499, 1433, 1366, 1350, 1290, 1242, 1173, 1115, 1047, 1003, 955, 7683 cm$^{-1}$.

Example 13

Dimethyl 4-(2,6-dichlorophenyl)-2-{2-[4-(8-methyl-8-azabicyclo[3.2.1]oct-3-yl)-1-piperazinyl]-2-oxoethyl}-6-(2-{2-[(2,2,2-tirifluoroethyl)amino]phenyl}ethyl)-1,4-dihydro-3,5-pyridinedicarboxylate A. Dimethyl 4-(2,6-dichlorophenyl)-2-(2-methoxy-2-oxoethyl)-6-(2-{2-[(2,2,2-trifluoroethyl)amino]phenyl}ethyl)-1,4-dihydro-3,5-pyridinedicarboxylate To a stirred solution of dimethyl 4-(2,6-dichlorophenyl)-2-(2-methoxy-2-oxoethyl)-6-[2-(2-nitrophenyl)ethyl]-1,4-dihydro-3,5-pyridinedicarboxylate (example 10, 1.56 g/2.92 mmol) and N,N-diisopropylethylamine (3.78 g/29.2 mmol) in toluene (50 ml) was added trifluoromethanesulfonic acid 2,2,2-trifluoroethyl ester (6.78 g/29.2 mmol) at room temperature. The reaction mixture was refluxed at 130° C. for 1 day. The reaction was quenched with water and the separated organic layer was washed with sat.NaHCO$_3$ and brine, dried over MgSO$_4$, filtered and concentrated to afford a crude mixture. This crude was purified by column chromatography on silica gel (Hexane:EtcAc=2:1) to afford a pale yellow oil (1.34 g/75%).

$^1$H NMR (CDCl$_3$):7.27–6.99 (m, 5H), 6.71 (m, 2H), 5.99 (s, 1H), 5.90 (m, 1H), 3.99 (d, J=17.1 Hz, 1H), 3.81 (m, 2H), 3.77 (s, 3H), 3.70 (d, J=17.1 Hz, 1H), 3.56 (s, 3H), 3.54 (s, 3H), 3.01 (m, 1H), 2.83 (m, 2H), 2.30 (m, 1H) ppm.

B. [4-(2,6-dichlorophenyl)-3,15-bis(methoxycarbonyl)-6-(2-{2-[(2,2,2-trifluoroethyl)amino]phenyl}ethyl)-1,4-dihydro-2-pyridinyl]acetic acid This compound was prepared by a procedure similar to that described in example 1-E as a yellow amorphous. This product was used for next reaction without purification.

C. Dimethyl 4-(2,6-dichlorophenyl)-2-{2-[4-(8-methyl-8-azabicyclo[3.2.]oct-3-yl)-1-piperazinyl]-2-oxoethyl}-6-(2-{2-[(2,2,2-trifluoroethyl)amino]phenyl}ethyl)-1,4-dihydro-3,5-pyridinedicarboxylate This compound was prepared by a procedure similar to that described in example 1-F as a yellow amorphous.

Free Base $^1$H NMR (CDCl$_3$) δ: 8.35 (s, 1H), 7.26–6.98 (m, 5H), 6.70 (m, 2H), 5.97 (s, 1H), 5.88 (m, 1H), 4.08 (d, J=15.4 Hz, 1H), 3.94 (d, J=15.4 Hz, 1H), 3.83 (m, 2H) 3.64 (m, 3H), 3.56 (s, 3H), 3.54 (s, 3H), 3.20 (m, 2H), 2.99–2.76 (m, 3H), 2.63–2.43 (m, 7H), 2.27 (s, 3H), 2.00 (m, 2H), 1.71–1.51 (m, 6H) ppm.

HCl salt was prepared by a procedure similar to that described in example 1-H as a yellow solid.

mp 196° C.

IR (KBr)ν$_{max}$: 3390, 2947, 1693, 16:31, 1502, 1433, 1294, 1110, 767 cm$^{-1}$ MS (m/z): 792 (M+H)$^+$ Example 14

Dimethyl 4-(2,6-dichlorophenyl)-2-{2-[2-({[4-(methylamino)4-oxobutanoyl]amino}methyl)phenyl]ethyl}-6-{2-[4-(8-methyl-8-azabicyclo[3.2.1]oct-3-yl)-1-piperazinyl]-2-oxoethyl}-1,4-dihydro-3,5-pyridinedicarboxylate A. [4-(2,6-dichlorophenyl 2-[2-(hydroxymethyl)phenyl]ethyl}-3,5-bis(methoxy carbonyl)-1,4-dihydro-2-pyridinyl]acetic Acid This compound was obtained according to a similar manner to that of example 1-E as a yellow amorphous.

$^1$HNMR (CDCl$_3$) δ: 8.31 (s, 1H), 7.34–7.18 (m, 6H), 7.03 (t, 1H, J=7.6 Hz), 5.95 (s, 1H), 4.84 (d, 1H, J=11.7 Hz), 4.78 (d, 1H, J=11.4 Hz), 3.62–3.51 (m, 7H), 3.10–2.80 (m, 4H) ppm.

B. Dimethyl 4-(2,6-dichlorophenyl)-2-{2-[2-(hydroxymethyl)phenyl]ethyl}-6-{2-[4-(8-methyl-8-azabicyclo[3.2.1]oct-3-yl)-1-piperazinyl]-2-oxoethyl}-1,4-dihydro-3,5-pyridinedicarboxylate This compound was obtained according to a similar manner to that of example 1-F as a yellow amorphous.

$^1$HNMR (CDCl$_3$) δ: 7.88 (s, 1H), 7.34–7.15 (m, 6H), 7.01 (t, 1H, J=8.2 Hz), 5.98 (s, 1H), 4.81 (d, 1H, J=12.2 Hz), 4.76 (d, 1H, J=12.0 Hz), 4.30 (d, 1H, J=14.8 Hz), 3.68–3.50 (m, 10H), 3.46 (d, 1H, J=14.5 Hz), 3.25–3.10 (br, 2H), 3.05–2.92 (m, 4H), 2.62–2.36 (m, 5H), 2.27 (s, 3H), 2.05–1.95 (m, 2H), 1.78–1.46 (m, 6H) ppm.

C. Dimethyl 4-(2,6-dichlorophenyl)-2-(2-{2-[(2,5-dioxo-1-pyrrolidinyl)methyl]phenylethyl}-6-12-[4-(8-methyl-8-azabicyclo[3.2.1]oct-3-yl)-1-piperazinyl]-2-oxoethyl)-1,4-dihydro-3,5-pyridinedicarboxylate To a solution of dimethyl 4-(2,6-dichlorophenyl)-2-{2-[2-(hydroxymethyl) phenyl] ethyl}-6-{2-[4-(8-methyl-8-azabicyclo[3.2.1]]oct-3-yl)-1-piperazinyl]-2-oxoethyl}-1,4-dihydro-3,5-pyridinedicarboxylate (2.8 g/3.9 mmol) and 1,1'-azobis(N,N-dimethylformamide) (1.35 g/7.8 mmol) in THF (30 ml) was added tri-n-butylphosphine (1.92 ml/7.6 mmol) and stirred for 10 min at room temperature. To the mixture was added succinimide (765 mg/7.7 mmol) and stirred for 9 h at room temperature. The mixture was evaporated and the residue was purified by column chromatography on NH$_2$ gel to afford dimethyl 4-(2,6-dichlorophenyl)-2-(2-(2-[(2,5-dioxo-1-pyrrolidinyl)methyl]phenylethyl}-6-{2'-[4-(8-methyl-8-azabicyclo[3.2.1]oct-3-yl)-1-piperazinyl]-2-oxoethyl}-1,4-dihydro-3,5-pyridinedicarboxylate as a pale yellow solid (2 g/64%).

$^1$HNMR (CDCl$_3$) δ: 8.04 (s, 1H), 7.36–7.10 (m, 6H), 7.00 (t, 1H, J=7.6 Hz), 6.01 (s, 1H), 4.81 (s, 2H), 4.02 (d, 1H, J=15.5 Hz), 3.90 (d, 1H, J=15.0), 3.66–3.50 (m, 10H), 3.26–3.15 (br, 2H), 3.13–3.01 (m, 2H), 3.01–2.75 (m, 2H), 2.75 (s, 4H), 2.65–2.43 (m, 5H), 2.28 (s, 3H), 2.06–1.95 (m, 2H), 1.76–1.48 (m, 6H) ppm.

D. Dimethyl 4-(2,6-dichlorophenyl)-2-{2-[2-({[4-(methylamino)-4-oxobutanoyl]amino}methyl)phenyl]ethyl}-6-[2-[4-(8-methyl-8-azabicyclo[3.2.1]oct-3-yl)-1-piperazinyl]-2-oxoethyl}-1,4-dihydro-3,5-pyridinedicarboxylate To a solution of dimethyl 4-(2,6-dichlorophenyl)-2-(2-{2-[(2,5-dioxo-1-pyrrolidinyl) methyl]phenylethyl}-6-{2-[4-(8-methyl-8-azabicyclo[3.2.1]oct-3-yl)-1-piperazinyl]-2-oxoethyl}-1,4-dihydro-3,5-pyridinedicarboxylate (2.0 g/2.48 mmol) in MeOH (125 ml) was added methylamine (40% in MeOH/125 ml) and stirred for 1 h at room temperature. The mixture was then evaporated to dryness and the residue was purified by column chromatography on NH$_2$ gel (CH$_2$Cl$_2$/MeOH=20/1) to afford dimethyl 4-(2,6-dichlorophenyl)-2-{2-[2-({[4-(methylamino)-4-oxobutanoyl]aminomethyl)phenyl]ethyl}-6-{2-[4-(8-methyl-8-azabicyclo[3.2.1]oct-3-yl)-1-piperazinyl]-2-oxoethyl}-1,4-dihydro-3,5-pyridine dicarboxylate as a pale yellow solid (1.26 g/61%).

$^1$HNMR (CDCl$_3$) δ: 8.25 (s, 1H), 7.46–7.10 (m, 8H), 7.00 (t, 1H, J=8.2 Hz), 6.02(s, 1H), 5.06 (dd, 1H, J=8.8, 14.1 Hz), 4.30 (d, 1H, J=15.4 Hz), 4.00 (dd, 1H, J=2.8, 14.1 Hz), 3.68–3.56 (m, 4H), 3.56 (s, 3H), 3.50 (s, 3H), 3.50 (d, 1H, J=15.4 Hz) 3.25–3.18 (br, 2H), 3.18–2.78 (m, 3H), 2.66 (d, 3H, J=4.8 Hz), 2.66–2.10 (m, 13H), 2.06–1.50 (m, 8H) ppm.

Citrate salt was prepared by a procedure similar to that described in example 1-H as a yellow solid.

mp 158–160° C.(dec.)

IR (KBr)ν$_{max}$: 3300, 2947, 1693, 1545, 1512, 1435, 1292, 1188, 1103, 768 cm$^{-1}$.

$^1$H-NMR (DMSO-d6) δ: 8.99 (s, 1H), 8.33–8.28 (m, 1H), 7.75–7.65 (m, 1H), 7.35–7.06 (m, 7H), 5.84 (s, 1H), 4.50–4.23 (m, 2H), 4.15 (d, 1H, J=15.5 Hz), 3.65–2.20 (m, 32H), 2.20–2.00 (m, 2H), 1.95–1.65 (m, 6H)

MS (m/z): 835 (M–H)$^+$

Example 15 dimethyl 4-(2,6-dichlorophenyl)-2-[2-(2-{[2-(diethylamino)ethoxy]methyl}phenyl)ethyl]-6-{2-[4-(8-methyl-8-azabicyclo[3.2.1]oct-3-yl)-1-piperazinyl]-2-oxoethyl}-1,4-dihydro-3,5-pyridinedicarboxylate;

4-(2,6-Dichloro-phenyl)-2-{2-[2-(2-diethylamino-ethoxymethyl)-phenyl]-ethyl}-6-{2-[4-(8-methyl-8-azabicyclo[3.2.1]oct-3.yl)-piperazin-1-yl]-2-oxo-ethyl}-1,4-dihydro-pyridine-3,5-dicarboxylic Acid Dimethyl Ester A. N-[2-[(2-bromobenzyl)oxy]ethyl]-N,N-diethylamine N,N-Diethylethanolamine (51.2 mL.) was added dropwise to a mixture of potassium t-butoxide (43.3 g) in THF (300 mL, in 2000 mL 4-necked flask) at 0° C. (ice-cold bath)

under nitrogen atmosphere (exothermic reaction) via 100 mL dropping funnel and the resulting mixture was stirred at 0° C. for 30 min. A solution of 2-bromobenzyl bromide (87.7 g) in THF (140 mL) was added dropwise to the mixture via 200 mL dropping funnel at 0° C. (exothermic reaction). The reaction mixture was stirred at room temperature for 5 hours.

Aliquot was taken out, filtered and the filtrate was concentrated. The consumption of the starting material was confirmed by $^1$H-NMR analysis of this sample.

Water (350 mL, 4 vol) and 1:1 mixture of AcOEt and hexane (350 mL, 4 vol) were added to the reaction mixture, and then layers were separated. The organic layer was washed with water (350 mL, 4 vol) and dried over $Na_2SO_4$ (ca. 100 g). After filtration through Celite pad (ca. 50 g), the filtrate was concentrated and dried up by vacuum pump overnight to give 89.9 g (90% yield) of N-[2-[(2-bromobenzyl)oxy]ethyl]-N,N-diethylamine as a yellow oil.

$^1$H-NMR (270 MHz, CDCl$_3$) δ: 7.6–7.5 (m, 2H), 7.4–7.3 (m, 1H), 7.2–7.1 (m, 1H), 4.6 (s, 2H), 3.7 (t, J=2.3 Hz, 2H), 2.7 (t, J=2.3 Hz, 2H), 2.6 (q, J=2.6 Hz, 4H), 1.0 (t, J=2.6 Hz, 6H) ppm.

B. Ethyl (2E)-3-[2-[[2-(diethylamino)ethoxy]methyl]phenyl]-2-propenoate

A mixture of N-[2-[(2-bromobenzyl)oxy]ethyl]-N,N-diethylamine (6.36 g), ethyl acrylate (4.82 mL), potassium carbonate (7.68 g), tetra-n-butylammonium bromide (7.16 g), tri-o-tolylphosphine (0.271 g) and palladium acetate (0.0998 g) in toluene (20 mL) was stirred at room temperature. The resulting mixture was degassed under reduced pressure and replaced with nitrogen (×3). The mixture was stirred at 100° C. under nitrogen atmosphere for 9 hours.

Aliquot (one drop) was taken out, diluted with AcOEt and filtered. The consumption of the starting material was confirmed by HPLC analysis of this filtrate.

The reaction mixture was filtered through Celite pad. The filtrate was cooled to ca. 10° C. and 2 N aqueous HCl (25 mL) was added, then the resulting mixture was stirred. After layers were separated, the aqueous layer was cooled to ca. 10° C. and basified with 2 N aqueous NaOH (50 mL). The mixture was extracted with 1:1 mixture of AcOEt and hexane (50 mL) was added to the mixture and the layers were separated. Organic layer was dried over $Na_2SO_4$, filtered and the filtrate was concentrated to give 6.61 g (97% yield) of ethyl (2E)-3-[2-[[2-(diethylamino)ethoxy]methyl]phenyl]-2-propenoate as a colorless oil.

$^1$H-NMR (300 MHz, CDCl$_3$) δ: 8.0 (d, J=5.3 Hz, 1H), 7.6 (m, 1H), 7.4–7.3 (m, 3H), 6.4 (d, J=5.3 Hz, 1H), 4.6 (s, 2H), 4.3 (q, J=2.4 Hz, 2H), 3.6 (t, J=2.1 Hz, 2H), 2.7 (t, J=2.1 Hz, 2H), 2.6 (q, J=2.4 Hz, 4H), 1.3 (t, J=2.4 Hz, 3H), 1.0 (t, J=2.4 Hz, 6H) ppm.

C. 3-[2-[[2-(diethylamino)ethoxy]methyl]phenyl]-2-propanoic Acid

In 100 mL flask, a mixture of 5.00 g of Ethyl (2E)-3-[2-[[2-(diethylamino)ethoxy]methyl]phenyl]-2-propenoate and 250 mg of 10% Pd/C (wet; 50% water) in 15 mL of EtOH (100 mL of flask) was stirred vigorously for 4 h at r.t. under $H_2$ atmosphere (~1 atm). The reaction mixture was filtered through Celite (2.0 g) pad and the resulting Pd/C on the celite pad was washed with 10 mL of EtOH. The resulting filtrate was added 3.6 mL of 5N aqueous NaOH and the reaction solution was stirred at r.t. for 3 h. After the reaction vessel was immersed in water bath, 1N HCl in EtOH was added dropwise to the reaction solution (CAUTION; exothermic). The formation of white precipitates (NaCl) was noticed during this procedure. The solvents were removed by simple distillation procedure at ~1 atm (Oil bath temperature; 105° C., vapor temperature; 77° C.) during the period of 1.5 h. The residue was then diluted with 26 mL of acetonitrile and then the solvent was removed by distillation during the period of 40 min (Oil bath temperature; 105° C., vapor temperature; 74.5~77.5° C.) for removing $H_2O$ and ethanol azeotropically. To the residue was added 26 mL of acetonitrile again, and this procedure was repeated (vapor temperature at the second disitillation; 79.5° C.~80.5° C). The residue was then diluted with 15 mL of acetonitrile and 2.5 g of $Na_2SO_4$ was added. The resulting mixture was stirred gently at room temperature overnight, then filtered through celite pad (2.0 g). The celite pad was washed with 10 mL of acetonitrile. The filtrate (pale yellow solution) was concentrated to give 4.96 g of 3-[2-[[2-(diethylamino)ethoxy]methyl]phenyl]-2-propanoic acid as a pale yellow oil.

$^1$H NMR (300 MHz, CDCl$_3$) δ: 7.3–7.1 (m, 4H), 6.8 (br s), 4.5 (s, 2H), 3.7 (t, J=5.1 Hz, 2H), 3.0–2.9 (m, 4H), 2.5 (t, J=7.3 Hz, 4H), 1.1 (t, J=7.1 Hz, 6H) ppm.

(Ethyl 3-[2-[[2-(diethylamino)ethoxy]methyl]phenyl]-2-propanoate)

$^1$H NMR (300 MHz, CDCl$_3$) δ: 7.3–7.1 (m, 4H), 4.5 (s, 2H), 4.1 (q, J=7.1 Hz, 2H), 3.5 (t, J 6.4 Hz, 2H), 3.0 (t, J=7.4 Hz, 2H), 2.7–2.5 (m, 4H), 1.3–1.2 (t, J=7.2 Hz, 3H), 1.0 (t, J=7.3 Hz, 6H) ppm.

Colorless Oil

D. Methyl-5-[2-[[2-(diethylamino)ethoxy]methyl]phenyl]-3-oxopentanoate

To a solution of 4.87 g of 3-[2-([2-(diethylamino)ethoxy]methyl]phenyl]-2-propanoic acid containing 61 mol % (8.9 wt %) of acetonitrile in 25 mL of anhydrous DMF (200 mL of flask) was added 2.65 g of 1,1'-carbonyldiimidazole portionwise at r.t. (CAUTION; Gas (CO$_2$) evolution!!). The reaction solution was maintained at. r.t. for 30 min and at 55° C. for 1 h under nitrogen, then cooled to room temperature. To the solution were added 1.71 g of MgCl$_2$ portionwise carefully (CAUTION; Exothermic!!) and 2.81 g of potassium methyl malonate at room temperature. The reaction mixture was stirred at 55° C. for 14 h under nitrogen atmosphere and cooled to room temperature. To the mixture was added aqueous solution of tri-sodium citrate (this solution was prepared by dissolving 13.2 g of tri-sodium citrate into 52.8 mL of $H_2O$) and 30 mL of 1:1 mixture of EtOAc—hexane. The resulting mixture was stirred vigorously at r.t. for 2 h, then layers were separated. Aqueous layer was extracted with 1:1 mixture of EtOAc—hexane (20 mL×2). The combined organic layer was washed with $H_2O$ (15 mL×2), then dried over $Na_2SO_4$. After the filtration through paper filter, the filtrate was concentrated under reduced pressure to give 5.02 g of methyl-5-[2-[[2-(diethylamino)ethoxy]methyl]phenyl]-3-oxopentanoate (91% yield) as a brown oil. The purity of the product was determined to be 97% by HPLC analysis.

$^1$H-NMR (300 MHz, CDCl$_3$) δ: 7.3–7.1 (m, 4H), 4.5 (s, 2H), 3.7 (s, 3H), 3.6 (t, J=6.4 Hz, 2H), 3.5 (s, 2H), 3.0–2.8 (m, 4H), 2.7 (t, J=6.4 Hz, 2H), 2.6 (q, J=7.1 Hz, 2H), 1.0 (t, J=7.1 Hz, 6H) ppm.

E. Methyl3-(2,6-dichlorophenyl)-2-[3-[2-[[2-(diethylamino)ethoxy]methyl]phenyl]propanoyl]-2-propenoate This compound was obtained according to a similar manner to that of example 1-C as a yellow oil.

$^1$H-NMR (300 MHz, CDCl$_3$) δ: 7.6 (s, 1H), 7.3–7.1 (m, 7H), 4.6 (s, 1H), 4.5 (s, 1H), 3.9 (s, 1.5H), 3.6 (s, 1.5H), 3.6–3.5 (m, 2H), 3.3–3.0 (m, 4H), 3.0–2.8 (m, 4H), 2.7–2.6 (m, 2H), 2.5 (q, 4H), 1.0 (m, 6H) ppm.

F. Dimethyl4-(2,6-dichlorophenyl)-2-[2-[2-[[2-(diethylamino)ethoxy]methyl]phenyl]ethyl]-6-(2-methoxy-2-oxoethyl)-1,4-dihydro-3,5-pyridinedicarboxylate This compound was obtained according to a similar manner to that of example 1-D as a yellow amorphous.

$^1$H-NMR (300 MHz, CDCl$_3$) δ: 7.6 (s, 1H), 7.3–7.2 (m, 6H), 7.0 (t, J=7.5 Hz, 1H), 6.0 (s, 1H), 4.6 (s, 2H), 3.7 (s, 3H), 3.6–3.5 (m, 10H), 3.2–2.9 (m, 4H), 2.7–2.6 (m, 4H), 2.5 (q, J=7.1 Hz, 4H), 1.0 (t, J=7.1 Hz, 6H) ppm.

G. Dimethyl4-(2,6-dichlorophenyl)-2-[2-(2-{[2-(diethylamino)ethoxy]methylphenyl)ethyl]-6-{2-[4-(8-methyl-8-azabicyclo[3.2.1]oct-3-yl)-1-piperazinyl]-2-oxoethyl}-1,4-dihydro-3,5-pyridinedicarboxylate This compound was obtained according to a similar manner to that of example 1-E and F as a yellow amorphous.

$^1$H NMR (CDCl$_3$, 300 MHz) δ: 8.15 (brs, 1H), 7.37–7.14 (m, 6H), 7.00 (t, J=8.0 Hz, 1H), 5.99 (s, 1H), 4.64 (s, 2H), 4.07 (d, J=15.0 Hz, 1H), 3.77 (d, J=15.0 Hz, 1H), 3.69–3.53 (m, 6H), 3.55 (s, 3H), 3.54 (s, 3H), 3.25–3.16 (m, 2H), 3.02–2.80 (m, 5H), 2.69 (t, J=6.4 Hz, 2H), 2.55 (q, J=7.1 Hz, 4H), 2.64–2.44 (m, 4H), 2.28 (s, 3H), 2.08–1.48 (m, 8 H), 1.00 (t, J=7.1 Hz, 6H). ES(+): 824.51; ES(−): 822.34

H. Optical isomer of dimethyl 4-(2,6-dichlorophenyl)-2-[2-(2-{[2-(diethylamino)ethoxy]methylphenyl)ethyl]-6-{2-[4-(8-methyl-8-azabicyclo[3.2.1]oct-3-yl)-1-piperazinyl]-2-oxoethyl}-1,4-dihydro-3,5-pyridinedicarboxylate The title enantiomer was obtained by seperation on a chiral mobile phase (Hexane/ethanol/diethylamine=90/10/0.1) of the racemate dimethyl 4-(2,6-dichlorophenyl)-2-[2-(2-f[2-(diethylamino)ethoxy]methyl}phenyl)ethyl]-6-{2-[4-(8-methyl-8-azabicyclo[3.2.1]oct-3-yl)-1-piperazinyl]-2-oxoethyl}-1,4-dihydro-3,5-pyridinedicarboxylate. The racemate was resolved by HPLC using a chiral pak (DAICEL CHIRALPAK AD-H, 4.6×250 mm).

$[α]_D^{21.5}$=−44.2 (c=0.615, methanol)

Example 16

Dimethyl 4-(2,6-dichlorophenyl)-2-{2-[4-(8-methyl-8-azabicyclo[3.2.1]oct-3-yl)-1-piperazinyl]-2-oxoethyl}-6-[2-(2-{[(trifluoromethyl)sulfonyl]amino}phenyl)ethyl]-1,4-dihydro-3,5-pyridinedicarboxylate Dimethyl4-(2,6-dichlorophenyl)-2-(2-methoxy-2-oxoethyl)-6-[2-(2-{[(trifluoromethyl)sulfonyl]aminolphenyl)ethyl]-1,4-dihydro-3,5-pyridinedicarboxylate To a cooled solution of dimethyl 2-[2-(2-aminophenyl)ethyl]-4-(2,6-dichlorophenyl)-6-(2-methoxy-2-oxoethyl)-1,4-dihydro-3,5-pyridinedicarboxylate (224.9 mg/0.422 mmol) and triethylamine (75 μl/0.540 mmol) in dichloromethane (8 ml) was added dropwise trifluoromethanesulfonic anhydride (72 μl/0.439 mmol) and stirred under N$_2$ for 45 minutes. The mixture was added ice and allowed to warm to room temperature. The whole was extracted with dichloromethane, washed with brine, dried over sodium sulfate, and concentrated in vacuo. The residue was purified by column chromatography on silica gel (Hexane:EtOAc= 3:2–1:1) to afford dimethyl 4-(2,6-dichlorophenyl)-2-(2-methoxy-2-oxoethyl)-6-[2-(2-{[(trifluoromethyl)sulfonyl] amino}phenyl)ethyl]-1,4-dihydro-3,5-pyridinedicarboxylate as a pale yellow solid (235.9 mg/84%).

$^1$H NMR (CDCl$_3$) δ: 7.54 (d, 1H, J=7.8 Hz), 7.42–7.38 (br, 1H), 7.30–7.16 (m, 6H) 7.03 (dd, 1H, J=7.6, 8.4 Hz), 5.95 (s, 1H), 4.04 (d, 1H, J=17.3 Hz), 3.78 (d, 3H), 3.68 (d, 1H, J=17.0 Hz), 3.61 (s, 3H), 3.54 (s, 3H), 2.98–2.80 (m, 3H), 2.62–2.44 (m, 1H) ppm.

B. {4-(2,6-dichlorophenyl)-3,5-bis(methoxycarbonyl)-6-[2-(2-{[(trifluoromethyl) sulfonyl]amino}phenyl)ethyl]-1,4-dihydro-2-pyridinyl}acetic Acid This compound was obtained according to a similar manner to that of example 1-E as a yellow amorphous.

$^1$H NMR (CDCl$_3$) δ: 9.57–9.43 (br, 1H), 7.86 (s, 1H), 7.51 (dd, 1H, J=7.5, 1.3 Hz), 7.35 (dd, 1H, J=7.1, 1.8 Hz), 7.30–7.18 (m, 4H), 7.06 (t, 1H, J=7.9 Hz), 6.00 (s, 1H), 3.83 (d, 1H, J=13.2 Hz), 3.68 (s, 3H), 3.61 (s, 3H), 3.53 (d, 1H, J=13.2 Hz), 2.96–2.78 (m, 3H), 2.64–2.50 (m, 1H) ppm.

C. Dimethyl 4-(2,6-dichlorophenyl)-2-{2-[4-(8-methyl-8-azabicyclo[3.2.1]oct-3-yl)-1-piperazinyl]-2-oxoethyl}-6-[2-(2-{[(trifluoromethyl) sulfonyl]amino}phenyl)ethyl]-1,4-dihydro-3,5-pyridinedicarboxylate This compound was synthesized according to a similar manner to that of example 1-F and quenched with buffer solution (pH 7.0, KH$_2$PO$_4$/Na$_2$B$_4$O$_7$) and brine, extracted with CH$_2$Cl$_2$ and concentrated in vacuo. The residue was purified by crystallization (CH$_2$Cl$_2$-hexane) to afford a yellow amorphous.

$^1$H-NMR (DMSO-d$_6$) δ 8.61 (s, 1H), 7.32(d, 2H, J=7.9 Hz), 7.25(d, 1H, J=7.3 Hz), 7.12 (t, 1H, J=7.3 Hz), 7.00 (d, 1H, J=7.5 Hz), 6.94(t, 1H, 7.7 Hz), 6.68(t, 1H, J=7.3 Hz), 5.84 (s, 1H), 4.17 (d, 1H, J=16.0 Hz), 3.85–2.30 (m, 25H), 2.20–2.00 (m, 2H), 2.00–1.68 (m, 6H) ppm.

HCl salt was prepared by a procedure similar to that described in example 1-H as a yellow solid.

mp 218–220° C.(dec.)

IR (KBr)ν$_{max}$: 2951, 2573, 2341, 1684, 1645, 1506, 1431, 1367, 1296, 1190, 1143, 1103, 1053, 966, 768, 606 cm$^{-1}$.

$^1$H-NMR (DMSO-d$_6$) δ 7.34 (d, 2H, J=7.7 Hz), 7.30–7.20 (br, 4H), 7.14 (t, 1H, J=7.4 Hz,), 5.86 (s, 1H), 4.24 (d, 1H, J=16.8 Hz,), 4.05–3.90 (br, 2H), 3.80–2.40 (m, 23H), 2.40–1.80 (m, 8H) ppm MS (m/z): 842 (M+H)$^+$ Example 17

Dimethyl 4-(2,6-dichlorophenyl)-2-{2-[4-(8-methyl-8-azabicyclo[3.2.1]oct-3-yl)-1-piperazinyl]-2-oxoethyl}-6-{2-[2-(1-piperazinylcarbonyl)phenyl]ethyl}-1,4-dihydro-3, 5-pyridinedicarboxylate A. Dimethyl2-[2-(2-{[4-(tert-butoxycarbonyl)-1-piperazinyl]carbonyl}phenyl)ethyl]-4-(2,6-dichlorophenyl)-6-{2-[4-(8-methyl-8-azabicyclo[3.2.1]oct-3-yl)-1-piperazinyl]-2-oxoethyl}-1,4-dihydro-3,5-pyridinedicarboxylate To a solution of 2-[2-(4-(2,6-dichlorophenyl)-3,5-bis (methoxycarbonyl)-6-{2-[4-(8-methyl-8-azabicyclo[3.2.1] oct-3-yl)-1-piperazinyl]-2-oxoethyl}-1,4-dihydro-2-pyridinyl)ethyl]benzoic acid (695 mg/0.76 mmol), tert-butyl 1-piperazinecarboxylate (455 mg/2.44 mmol), bromo-tris-pyrrolidino-phosphonium hexafluorophosphate (356 mg/0.76 mmol), in CH$_2$Cl$_2$ (8 ml) was added diisopropyl ethyl amine (42511/2.44 mmol) and stirred for 3 days at room temperature. The mixture was quenched with H$_2$O and extracted with CH$_2$Cl$_2$. The organic layer was washed with brine, dried over sodium sulfate, and concentrated in vacuo. The residue was purified by column chromatography on NH$_2$ gel to afford dimethyl 2-[2-(2-{[4-tert-butoxycarbonyl]-1-piperazinyl[carbonyl]phenyl)ethyl]-4-(2,6-dichlorophenyl)-6-{2-[4-(8-methyl-8-azabicyclo[3.2.1] oct-3-yl)-1-piperazinyl]-2-oxoethyl}-1,4-dihydro-3,5-pyridinedicarboxylate (458.4 mg/42%).

¹HNMR (CDCl₃, 70° C.) δ: 8.10 (s, 1H), 7.40–7.10 (m, 6H), 6.96 (t, 1H, J=8.4 Hz), 5.99 (s, 1H), 4.00–3.65 (br, 4H), 3.62–3.54 (m, 4H), 3.52 (s, 3H), 3.51 (s, 3H), 3.50–2.83 (br, 12H), 2.63–2.42 (m, 5H), 2.28 (s, 3H), 2.02–1.90 (m, 2H), 1.75–1.60 (m, 2H), 1.60–1.40 (m, 4H), 1.46 (s, 9H) ppm.

B. Dimethyl 4-(2,6-dichlorophenyl)-2-{2-[4-(8-methyl-8-azabicyclo[3.2.1]oct-3-yl)-1-piperazinyl]-2-oxoethyl}-6-{2-[2-(1-piperazinylcarbonyl)phenyl]ethyl}-1,4-dihydro-3,5-pyridinedicarboxylate A mixture of dimethyl 2-[2-(2-{[4-(tert-butoxycarbonyl)-1-piperazinyl]carbonyl}phenyl)ethyl]-4-(2,6-dichlorophenyl)-6-{2-[4-(8-methyl-8-azabicyclo[3.2.1]oct-3-yl)-1-piperazinyl]-2-oxoethyl}-1,4-dihydro-3,5-pyridinedicarboxylate (368 mg/0.41 mmol) and 2N HCl aqueous solution (8 ml/16 mmol) was refluxed for 2 hours. After cooling down, the mixture was basitified with saturated NaHCO₃ aqueous solution and extracted with ethyl acetate. The organic layer was washed with brine, dried over sodium sulfate, and concentrated in vacuo. The residue was purified by column chromatography on NH₂ gel (CH₂Cl₂:MeOH=200:1–20:1) to afford dimethyl 4-(2,6-dichlorophenyl)-2-{2-[4-(8-methyl-8-azabicyclo [3.2.1]oct-3-yl)-1-piperazinyl]-2-oxoethyl}-6-{2-[2-(1-piperazinylcarbonyl)phenyl]ethyl}-1,4-dihydro-3,5-pyridinedicarboxylate as a yellow amorphous.

¹HNMR (CDCl₃, 70° C.) δ; 8.03 (s, 1H), 7.38–7.10 (m, 6H), 6.95 (t, 1H, J=8.3 Hz), 5.99 (s, 1H), 4.00–3.68 (br, 4H), 3.62–3.54 (br, 4H), 3.53 (s, 3H), 3.50 (s, 3H), 3.30–3.12 (br, 4H) 3.03–2.69 (br, 8H), 2.63–2.40 (m, 5H), 2.27 (s, 3H), 2.05–1.93 (m, 2H), 1.74–1.60 (m, 2H), 1.59–1.46 (m, 4H) ppm.

HCl salt was prepared by a procedure similar to that described in example 1-H as a yellow solid.

mp 198–200° C.(dec.)

IR (KBr)ν_{max}: 3300, 2966, 2363, 2343, 1695, 1624, 1508, 1435, 1288, 1190, 1110, 1042, 1005, 953, 768 cm⁻¹.

MS (m/z):807 (M+H)+

Example 18

Dimethyl 4-(2,6-dichlorophenyl)-2-[2-(2-{[2-(ethylamino)ethoxy]methyl}phenyl)ethyl]-6-{2-[4-(8-methyl-8-azabicyclo[3.2.1]octyl)-1-piperazinyl]-2-oxoethyl}-1,4-dihydro-3,5-pyridinedicarboxylate A. Dimethyl4-(2,6-dichlorophenyl)-2-[2-(2-{[2-(ethylideneamino)ethoxy]methyl}phenyl)ethyl]-6-(2-methoxy-2-oxoethyl)-1,4-dihydro-3,5-pyridinedicarboxylate To a stirred solution of dimethyl 2-(2-{2-[(2-aminoethoxy)methyl]phenyl}ethyl)-4-(2,6-=-dichlorophenyl)-6-(2-methoxy-2-oxoethyl)-1,4-dihydro-3,5-pyridinedicarboxylate (2.0 g/3.38 mmol) and molecular sieves 3A powder (2.0 g) in chloroform (40 ml) was added acetaldehyde (328 mg/7.44 mmol) at room temperature under nitrogen atmosphere. The reaction mixture was stirred for 3 h. The reaction mixture was filtered and concentrated to give a yellow amorphous. This product was used for next reaction without purification.

¹H NMR (CDCl₃) δ: 9.09 (s, 1H), 7.69 (q, J=4.9 Hz, 1H), 7.46–6.95 (m, 7H), 6.05 (s, 1H), 4.60 (d, J=10.4 Hz, 1H), 4.51 (d, J=10.4 Hz, 1H), 3.85–3.48 (m, 6H), 3.70 (s, 3H), 3.60 (s, 3H), 3.52 (s, 3H), 2.95–2.70 (m, 4H), 1.89 (d, J=4.9 Hz, 3H) ppm.

B. Dimethyl4-(2,6-dichlorophenyl)-2-[2-(2-{[2-(ethylamino)ethoxy]methyl}phenyl)ethyl]-6-(2-methoxy-2-oxoethyl)-1,4-dihydro-3,5-pyridinedicarboxylate To an ice-cooled stirred solution of NaBH₄ (192 mg/5.07 mmol) in MeOH (40 ml) was added dimethyl 4-(2,6-dichlorophenyl)-2-[2-(2-{[2-(ethylideneamino)ethoxy]methylphenyl)ethyl)-6-(2-methoxy-2-oxoethyl)-1,4-dihydro-3,5-pyridinedicarboxylate (ca. 2.09 g). The resulting solution was warmed to room temperature and stirred for 1.5 h. The reaction mixture was quenched with NaHCO₃ aq. extracted with dichloromethane. The organic layer was washed with brine, dried over MgSO₄, filtered and concentrated to give a crude mixture. This crude was purified by column chromatography on NH₂ gel (Hexane:EtOAc=1:1) to afford a yellow amorphous (1.56 g/74% 2 steps).

¹H NMR (CDCl₃) δ 8.86 (s, 1H), 7.46–6.96 (m, 7H), 6.02 (s, 1H), 4.56 (s, 2H), 3.77–3.50 (m, 4H), 3.71 (s, 3H), 3.60 (s, 3H), 3.52 (s, 3H), 2.95–2.77 (m, 6H), 2.59 (q, J=7.1 Hz, 2H), 1.06 (t, J=7.1 Hz, 3H) ppm.

C. Dimethyl2-{2-[2-({2-[(tert-butoxycarbonyl)(ethyl)amino]ethoxy}methyl)phenyl]ethyl}-4-(2,6-dichlorophenyl)-6-(2-methoxy-2-oxoethyl)-1,4-dihydro-3,5-pyridinedicarboxylate To an ice-cooled stirred solution of dimethyl 4-(2,6-dichlorophenyl)-2-[2-(2-{[2-(ethylamino)ethoxy]methyl}phenyl)ethyl]-6-(2-methoxy-2-oxoethyl)-1,4-dihydro-3,5-pyridinedicarboxylate (700 mg/1.13 mmol) in dichloromethane (50 ml) was added di-t-butyl carbonate (297 mg/1.36 mmol) and triethylamine (172 mg/1.70 mmol). The reaction mixture was warmed to room temperature and stirred for 1.5 h. The reaction mixture was quenched with water. The separated organic layer was washed with water, dried over MgSO₄, filtered and concentrated to give a crude mixture. This crude was purified by column chromatography on silica gel (CH₂Cl₂:MeOH=40:1) to afford a yellow amorphous (813 mg/quant.).

¹H NMR (CDCl₃) δ 7.70–6.96 (m, 7H), 5.99 (s, 1H), 4.68 (d, J=11.5 Hz, 1H), 4.57 (d, J=11.5 Hz, 1H), 3.73–3.35 (m, 8H), 3.70 (s, 3H), 3.57 (s, 3H), 3.52 (s, 3H), 3.10–2.62 (m, 4H), 1.27 (s, 9H), 1.08 (t, J=6.9 Hz, 3H) ppm.

D. [6-{2-[2-((2-[(tert-butoxycarbonyl)(ethyl)amino]ethoxy}methyl)phenyl]ethyl}-4-(2,6-dichlorophenyl)-3,5-bis(methoxycarbonyl)-1,4-dihydro-2-pyridinyl]acetic Acid This compound was prepared by a procedure similar to that described in example 1 as a yellow amorphous. This product was used for next reaction without purification.

E. Dimethyl2-A2-[2-({2-[(tert-butoxycarbonyl)(ethyl)amino]ethoxy]methyl)phenyl]ethyl]-4-(2,6-dichlorophenyl)-6-(2-[4-(8-methyl-8-azabicyclo[3.2.1]oct-3-yl)-1-piperazinyl]-2-oxoethyl}-1,4-dihydro-3,5-pyridinedicarboxylate This compound was prepared by a procedure similar to that described in example 1 as a yellow amorphous.

¹H NMR (CDCl₃) δ: 8.18 (s, 1H), 7.34–6.97 (m, 7H), 5.99 (s, 1H), 4.63 (s, 2H), 4.12 (d, J=15.0 Hz, 1H), 3.75 (d, J=15.0 Hz, 1H), 3.62–3.20 (m, 19H), 2.97–2.79 (m, 4H), 2.64–2.43 (m, 5H), 2.28 (s, 3H), 2.08–1.98 (m, 2H), 1.76–1.51 (m, 8H), 1.43 (s, 9H), 1.06 (t, J=6.9 Hz, 3H) ppm.

F. Dimethyl4-(2,6-dichlorophenyl)-2-[2-(2-{[2-(ethylamino)ethoxy]methyl}phenyl)ethyl]-6-{2-[4-(8-methyl-8-azabicyclo[3.2.1]oct-3-yl)-1-piperazinyl]-2-oxoethyl}-1,4-dihydro-3,5-pyridinedicarboxylate The solution of dimethyl 2-{2-[2-({2-[(tert-butoxycarbonyl)(ethyl)amino]ethoxymethyl)phenyl]ethyl]-

4-(2,6-dichlorophenyl)-6-{2-[4-(8-methyl-8-azabicyclo[3.2.1]oct-3-yl)-1-piperazinyl]-2-oxoethyl}-1,4-dihydro-3,5-pyridinedicarboxylate (544 mg/0.61 mmol) and 2N-HCl (3 ml/6.0 mmol) in acetone (10 ml) was stirred at reflux temperature for 2 h. The reaction was quenched with K$_2$CO$_3$aq and extracted with dichloromethane. The separated organic layer was dried over MgSO$_4$, filtered and concentrated to give a crude mixture. This crude was purified by column chromatography on NH$_2$gel (CH$_2$Cl$_2$:MeOH=200:1–100:1) to afford a yellow amorphous (392 mg/81%).

Free Base $^1$H NMR (CDCl$_3$) δ: 8.38 (s, 1H), 7.36–6.97 (m, 7H), 6.00 (s, 1H), 4.62 (s, 2H), 4.01 (d, J=15.3 Hz, 1H), 3.80 (d, J=15.3 Hz, 1H), 3.69–3.51 (m, 12H), 3.19 (s, 2H), 2.94–2.78 (m, 4H), 2.65–2.44 (m, 5H), 2.61 (q, J=7.1 Hz, 2H), 2.28 (s, 3H), 2.01 (m, 2H), 1.78–1.50 (m, 8H), 1.08 (t, J=7.1 Hz, 3H) ppm.

Citrate Salt mp 151° C.

IR (KBr)v$_{max}$: 3402, 2949, 1695, 1624, 1508, 1433, 1292, 1190, 1103, 767 cm$^{-1}$ MS (m/z): 796 (M+H)$^+$ An Optical Isomer of dimethyl 4-(2,6-dichlorophenyl)-2–12-(2-([2-(ethylamino)ethoxy]methylphenyl)ethyl]-6-{2-[4-(8-methyl-8-azabicyclo[3.2.1]oct-3-yl)-1-piperazinyl]-2-oxoethyl}-1,4-dihydro-3,5-pyridinedicarboxylate The title enantiomer was obtained by chiral column seperation of the racemate dimethyl 4-(2,6-dichlorophenyl)-2-[2-(2-{[2-(ethylamino)ethoxy]methylphenyl)ethyl]-6-{2-[4-(8-methyl-8-azabicyclo[3.2.1]oct-3-yl)-1-piperazinyl]-2-oxoethyl}-1,4-dihydro-3,5-pyridinedicarboxylate. The racemate was resolved by HPLC using a chiral pak (DAICEL CHIRALPAK AD-H, 4.6×250 mm). HPLC condition was as follows:

| | |
|---|---|
| Apparatus: | Alliance with PDA detector, Waters |
| Column temperature: | 40° C. |
| Mobile phase: | Hexane/EtOH/Et$_2$NH = 85/15/0.1 |
| Detection: | 220 nm |
| Flow rate: | 1.0 mL/min |
| Injection volume: | 5 μL |
| Sample concentration: | 1.8 mg/mL |
| Dissolving solvent: | EtOH/H$_2$O = 10/1 |

Retention time of the title enantiomer was 10 minutes.

Example 19

Dimethyl 4-(2,6-dichlorophenyl)-2-{2-[4-(8-methyl-8-azabicyclo[3.2.1]oct-3-yl)-1-piperazinyl]-2-oxoethyl}-6-[2-(2-{[2-(1-pyrrolidinyl)ethoxy]methyl}phenyl)ethyl]-1,4-dihydro-3,5-pyridinedicarboxylate monosuccinate A. 1-(2-[(2-bromobenzyl)oxy]ethyl}pyrrolidine To a stirred suspension of potassium tert-butoxide (4.94 g, 44.0 mmol) in anhydrous THF (60 ml) was added dropwise a solution of 1-pyrrolidineethanol (5.07 g, 44.0 mmol) in anhydrous THF (20 ml) at 0° C. After 30 min at same temperature, to this was added dropwise a solution of 2-bromobenzyl bromide (10.0 g, 40.0 mmol) in anhydrous THF (20 ml) at 0° C. The reaction mixture was stirred at room temperature for 3 h. Water and 1:1 mixture of ethyl acetate and hexane were added to the reaction mixture and organic layer was separated. The organic layer was washed with water, brine and dried over sodium sulfate. After filtration, the filtrate was concentrated in vacuo to afford the titled compound (11.3 g, 99.3%) as a pale yellow oil.

C$_{13}$H$_{18}$BrNO

Exact Mass: 283.06

Mol. Wt.: 284.19

$^1$H NMR (CDCl$_3$) δ: 7.56–7.45 (m, 2H), 7.35–7.24 (m, 1H), 7.18–7.08 (m, 1H), 4.61 (s, 2H), 3.69 (t, J=5.5 Hz, 2H), 2.76 (t, J=5.5 Hz, 2H), 2.63–2.52 (m, 4H), 1.85–1.75 (m, 4H) ppm.

B. Ethyl (2E)-3-(2-{[2-(1-pyrrolidinyl)ethoxy]methyl}phenyl)-2-propenoate

A mixture of 1-{2-[(2-bromobenzyl)oxy]ethyl}pyrrolidine (11.3 g, 39.7 mmol), ethyl acrylate (8.6 ml, 79.4 mmol), potassium carbonate (13.7 g, 99.3 mmol), tetra-n-butylammonium bromide (12.8 g, 39.7 mmol), tri-o-tolylphosphine (483 mg, 1.59 mmol) and palladium acetate (178 mg, 0.79 mmol) in toluene (40 ml) was stirred at room temperature. The resulting mixture was degassed under reduced pressure and replaced with nitrogen. The mixture was stirred at 100° C. under nitrogen atmosphere for 15 h. After cooling to room temperature, the catalyst was filtered through a pad of celite, and filter cake was washed with toluene then ethyl acetate. The filtrate was evaporated in vacuo and the residue was dissolved with ethyl acetate-hexane (1:1)(200 ml)-2N HCl aq. (50 ml). The aqueous layer was separated and the organic layer was extracted with 2N HCl aq. (40 ml). The combined aqueous layers were basified to pH 9–10 with 2N NaOH aq. at 0° C. and extracted with ethyl acetate-hexane (1:1)(×3). The combined solution was washed with water, brine and dried over MgSO$_4$. After filtration, the filtrate was concentrated in vacuo to give crude product (dark orange oil), which was purified by column chromatography on NH$_2$ silica gel (500 g) (hexane/ethyl acetate 5/1–3/1 as eluent) to afford the titled compound (8.27 g, 69.0%) as a yellow oil.

C$_{18}$H$_{25}$NO$_3$

Exact Mass: 303.18

Mol. Wt.: 303.40

$^1$H NMR (CDCl$_3$) δ: 8.01 (d, J=16.0 Hz, 1H), 7.62–7.55 (m, 1H), 7.44–7.30 (m, 3H), 6.38 (d, J=16.0 Hz, 1H), 4.66 (s, 2H), 4.27 (q, J=7.1 Hz, 2H), 3.65 (t, J=6.1 Hz, 2H), 2.73 (t, J=6.1 Hz, 2H), 2.60–2.50 (m, 4H), 1.85–1.68 (m, 4H), 1.34 (t, J=7.1 Hz, 3H) ppm.

C. Ethyl 3-(2-{[2-(1-pyrrolidinyl)ethoxy]methyl}phenyl)propanoate

A mixture of ethyl (2E)-3-(2-{[2-(1-pyrrolidinyl)ethoxy]methyl}phenyl)-2-propenoate (8.27 g, 27.3 mmol) and 5% Pd/C (800 mg) in ethanol (50 ml) was hydrogenated under a hydrogen balloon for 3 h The reaction mixture was filtered through a pad of celite and the resulting Pd/C on the celite pad was washed with ethanol. The filtrate was evaporated in vacuo to afford the titled compound (8.10 g, 97.2%) as a yellow oil.

C$_{18}$H$_{27}$NO$_3$

Exact Mass: 305.20

Mol. Wt.: 305.41

$^1$H NMR (CDCl$_3$) δ: 7.38–7.14 (m, 4H), 4.57 (s, 2H), 4.14 (q, J=7.2 Hz, 2H), 3.61 (t, J=6.1 Hz, 2H), 3.04–2.95 (m, 2H), 2.71 (t, J=6.1 Hz, 2H), 2.67–2.58 (m, 2H), 2.59–2.48 (m, 4H), 1.85–1.70 (m, 4H), 1.24 (t, J=7.2 Hz, 3H) ppm.

D. 3-(2-{[2-(1-Pyrrolidinyl)ethoxy]methyl}phenyl)propanoic Acid

The solution of ethyl 3-(2-{[2-(1-pyrrolidinyl)ethoxy]methyl}phenyl)propanoate (8.10 g, 26.5 mmol) in ethanol (40 ml) and 5N NaOH aq. solution (32.0 mmol, 6.4 ml) was stirred at room temperature for 15 h. The mixture was neutrallized with 1N HCl-ethanol (32 ml) at 0° C. The solvents were removed by simple distillation procedure at ~1 atom (oil bath temperature; 105~110° C.). The residue was then diluted with acetonitrile (50 ml) and then the solvents were removed by distillation (oil bath temperature; 105~110° C.) for azeotropic removal of water and ethanol until inner temperature 79.5° C.~80.5° C. The residue was then diluted with acetonitrile (60 ml) and dried over sodium sulfate. After filtration, the filtrate was evaporated in vacuo to afford the titled compound (quant.) as a dark yellow oil.

C, $GH_{23}NO_3$

Exact Mass: 277.17

Mol. Wt.: 277.36

$^1$H NMR (CDCl$_3$) δ: 8.27 (br s, 1H), 7.35–7.10 (m, 4H), 4.56 (s, 2H), 3.77 (t, J=4.3 Hz, 2H), 3.10–2.95 (m, 8H), 2.51 (t, J=6.4 Hz, 2H), 1.98–1.86 (m, 4H) ppm.

E. Methyl 3-oxo-5-(2-{[2-(1-pyrrolidinyl)ethoxy]methyl}phenyl)pentanoate

To a stirred solution of 3-(2-{[2-(1-pyrrolidinyl)ethoxy]methyllphenyl)propanoic acid (~26.5 mmol) in anhydrous dimethylformamide (50 ml) was added portionwise carbonyldiimidazole (CDI)(4.30 g, 26.5 mmol) at room temperature. The reaction mixture was heated at 50° C. for 40 min. After cooling to r.t., to the mixture was added magnesium chloride (2.78 g, 29.2 mmol) then potassium methyl malonate (4.55 g, 29.2 mmol) at 0° C. The reaction mixture was heated at 50° C. for 15 h. The mixture was quenched with ethyl acetate-hexane (1:1)(50 ml) and aqueous solution of tri-sodium citrate (21.5 g, 72.9 mmol) in water (90 ml) and stirred at r.t. for 2 h. The organic layer was separated and the aqueous layer was extracted with ethyl acetate-hexane (1:1) (×4). The combined solution was washed with water (×3), brine, dried over MgSO$_4$ and concentrated in vacuo to afford the titled crude compound (7.65 g) as a dark yellow oil.

$C_{19}H_{27}NO_4$

Exact Mass: 333.19

Mol. Wt.: 333.42

$^1$H NMR (CDCl$_3$) δ: 7.35–7.14 (m, 4H), 4.55 (s, 2H), 3.72 (s, 3H), 3.61 (t, J 6.1 Hz, 2H), 3.45 (s, 2H), 3.01–2.84 (m, 4H), 2.70 (t, J=6.1 Hz, 2H), 2.58–2.49 (m, 2H), 1.83–1.73 (m, 4H) ppm.

F. Methyl3-(2,6-dichlorophenyl)-2-(3-(2-{[2-(1-pyrrolidinyl)ethoxy]methylphenyl)propanoyl]-2-propenoate This compound was prepared by a procedure similar to that described in example 1-C as a dark yellow oil.

$C_{26}H_{29}Cl_2NO_4$

Exact Mass: 489.15

Mol. Wt.: 490.42

$^1$H NMR (CDCl$_3$) δ: 7.62 (s, 1H), 7.40–7.00 (m, 7H), 4.58 and 4.49 (each s, total 2H), 3.85 and 3.62 (each s, total 3H), 3.67–3.55 (m, 2H), 3.20–2.84 (m, 4H), 2.75–2.66 (m, 2H), 2.60–2.50 (m, 4H), 1.83–1.70 (m, 4H) ppm.

G. Dimethyl 4-(2,6-dichlorophenyl)-2-(2-methoxy-2-oxoethyl)-6-[2-(2-{[2-(1-pyrrolidinyl)ethoxy]methyl}phenyl)ethyl]-1,4-dihydro-3,5-pyridinedicarboxylate This compound was prepared by a procedure similar to that described in example 1-D as a pale yellow amorphous.

$C_{33}H_{38}Cl_2N_2O_7$

Exact Mass: 644.21

Mol. Wt.: 645.57

$^1$H NMR (CDCl$_3$) δ: 7.83 (br s, 1H), 7.35–7.14 (m, 6H), 6.99 (dd, J=8.3, 7.5 Hz, 1H), 5.99 (s, 1H), 4.69 (d, J=11.7 Hz, 1H), 4.57 (d, J=11.7 Hz, 1H), 3.71 (s, 3H), 3.58 (s, 3H), 3.60–3.50 (m, 4H), 3.51 (s, 3H), 3.20–2.90 (m, 3H), 2.70–2.57 (m, 3H), 2.48–2.38 (m, 4H), 1.80–1.67 (m, 4H) ppm.

H. {4-(2,6-Dichlorophenyl)-3,5-bis(methoxycarbonyl)-6-[2-(2-{[2-(1-pyrrolidinyl)ethoxy]methylphenyl)ethyl]-1,4-dihydro-2-pyridinyl}acetic Acid This compound was prepared by a procedure similar to that described in example 1-E as a pale yellow amorphous. This product was used for next reaction without purification.

I. Dimethyl 4-(2,6-dichlorophenyl)-2-{2-[4-(8-methyl-8-azabicyclo[3.2.1]oct-3-yl)-1-piperazinyl]-2-oxoethyl}-6-[2-(2-{[2-(1-pyrrolidinyl)ethoxy]methyl}phenyl)ethyl]-1,4-dihydro-3,5-pyridinedicarboxylate This compound was prepared by a procedure similar to that described in example 1-F as a yellow amorphous.

$C_{44}H_{57}Cl_2N_5O_6$

Exact Mass: 821.37

Mol. Wt.: 822.86

$^1$H NMR (CDCl$_3$) δ: 8.17 (br s, 1H), 7.36–7.14 (m, 6H), 7.05–6.95 (m, 1H), 5.99 (s, 1H), 4.73–4.58 (m, 2H), 4.03 (d, J=15.0 Hz, 1H), 3.82 (d, J=15.0 Hz, 1H), 3.67–3.57 (m, 6H), 3.56 (s, 3H), 3.53 (s, 3H), 3.25–3.15 (m, 2H), 3.00–2.45 (m, 15H), 2.28 (s, 3H), 2.07–1.95 (m, 2H), 1.80–1.45 (m, 1OH) ppm.

J. Dimethyl 4-(2,6-dichlorophenyl)-2-{2-[4-(8-methyl-8-azabicyclo[3.2.1]oct-3-yl)-1-piperazinyl]-2-oxoethyl}-6-[2-(2-{[2-(-pyrrolidinyl)ethoxy]methyl}phenyl) ethyl]-1,4-dihydro-3,5-pyridinedicarboxylate monosuccinate This compound was prepared by a procedure similar to that described in example 1-H as a pale yellow solid.

Monosuccinic Acid Salt mp 168° C.(dec.)

IR (KBr)ν$_{max}$: 3383, 3080, 2949, 1693, 1647, 1576, 1508, 1435, 1290, 1227, 1194, 1161, 1115, 1101, 1053, 1034, 1001, 766 cm$^{-1}$.

MS (m/z): 822 (M+H)+820 (M–H)$^+$

Example 20

Dimethyl 4-(2,6-dichlorophenyl)-2-{2-[4-(8-methyl-8-azabicyclo[3.2.1]oct-3-yl)-1-piperazinyl]-2-oxoethyl}-6-[2-(2{2-(4-morpholinyl)ethoxy]methyl phenyl)ethyl]-1,4-dihydro-3,5-pyridinedicarboxylate A. 4-{2-[(2-bromobenzyl)oxy]ethyl}morpholine This compound was prepared by a procedure similar to that described in example 15A as a yellow oil.

$C_{13}H_{18}BrNO_2$

Exact Mass: 299.05

Mol. Wt.: 300.19

C, 52.01; H, 6.04; Br, 26.62; N, 4.67; O, 10.66

$^1$H NMR (CDCl$_3$) 8:7.50 (m, 2H), 7.31 (m, 1H), 7.14(m, 1H), 4.60 (s, 2H), 3.73 (t, J=4.4 Hz, 4H), 3.70 (t, J=5.7 Hz, 2H), 2.65 (t, J=5.7 Hz, 2H), 2.52 (t, J=4.4 Hz, 4H) ppm.

B. Ethyl (2E)-3-(2{[2-(4-morpholinyl)ethoxy]methyl}phenyl)-2-propenoate

This compound was prepared by a procedure similar to that described in example 15-B as a brown oil.

$C_{18}H_{25}NO_4$

Exact Mass: 319.18

Mol. Wt.: 319.40

C, 67.69; H, 7.89; N, 4.39; O, 20.04

$^1$H NMR (CDCl$_3$) 8:8.00 (d, J=16.0 Hz, 1H), 7.61–7.26 (m, 4H), 6.38(d, J=16.0 Hz, 1H), 4.65 (s, 2H), 4.27 (q, J=7.2

Hz, 2H), 3.71 (m, 4H), 3.65 (m, 2H), 2.64 (m, 2H), 2.50 (m, 4H), 1.34 (t, J=7.2 Hz, 3H) ppm.

C. Ethyl 3-(2-{[2-(4-morpholinyl)ethoxy]methyl}phenyl)propanoate

This compound was prepared by a procedure similar to that described in example 15-C as a brown oil.

$C_{18}H_{27}NO_4$

Exact Mass: 321.19

Mol. Wt.: 321.41

C, 67.26; H, 8.47; N, 4.36; 0, 19.91

$^1$H NMR (CDCl$_3$) δ: 7.36–7.19 (m, 4H), 4.57(s, 2H), 4.14(q, J=7.2 Hz, 2H), 3.79 (m, 4H), 3.70 (t, J=5.7 Hz, 2H), 3.00 (t, J=7.5 Hz, 2H), 2.71(t, J=5.7 Hz, 2H), 2.62 (m, 6H), 1.25 (t, J=7.2 Hz, 3H) ppm.

D. 3-(2-{[2-(4-morpholinyl)ethoxy]methylphenyl)propanoic Acid

This compound was prepared by a procedure similar to that described in example 15-C as a brown oil.

$C_{1-6}H_{23}NO_4$

Exact Mass: 293.16

Mol. Wt.: 293.36

C, 65.51; H, 7.90; N, 4.77; 0, 21.82

$^1$H NMR (CDCl$_3$) δ: 9.07 (br, 1H), 7.34–7.21 (m, 4H), 4.51 (s, 2H), 3.81 (m, 4H), 3.73 (t, J=5.3 Hz, 2H), 3.00 (t, J=7.3 Hz, 2H), 2.82 (m, 6H), 2.57 (t, J=7.3 Hz, 2H) ppm.

E. Methyl 5-(2-{[2-(4-morpholinyl)ethoxy]methyl}phenyl)-3-oxopentanoate

This compound was prepared by a procedure similar to that described in example 3-B as a brown oil.

$C_{19}H_{27}NO_5$

Exact Mass: 349.19

Mol. Wt.: 349.42

C, 65.31; H, 7.79; N, 4.01; 0, 22.89

$^1$H NMR (CDCl$_3$) δ:7.35–7.15 (m, 4H), 4.54 (s, 2H), 3.73 (s, 3H), 3.71 (m, 4H), 3.61 (m, 2H), 3.46 (s, 2H), 3.00–2.95 (m, 2H), 2.90–2.85 (m, 2H), 2.61 (m, 2H), 2.49 (m, 4H) ppm.

F. Methyl(2Z)-3-(2,6-dichlorophenyl)-2-[3-(2-([2-(4-morpholinyl)ethoxy]methyl}phenyl)propanoyl]-2-propenoate This compound was prepared by a procedure similar to that described in example 1C as a brown oil. This product was used for next reaction without purification.

$C_{26}H_{29}Cl_2NO_5$

Exact Mass: 505.14

Mol. Wt.: 506.42

C, 61.66; H, 5.77; Cl, 14.00; N, 2.77; O, 15.80

$^1$H NMR (CDCl$_3$) δ: 7.63 (s, 1H), 7.36–7.05 (m, 7H), 4.58 and 4.48 (s, 2H), 3.86 and 3.62 (s, 3H), 3.74–3.56 (m, 6H), 3.18–2.85 (m, 4H), 2.63–2.57 (m, 2H), 2.50–2.47 (m, 4H) ppm.

G. Dimethyl 4-(2,6-dichlorophenyl)-2-(2-methoxy-2-oxoethyl)-6-[2-(2-{[2-(4-morpholinyl)ethoxy]methyl}phenyl)ethyl]-1,4-dihydro-3,5-pyridinedicarboxylate This compound was prepared by a procedure similar to that described in example 1-D as a yellow amorphous.

$C_{33}H_{38}Cl_2N_2O_8$

Exact Mass: 660.20

Mol. Wt.: 661.57

C, 59.91; H, 5.79; Cl, 10.72; N, 4.23; O, 19.35

$^1$H NMR (CDCl$_3$) δ: 7.62 (s, 1H), 7.30–6.97 (m, 7H), 5.99 (s, 1H), 4.67 (d, J=11.7 Hz, 1H), 4.62 (d, J=11.7 Hz, 1H), 3.71 (s, 3H), 3.58 (s, 3H), 3.74–3.54 (m, 8H), 3.51 (s, 3H), 3.15–2.93 (m, 3H), 2.77–2.67 (m, 1H), 2.57–2.53 (m, 2H), 2.42–2.35 (m, 4H) ppm.

H. {4-(2,6-dichlorophenyl)-3,5-bis(methoxycarbonyl)-6-[2-(2-{[2-(4-morpholinyl)ethoxy]methyl}phenyl)ethyl]-1,4-dihydro-2-pyridinyl}acetic Acid This compound was prepared by a procedure similar to that described in example 1-E as a yellow amorphous. This product was used for next reaction without purification.

$C_{32}H_{36}Cl_2N_2O_8$

Exact Mass: 646.18

Mol. Wt.: 647.54

C, 59.35; H, 5.60; Cl, 10.95; N, 4.33; O, 19.77

I. Dimethyl 4-(2,6-dichlorophenyl)-2-{2-[4-(8-methyl-8-azabicyclo[3.2.1]oct-3-yl)-1-piperazinyl]-2-oxoethyl)-6-[2-(2-{[2-(4-morpholinyl) ethoxy]methylphenyl)ethyl]-1,4-dihydro-3,5-pyridinedicarboxylate This compound was prepared by a procedure similar to that described in example 1-F as a yellow amorphous.

Free Base $C_{44}H_{57}Cl_2N_5O_7$

Exact Mass: 837.36

Mol. Wt.: 838.86

C, 63.00; H, 6.85; Cl, 8.45; N, 8.35; O, 13.35

$^1$H NMR (CDCl$_3$) δ 8.16 (s, 1H), 7.33–6.98 (m, 7H), 5.99 (s, 1H), 4.65 (s, 2H), 4.10 (d, J=15.0 Hz, 1H), 3.76 (d, J=15.0 Hz, 1H), 3.70–3.50 (m, 10H), 3.55 (s, 3H), 3.54 (s, 3H), 3.28–3.15 (m, 2H), 3.02–2.83(m, 3H), 2.62–2.45 (m, 12H), 2.28 (s, 3H), 2.08–1.50 (m, 8H) ppm.

Mono-Succinate Salt mp 122.

IR (KBr)ν$_{max}$: 3201, 2947, 2860, 1697, 1631, 1575, 1515, 1433, 1290, 1193, 1114, 765 cm$^{-1}$ MS (m/z): 838.28(M+H)$^+$ The chemical structures of the compounds prepared in the Examples 1 to 18 are summarized in the following table.

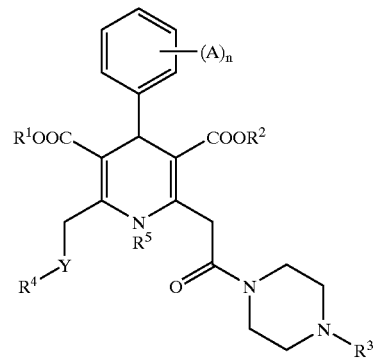

(wherein (A)$_n$ is 2,6-dichloro; R$^1$ and R$^2$ are methyl; R$^5$ is hydrogen; Y is —(CH$_2$)—; R$^3$ is 8-methylbicyclo[3.2.1]oct-3-yl; and R$^4$ is 2-substituted-phenyl.)

TABLE

| Ex. # | Substituent of 2-position of phenyl moiety in R⁴ |
| --- | --- |
| 1 | 2-aminoethoxymethyl |
| 2 | 2-aminoethoxy |
| 3 | 3-aminopropoxy |
| 4 | 3-aminopropoxymethyl |
| 5 | phenylthiomethyl |
| 6 | 3-dimethylaminopropyl |
| 7 | diethylaminomethyl |
| 8 | hydroxy |
| 9 | morpholinomethyl |
| 10 | methylsulfonylamino |
| 11 | 2-(2-oxo-pyrrolidinyl)ethoxy |
| 12 | tert-butoxycarbonylpiperazinylmethyl |
| 13 | 2,2,2-trifluoroethylamino |
| 14 | 4-(methylamino)-4-oxobutanoyl-aminomethyl |
| 15 | 2-diethylaminoethoxymethyl |
| 16 | trifluoromethylsulfonylamino |
| 17 | 1-piperazinylcarbonyl |
| 18 | 2-(ethylamino)ethoxymethyl |
| 19 | 2-pyrrolidinoethoxymethyl |
| 20 | 2-morpholinoethoxymethyl |

17 1-piperazinylcarbonyl

What is claimed is:

1. A compound of the formula

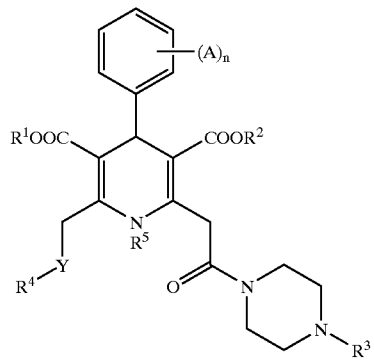

(I)

wherein A is independently halo;
Y is;
$R^1$ and $R^2$ are independently $C_{1-4}$ alkyl;
$R^3$ is selected from
(a) $C_{7-14}$ azacyclo-, azabicyclo- or azatricyclo-alkyl, in which the nitrogen atom optionally has a substituent selected from $C_{1-4}$ alkyl, benzyl optionally substituted with one or two substituents independently selected from halo and halosubstituted-$C_{1-4}$ alkyl, $C_{1-4}$ alkoxycarbonyl optionally substituted with one or two halogen atoms and $C_{1-6}$ acyl;
$R^4$ is phenyl substituted at the 2-position with substituent selected from
(a) $C_{1-4}$ alkyl substituted with one or two substituents independently selected from amino, amino-$C_{2-4}$ alkoxy, phenylthio, $C_{1-4}$ alkyl-phenylthio, di-$C_{1-4}$ alkylamino-$C_{2-4}$ alkoxy, $C_{1-4}$ alkylamino-$C_{2-4}$ alkoxy, $C_{1-4}$ alkylamino, di-$C_{1-4}$ alkylamino, hydroxy, piperazinyl, oxopyrrolidinyl, pyrrolidinyl, morpholino, $C_{1-4}$ alkylaminocarbonyl-$C_{1-6}$ acylamino, $C_{1-4}$ alkoxycarbonyl-$C_{1-6}$ acylamino, $C_{1-4}$ alkoxycarbonylpiperazinyl, pyrrolidinyl-$C_{1-4}$ alkoxy, morpholino, $C_{1-4}$ alkoxy acylpiperazinyl,
(b) piperidnoethoxy;
(c) $C_{1-4}$ alkoxy substituted with one or two substituents independently selected from amino, $C_{1-4}$ alkylamino, di-$C_{1-4}$ alkylamino, hydroxy, piperazinyl, oxopyrrolidinyl, pyrrolidinyl, morpholino, $C_{1-4}$ alkylaminocarbonyl-$C_{1-6}$ acylamino, $C_{1-4}$alkoxycarbonyl-$C_{1-6}$ acylamino, $C_{1-4}$alkoxycarbonylpiperazinyl, and $C_{1-6}$ acylpiperazinyl,
(d) amino, $C_{1-4}$ alkylamino, $C_{1-6}$ acylamino, aminoacetylamino, $C_{1-4}$ alkylsulfonylamino, halosubstituted-$C_{1-4}$ alkylsulfonylamino, halosubstituted-$C_{1-4}$ alkylamino or $C_{1-4}$ alkoxycarbonylaminoacetylamino;
(e) piperazinylcarbonyl and hydroxy, or di-$C_{1-4}$ alkylaminosulphenyl;
$R^5$ hydrogen or $C_{1-4}$ alkyl; and
n is 0, 1, 2, 3, 4 or 5;
or a pharmaceutically acceptable salt thereof.

2. A compound according to claim 1, wherein the compound of formula (I) or pharmaceutically acceptable salt thereof, has the following stereochemistry

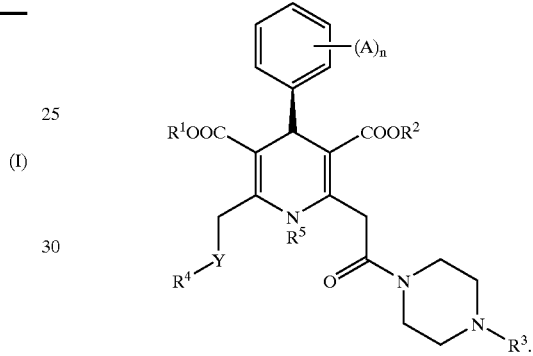

I(a)

3. A compound according to claim 1, wherein the compound of formula (I), or pharmaceutically acceptable salt thereof, has the following stereochemistry

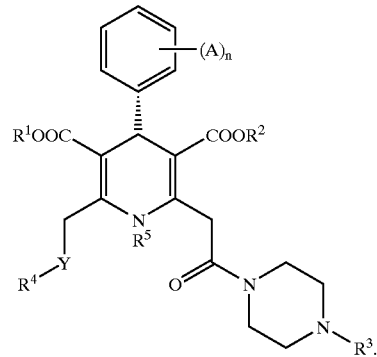

I(b)

4. A compound according to claim 1, wherein the azabicyclo- or azatricyclo-alkyl group of $R^3$ is in the exo orientation.

5. A compound according to claim 1, wherein the azabicyclo- or azatricyclo-alkyl group of $R^3$ is in the endo orientation.

6. A compound according to claim 1, wherein
 $(A)_n$ is 2,6-dichloro; $R^1$ and $R^2$ are methyl;
 and $R^5$ is hydrogen.

7. A compound according to claim 6, wherein
 $R^3$ is $C_{6-9}$ azabicycloalkyl optionally substituted with $C_{1-4}$ alkyl, benzyl or $C_{1-4}$ acyl.

8. A compound according to claim 7, wherein

R$^3$ is selected from methlylazabicyclo[3.2.1]octyl, ethylazabicyclo[3.2.1]octyl and formylazabicyclo [3.2.1]octyl; and R$^4$ is phenyl substituted at the 2-position wit substituent selected from ethylenedioxyethyl, aminoethoxymethyl, aminoethoxy, aminopropoxy, aminopropoxymethyl, phenylthiomethyl, (dimethylamino)propyl, diethylaminomethyl, hydroxy, morpholinomethyl, methanesulphonylamino, oxopyrrolidinoethoxy, t-butoxycarbonylpiperazinomethyl, trifluoro-ethylamino, methylcarbamoylpropanoylaminomethyl, diethylaminoethoxymethyl, trifuloromethane-sulfonylamino, piperazinocarbonyl, ethyl-aminoethoxymethyl, pyrrolidinoethoxymethyl, morpholinoethoxymethyl, piperidinoethoxy and dimethylaminoethoxy.

9. A compound according to claim 8, wherein R$^3$ is selected from 8-methlyl-8-azabicyclo[3.2.1]oct-3-yl, 8-ethyl-8-azabicyclo[3.2.1]oct-3-yl and 8-formyl-8-azabicyclo[3.2.1] oct-3-yl.

10. A compound according to claim 9, wherein the 8-methlyl-8-azabicyclo[3.2.1]oct-3-yl, 8-ethyl-8-azabicyclo[3.2.1]oct-3-yl or 8-formyl-8-azabicyclo[3.2.1]oct-3-yl group of R$^3$ is in the exo orientation.

11. A compound according to claim 9, wherein the 8-methlyl-8-azabicyclo[3.2.1]oct-3-yl, 8-ethyl-8-azabicyclo[3.2.1]oct-3-yl or 8-formyl-8-azabicyclo[3.2.1]oct-3-yl group of R$^3$ is in the endo orientation.

12. A compound according to claim 1 selected from the group consisting of:

Dimethyl-2-(2-{2-[(2-aminoethoxy)methyl] phenyl}ethyl)-4-(2,6-dichlorophenyl)-6-{2-[4-(8-methyl-8-azabicyclo[3.2.1]oct-3-yl)-1-piperazinyl]-2-oxoethyl}-1,4-dihydro-3,5-pyridinedicarboxylate;

Dimethyl-2-{2-[2-(2-aminoethoxy)phenyl]ethyl}-4-(2,6-dichlorophenyl)-6-{2-[4-{8-methyl-8-azabicyclo[3.2.1]oct-3-yl)-1-piperazinyl]-2-oxoethyl}-1,4-dihydro-3,5-pyridinedicarboxylate;

Dimethyl-2-{2-[2-(3-aminopropoxy)phenyl]ethyl}-4-{2,6-dichlorophenyl)-6-{2-[4-(8-methyl-8-azabicyclo[3.2.1]oct-3-yl)-1-piperazinyl]-2-oxoethyl}-1,4-dihydro-3,5-pyridinedicarboxylate;

Dimethyl-2-(2-{2-[3-aminopropoxy)methyl] phenyl}ethyl)-4-(2,6-dichorophenyl)-6-{2-[4-(8-methyl-8-azabicyclo[3.2.1]oct-3-yl)-1-piperazinyl]-2-oxoethyl}-1,4-dihydro-3,5-pyridinedicarboxylate;

Dimethyl-4-(2,6-dichlorophenyl)-2-{2-[4-(8-methyl-8-azabicyclo[3.2.1]oct-3-yl)-1-piperazinyl]-2-oxoethyl}-6-{2-[(phenylsulfanyl)methyl]phenethyl}-1,4-dihydro-3,5-pyridinedicarboxylate;

Dimethyl-4-(2,6-dichlorophenyl)-2-(2-{2-[3-(dimethylamino)propyl]phenyl}ethyl)-6-{2-(4-(8-methyl-8-azabicyclo[3,2,1]oct-3-yl)-1-piperazinyl]-2-oxoethyl}-1,4-dihydro-3,5-pyridinecarboxylate;

Dimethyl-4-(2,6-dichlorophenyl)-2-(2-{2-[(diethylamino)methyl]phenyl}ethyl)-6-{2-[4-(8-methyl-8-azabicyclo[3.2.1]oct-3-yl)-1-piperazinyl]-2-oxoethyl}-1,4-dihydro-3,5-pyridinedicarboxylate;

Dimethyl-4-(2,6-dichlorophenyl)-2-[2-(2-hydroxyphenyl)ethyl]-6-{2-[4-(8-methyl-8-azabicyclo[3.2.1]oct-3-yl)-1-piperazinyl]-2-oxoethyl}-1,4-dihydro-3,5-pyridinedicarboxylate;

Dimethyl-4-(2,6-dichlorophenyl)-2-[2-[4-(8-methyl-8-azabicyclo[3.2.1]oct-3-yl)-1-piperazinyl]-2-oxoethyl}-6-(2-[2-(4-morpholinylmethyl)phenyl]ethyl]-1,4-dihydro-3,5-pyridinedicarboxylate;

Dimethyl-4-(2,6-dichlorophenyl)-2-{2-[4-(8-methyl-8-azabicyclo[3.2.1]oct-3-yl)-1-piperazinyl]-2-oxoethyl}-6-(2-{2-[(methylsulfonyl)amino]phenyl}ethyl)-1,4-dihydro-3,5-pyridinedicarboxylate;

Dimethyl-4-(2,6-dichlorophenyl)-2-{2-[4-(8-methyl-8-azabicyclo[3.2.1]oct-3-yl)-1-piperazinyl]-2-oxoethyl}-6-(2-{2-[2-(2-oxo-1-pyrrolidinyl)ethoxy] phenyl}ethyl)-1,4-dihydro-3,5-pyridinedicarboxylate;

Dimethyl-2-[2-(2-{[4-(tert-butoxycarbonyl)-1-piperazinyl]methyl}phenyl)ethyl]-4-(2,6-dichlorophenyl)-6-{2-[4-(8-methyl-8-azabicyclo[3.2.1]oct-3-yl)-1-piperazinyl]-2-oxoethyl}-1,4-dihydro-3,5-pyridinedicarboxylate;

Dimethyl-4-(2,6-dichlorophenyl)-2-{2-[4-(8-methyl-8-azabicyclo[3.2.1]oct-3-yl)-1-piperazinyl]-2-oxoethyl}-6-(2-{2-[(2,2,2-trifluoroethyl)amino]phenyl}ethyl)-1,4-dihydro-3,5-pyridinedicarboxylate;

Dimethyl-4-(2,6-dichlorophenyl)-2-{2-[2-({(4-(methylamino)-4-oxobutanoyl]amino}methyl)phenyl] ethyl}-6-{2-[4-(8-methyl-8-azabicyclo[3.2.1]oct-3-yl)-1-piperazinyl]-2-oxoethyl}-1,4-dihydro-3,5-pyridinedicarboxylate;

Dimethyl-4-(2,6-dichlorophenyl)-2-[2-(2-{[2-(diethylamino)ethoxy]methyl}phenyl)ethyl]-6-{2-[4-(8-methyl-8-azabicyclo[3.2.1]oct-3-yl)-1-piperazinyl]-2-oxoethyl}-1,4-dihydro-3,5-pyridinedicarboxylate;

4-(2,6-Dichloro-phenyl-2-{2-[2-(2-diethylamino-ethoxymethyl)-phenyl]-ethyl}-6-{2-[4-(8-methyl-8-aza-bicyclo[3.2.1]oct-3-yl)-piperazin-1-yl]-2-oxo-ethyl}-1,4-dihydro-pyridine-3,5-dicarboxylic acid dimethyl ester;

Dimethyl-4-(2,6-dichlorophenyl)-2-{2-[4-(8-methyl-8-azabicyclo[3.2.1]oct-3-yl)-1-piperazinyl]-2-oxoethyl}-6-[2-{2-{[(trifluoromethyl)sulfonyl]amino}phenyl) ethyl]-1,4-dihydro-3,5-pyridinedicarboxylate;

Dimethyl-4-(2,6-dichlorophenyl)-2-{2-[4-(8-methyl-8-azabicyclo[3.2.1]oct-3-yl)-1-piperazinyl]-2-oxoethyl}-6-{2-[2-(1-piperazinylcarbonyl)phenyl]ethyl}-1,4-dihydro-3,5-pyridinedicarboxylate;

Dimethyl-4-(2,6-dichlorophenyl)-2-12-(2-{[2-(ethylamino)ethoxy]methyl}phenyl)ethyl]-6-{2-[4-(8-methyl-8-azabicyclo[3.2.1]oct-3-yl)-1-piperazinyl]-2-oxoethyl}-1,4-dihydro-3,5-pyridinedicarboxylate;

Dimethyl-4-(2,6-dichlorophenyl)-2-[2-(2-{[2-pyrrolidinoethoxy]methyl}phenyl)ethyl]-6-{2-[4-(8-methyl-8-azabicyclo[3.2.1]oct-3-yl)-1-piperazinyl]-2-oxoethyl}-1,4-dihydro-3,5-pyridinedicarboxylate;

Dimethyl-4-(2,6-dichlorophenyl)-2-[2-(2-{[2-morpholinoethoxy]methyl}phenyl)ethyl]-6-{2-[4-(8-methyl-8-azabicyclo[3.2.1]oct-3-yl)-1-piperazinyl]-2-oxoethyl}-1,4-dihydro-3,5-pyridinedicarboxylate;

and pharmaceutically acceptable salts thereof.

13. A compound according to claim 12 selected from the group consisting of:

Dimethyl-2-(2-{2-[(2-aminoethoxy)methyl] phenyl}ethyl)-4-(2,6-dichlorophenyl)-6-{2-[4-(8-methyl-8-azabicyclo[3.2.1]oct-3-yl)-1-piperazinyl]-2-oxoethyl}-1,4-dihydro-3,5-pyridinedicarboxylate;

Dimethyl-4-(2,6-dichlorophenyl)-2-(2-{2-[3-(dimethylamino)propyl]phenyl}ethyl)-6-{2-[4-(8-methyl-8-azabicyclo[3.2.1]oct-3-yl)-1-piperazinyl]-2-oxoethyl}-1,4-dihydro-3,5-pyridinecarboxylate;

Dimethyl-4-(2,6-dichlorophenyl)-2-(2-{2-[(diethylamino)methyl]phenyl}ethyl)-6-{2-[4-(8- methyl-8-azabicyclo[3.2.1]oct-3-yl)-1-piperazinyl]-2-oxoethyl}-1,4-dihydro-3,5-pyridinedicarboxylate;

Dimethyl-4-(2,6-dichlorophenyl)-2-{2-[4-(8-methyl-8-azabicyclo[3.2.1]oct-3-yl)-1-piperazinyl]-2-oxoethyl}-6-(2-{2-[(methylsulfonyl)amino]phenyl}ethyl)-1,4-dihydro-3,5-pyridinedicarboxylate;

Dimethyl-4-(2,6-dichlorophenyl)-2-{2-[4-(8-methyl-8-azabicyclo[3.2.1]oct-3-yl)-1-piperazinyl]-2-oxoethyl}-6-(2-{2-[2-(2-oxo-1-pyrrolidinyl)ethoxy)phenyl}ethyl)-1,4-dihydro-3,5-pyridinedicarboxylate;

Dimethyl-4-(2,6-dichlorophenyl)-2-{2-[2-({[4-(methylamino)-4-oxobutanoyl]amino)methyl)phenyl]ethyl}-6-{2-[4-(8-methyl-8-azabicyclo[3.2.1]oct-3-yl)-1-piperazinyl]-2-oxoethyl}-1,4-dihydro-3,5-pyridinedicarboxylate;

Dimethyl-4-(2,6-dichlorophenyl)-2-[2-(2-{[2-(diethylamino)ethoxy]methyl}phenyl)ethyl]-{2-[4-(8-methyl-8-azabicyclo[3.2.1]oct-3-yl)-1-piperazinyl]-2-oxoethyl}-1,4-dihydro-3,5-pyridinedicarboxylate;

4-(2,6-Dichloro-phenyl)-2-{2-[2-(2-diethylamino-ethoxymethyl)-phenyl]-ethyl}-6-{2-[4-(8-methyl-8-aza-bicyclo[3.2.1]oct-3-yl)-piperazin-1-yl]-2-oxo-ethyl}-1,4-dihydro-pyridine-3,5-dicarboxylic acid dimethyl ester;

Dimethyl-4-(2,6-dichlorophenyl)-2-{2-[4-(8-methyl-8-azabicyclo[3.2.1]oct-3-yl)-1-piperazinyl]-2-oxoethyl}-6-{2-[2-(1-piperazinylcarbonyl)phenyl]ethyl}-1,4-dihydro-3,5-pyridinedicarboxylate;

and pharmaceutically acceptable salts thereof.

14. A compound according to claim 13, wherein said compound is (4R)-(−)-4-(2,6-Dichloro-phenyl)-2-{2-[2-(2-diethylamino-ethoxymethyl)-phenyl]-ethyl}-6-{2-[4-(exo)-(8-methyl-8-aza-bicyclo[3.2.1]oct-3-yl)-piperazin-1-yl]-2-oxo-ethyl}-1,4-dihydro-pyridine-3,5-dicarboxylic acid dimethyl ester, or a pharmaceutically acceptable salt thereof.

15. A compound according to claim 14, wherein said compound is (4R)-(−)-4-(2,6-Dichloro-phenyl)-2-{2-[2-(2-diethylamino-ethoxymethyl)-phenyl]-ethyl}-6-{2-[4-(exo)-(8-methyl-8-aza-bicyclo[3.2.1]oct-3-yl)-piperazin-1-yl]-2-oxo-ethyl}-1,4-dihydro-pyridine-3,5-dicarboxylic acid dimethyl ester, monosuccinic acid.

16. A pharmaceutical composition which comprises a therapeutically effective amount of a compound according to claim 1 and a pharmaceutically acceptable carrier.

17. A compound named Dimethyl-4-(2,6-dichlorophenyl)-2-[2-(2-{[2-(diethylamino)ethoxy]methyl}phenyl)ethyl]-6-{2-[4-(8-methyl-8-azabicyclo[3.2.1]oct-3-yl)-1-piperazinyl]-2-oxoethyl}-1,4-dihydro-3,5-pyridinedicarboxylate.

18. A pharmaceutical composition comprising a therapeutically effective amount of the compound of claim 17 and a pharmaceutically acceptable carrier.

* * * * *